US009447117B2

(12) United States Patent
Gelin et al.

(10) Patent No.: US 9,447,117 B2
(45) Date of Patent: Sep. 20, 2016

(54) SUBSTITUTED 2-AZABICYCLES AND THEIR USE AS OREXIN RECEPTOR MODULATORS

(71) Applicant: Janssen Pharmaceutica NV, Beerse (BE)

(72) Inventors: Christine F. Gelin, San Diego, CA (US); Terry P. Lebold, San Diego, CA (US); Brock T. Shireman, Poway, CA (US)

(73) Assignee: Janssen Pharmaceuticals NV, Beerse (BE)

( * ) Notice: Subject to any disclaimer, the term of this patent is extended or adjusted under 35 U.S.C. 154(b) by 0 days.

(21) Appl. No.: 14/605,387

(22) Filed: Jan. 26, 2015

(65) Prior Publication Data
US 2015/0174129 A1    Jun. 25, 2015

Related U.S. Application Data

(62) Division of application No. 14/206,722, filed on Mar. 12, 2014, now Pat. No. 8,969,352.

(60) Provisional application No. 61/780,378, filed on Mar. 13, 2013.

(51) Int. Cl.
| A61K 31/407 | (2006.01) |
| C07D 513/04 | (2006.01) |
| C07D 413/14 | (2006.01) |
| C07D 401/12 | (2006.01) |
| C07D 401/14 | (2006.01) |
| C07D 403/14 | (2006.01) |
| C07D 471/08 | (2006.01) |
| C07D 487/08 | (2006.01) |
| C07D 519/00 | (2006.01) |
| A61K 31/4439 | (2006.01) |
| A61K 31/444 | (2006.01) |
| A61K 31/4709 | (2006.01) |
| A61K 31/4725 | (2006.01) |
| A61K 31/497 | (2006.01) |
| A61K 31/506 | (2006.01) |
| C07D 405/14 | (2006.01) |
| C07D 417/14 | (2006.01) |

(52) U.S. Cl.
CPC .......... *C07D 513/04* (2013.01); *A61K 31/444* (2013.01); *A61K 31/4439* (2013.01); *A61K 31/4709* (2013.01); *A61K 31/4725* (2013.01); *A61K 31/497* (2013.01); *A61K 31/506* (2013.01); *C07D 401/12* (2013.01); *C07D 401/14* (2013.01); *C07D 403/14* (2013.01); *C07D 405/14* (2013.01); *C07D 413/14* (2013.01); *C07D 417/14* (2013.01); *C07D 471/08* (2013.01); *C07D 487/08* (2013.01); *C07D 519/00* (2013.01)

(58) Field of Classification Search
CPC .................................................. A61K 31/407
See application file for complete search history.

(56) References Cited

U.S. PATENT DOCUMENTS

2014/0275065 A1    9/2014  Coate
2015/0328224 A1   11/2015  Coate et al.

FOREIGN PATENT DOCUMENTS

| WO | WO 2004/074292 A | 9/2004 |
| WO | WO 2008/150364 A | 12/2008 |
| WO | WO 2009/104155 A | 8/2009 |
| WO | WO 2010/063663 A | 6/2010 |
| WO | WO 2010/122151 A | 10/2010 |
| WO | WO 2011/050198 A | 4/2011 |
| WO | WO 2011/050200 A | 4/2011 |
| WO | WO 2012/089606 A | 7/2012 |
| WO | WO 2012/145581 A | 10/2012 |
| WO | WO 2014/075392    | 5/2014 |

OTHER PUBLICATIONS

Ammoun et al, "Distinct Recognition of OX1 and OX2 Receptors by Orexin Peptides", *Journal of Pharmacology and Experimental Therapeutics* (2003) 305(2):507-514.
Arendt et al, "Depressive Behavior and Activation of the Orexin/Hypocretin System", *Behavioral Neuroscience* (2013) 127(1):86-94.
Borgland et al, "Orexin A in the VTA Is Critical for the Induction of Synaptic Plasticity and Behavioral Sensitization to Cocaine", *Neuron* (2006) 49:589-601.

(Continued)

*Primary Examiner* — Bruck Kifle
(74) *Attorney, Agent, or Firm* — Baker & Hostetler LLP

(57) ABSTRACT

The present invention is directed to compounds of Formula I:

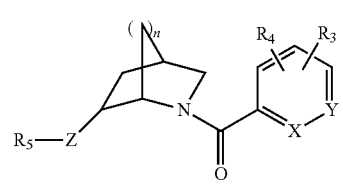

wherein X is N or $CR_1$; Y is N or $CR_2$; $R_1$ is H, alkoxy, halo, triazolyl, pyrimidinyl, oxazolyl, isoxazole, oxadiazolyl, or pyrazolyl; $R_2$ is H, alkyl, alkoxy, or halo; Z is NH or O; $R_3$ is H, alkyl, alkoxy, halo, or triazolyl; $R_4$ is H or alkyl; or $R_3$ and $R_4$, together with the atoms to which they are attached, form a 6- membered aryl ring or a 5- or 6-membered heteroaryl ring; $R_5$ is pyridyl, pyrazinyl, or pyrimidinyl, wherein the pyridyl, pyrazinyl, or pyrimidinyl is optionally substituted with halo or alkyl; and n is 1 or 2. Methods of making the compounds of Formula I are also described. The invention also relates to pharmaceutical compositions comprising compounds of Formula I. Methods of using the compounds of the invention are also within the scope of the invention.

15 Claims, 2 Drawing Sheets

(56) References Cited

OTHER PUBLICATIONS

Brundin et al, "Reduced orexin levels in the cerebrospinal fluid of suicidal patients with major depressive disorder", *European Neuropsychopharmacology* (2007) 17:573-579.

Carroll et al, "Synthesis and Muscarinic Receptor Activity of Ester Derivatives of 2-Substituted 2-Azabicyclo[2.2.1]heptan-5-ol and -6-ol", *Journal of Medicinal Chemistry* (1992) 35(12):2184-2191.

Chemelli et al, "Narcolepsy in orexin Knockout Mice: Molecular Genetics of Sleep Regulation", Cell (1999) 98:437-451.

Chen et al, "Pressor effects of orexins injected intracisternally and to rostral ventrolateral medulla of anesthetized rats", *American Journal of Physiol. Regulatory Integrative Comp. Physiol.* (2000) 278:R692-R697.

Chiu, "An improved procedure for the synthesis of chiral 2-azabicyclo[2.2.1]heptane", *Synthetic Communications* (1996) 26(3):577-584.

De Lecea, Chatper 3, "Hypocretins and the neurobiology of sleep-wake mechanisms", *Progress in Brain Research* (2012) vol. 198, A. Shekhar (Ed.), pp. 15-24.

Fortuyn et al, "Anxiety and mood disorders in narcolepsy: a case-control study", *General Hopsital Psychiatry* (2010) 32:49-56.

Hara et al, "Genetic Ablation of Orexin Neurons in Mice Results in Narcolepsy, Hypophagia, and Obesity", *Neuron*(2001) 30:345-354.

Harris et al, "A role for lateral hypothalamic orexin neurons in reward seeking", *Nature* (2005) 437:556-559.

Harris et al, "Lateral hypothalamic orexin neurons are critically involved in learning to associate an environment with morphine reward", *Behavioural Brain Research* (2007) 183:43-51.

Hiebabecky et al, "Synthesis of novel azanorbornylpurine derivatives", *Tetrahedron* (2012) 68:1286-1298.

Hollander et al, "Insular hypocretin transmission regulates nicotine reward", *Proc Natl Acad Sci USA (PNAS)* (2008) 105(49) 19480-19485.

Johnson et al, "A key role for orexin in panic anxiety", *Nature Medicine* (2010) 16(1):111-116.

Johnson et al, "Activation of the Orexin I Receptor is a Critical Component of CO2-Medidated Anxiety and Hypertension but not Bradycardia", *Neuropsychopharmacology* (2012) 37:1911-1922.

Johnson et al, Chatper 9, "Orexin, stress, and anxiety/panic states", *Progress in Brain Research* (2012) vol. 198, A. Shekhar (Ed.), pp. 133-161.

Kapferer et al, "Electrophilic Bromination of N-Acylated Cyclohex-3-en-1-amines: Synthesis of 7-Azanorbornanes", *Helvetica Chimica Acta* (2004) 87:2764-2789.

Kirchgessner et al, "Orexin Synthesis and Response in the Gut", *Neuron* (1999) 24:941-951.

Kukkonen, "Physiology of the orexinergic/hypocretinergic system: a revisit in 2012", *American Journal of Physiol. Cell Physiol.* (2013) 304:C2-C32.

Langmead et al, "Characterisation of the binding of [3H]-SB-674042, a novel nonpeptide antagonist, to the human orexin-1 receptor", *British Journal of Pharmacology* (2004) 141:340-346.

Larsen et al, "Aza Diels-Alder Reactions in Aqueous Solution: Cyclocondensation of Dienes with Simple !minium Salts Generated under Mannich Conditions", *Journal American Chemistry Society* (1985) 107:1769-1771.

Lawrence et al, "The orexin system regulates alcohol-seeking in rats", *British Journal of Pharmacology* (2006) 148:752-759.

Leroy, "Preparation of 3-Bromopropiolic Esters: Methyl and tert-Butyl 3- Bromopropiolates (2-Propynoic acid, 3-bromo-, methyl and 1,1-dimethylethyl esters)", *Organic Syntheses*, Shinkai et al (Eds.) (1997) 74:212-216.

Lin et al, "The Sleep Disorder Canine Narcolepsy Is Caused by a Mutation in the Hypocretin (Orexin) Receptor 2 Gene", *Cell* (1999) 98:365-376.

Mahler et al, Chatper 7, "Multiple roles for orexin/hypocretin in addiction", *Progress in Brain Research* (2012) vol. 198, A. Shekhar (Ed.), pp. 79-121.

Malherbe et al, "Biochemical and behavioural characterization of EMPA, a novel high-affinity, selective antagonist for the OX2 receptor", *British Journal of Pharmacology* (2009) 156:1326-1341.

Marcus et al, "Differential Expression of Orexin Receptors 1 and 2 in the Rat Brain", *Journal of Comparative Neurology* (2001) 435:6-25.

Mignot et al, "Complex HLA-DR and -DQ Interactions Confer Risk of Narcolepsy-Cataplexy in Three Ethnic Groups", *American Journal Human Genetics* (2001) 68:686-699.

Mignot et al, "Narcolepsy and the HLA System", *New England Journal of Medicine* (2001) 344(9):692.

Nakamura et al, "Orexin-induced hyperlocomotion and stereotypy are mediated by the dopaminergic system", *Brain Research* (2000) 873:181-187.

Narita et al, "Direct Involvement of Orexinergic Systems in the Activation of the Mesolimbic Dopamine Pathway and Related Behaviros Induced by Morphine", *Journal of Neuroscience* (2006) 26(2):398-405.

Peyron et al, "Neurons Containing Hypocretin (Orexin) Project to Multiple Neuronal Systems", *Journal of Neuroscience* (1998) 18(23):9996-10015.

Peyron et al, "A mutation in a case of early onset narcolepsy and a generalized absence of hypocretin peptides in human narcoleptic brains", *Nature Medicine* (2000) 6(9):991-997.

Piper et al, "The novel brain neuropeptide, orexin-A, modulates the sleep-wake cycle of rats", *European Journal of Neuroscience* (2000) 12:726-730.

Sakurai et al, "Orexins and Orexin Receptors: A Family of Hyopthalamic Neuropeptides and G Protein-Coupled Receptors that Regulate Feeding Behavior", *Cell* (1998) 92:573-585.

Salomon et al, "Diurnal Variation of Cerebrospinal Fluid Hypocretin-1-(Orexin-A) Levels in Control and Depressed Subjects", *Biological Psychiatry* (2003) 54:96-104.

Samson et al, "Cardiovascular Regulatory Actions of the Hypocretins in Brain", *Brain Research* (1999) 831:248-253.

Sharf et al, "Orexin Mediates the Expression of Precipitated Morphine Withdrawal and Concurrent Activation of the Nucleus Accumbens Shell", *Biological Psychiatry* (2008) 64:175-183.

Shirasaka et al, "Sympathetic and cardiovascular actions of orexins in conscious rats", *American Journal of Physiol.(Regulatory Integrative Comp. Physiol.* 46) (1999) 277:R1780-R1785.

Shoblock et al, "Selective blockade of the orexin-2 receptor attenuates ethanol self-administration, place preference, and reinstatement", *Psychopharmacology* (2011) 215:191-203.

Singh et al, "Efficient Synthesis of (+)-N-BOC-exo-2-(methoxycarbonyl)-7-Azabicyclo[2.2.1]heptane, A Versatile Intermediate for the Synthesis of Epibatidine and Epiboxidine", *Tetrahedron Letters* (1997) 38(39):6829-6830.

Strawn et al, "Low cerebrospinal fluid and plasma orexin-A (hypocretin-1) concentrations in combat-related posttraumatic stress disorder", *Psychoneuroendocrinology* (2010) 35:1001-1007.

Takahashi et al, "Stimulation of Gastric Acid Secretion by Centrally Administered Orexin-A in Conscious Rats", *Biochemical and Biophysical Research Communications* (1999) 254:623-627.

Trivedi et al, "Distribution of orexin receptor mRNA in the rat brain", *FEBS Letters* (1998) 438:71-75.

Van Den Pol, "Hypothalamic Hypocretin (Orexin): Robust Innervation of the Spinal Cord", *Journal of Neuroscience* (1999) 19(8):3171-3182.

Walker et al, "Design, synthesis, structure-activity relationship, and in vivo activity of azabicyclic aryl amides as α7 nicotinic acetylcholine receptor agonists", *Bioorganic & Medicinal Chemistry* (2006) 14:8219-8248.

Yamanaka et al, "Orexins Activate Histaminergic Neurons via the Orexin 2 Receptor", *Biochemical and Biophysical Research Communications* (2002) 290:1237-1245.

International Search Report for corresponding International application PCT/US2014/024293 mailed May 22, 2014.

U.S. Appl. No. 14/851,909, Shireman et al.

Aissaoui et al., "N-Glycine-sulfonamides as potent dual orexin 1/orexin 2 receptor antagonists", Bioorganic & Medicinal Chemistry Letters, Nov. 2008, 18, 5729-5733.

(56) References Cited

OTHER PUBLICATIONS

Baxter et al., "The First Large-Scale Synthesis of MK-4305: A Dual Orexin Receptor Antagonist for the Treatment of Sleep Disorder", Organic Process Research & Development, Mar. 2011, 15, 367-375.

Bergman et al., "Proline bis-amides as potent dual orexin receptor antagonists", Bioorganic & Medicinal Chemistry Letters, Feb. 2008, 18, 1425-1430.

Betschart et al., "Identification of a Novel Series of Orexin Receptor Antagonists with a Distinct Effect on Sleep Architecture for the Treatment of Insomnia", Journal of Medicinal Chemistry, Oct. 2013, 56, 7590-7607.

Bettica et al., "Phase I studies on the safety, tolerability, pharmacokinetics and pharmacodynamics of SB-649868, a novel dual orexin receptor antagonist", Journal of Psychopharmacology, Aug. 2012, 26(8), 1058-1070.

Bettica et al., "The Orexin Antagonist SB-649868 Promotes and Maintains Sleep in Men with Primary Insomnia", SLEEP, Aug. 2012, 35(8), 1097-1104.

Brisbare-Roch et al., "Promotion of sleep by targeting the orexin system in rats, dogs and humans", Nature Medicine, Feb. 2007, 13(2), 150-155.

Coleman et al., "Design and synthesis of conformationally constrained N,N-disubstituted 1,4-diazepanes as potent orexin receptor antagonists", Bioorganic & Medicinal Chemistry Letters, Apr. 2010, 20, 2311-2315.

Coleman et al., "Discovery of [(2R,5R)-5-{[(5-Fluoropyridin-2-yl)oxy]methyl}- 2methylpiperidin-1-yl][5-methyl-2-(pyrimidin-2-yl)phenyl]methanone (Mk-6096): A Dual Orexin Receptor Antagonist with Potent Sleep-Promoting Properties", Chem Med Chem, Mar. 2012, 7, 415-424.

Coleman et al., "Discovery of 3,9-diazabicyclo[4.2.1]nonanes as potent dual orexin receptor antagonists with sleep-promoting activity in the rat", Bioorganic & Medicinal Chemistry Letters, Jul. 2010, 20, 4201-4205.

Cox et al., "Conformational analysis of N,N-disubstituted-1,4-diazepane orexin receptor antagonists and implications for receptor binding", Bioorganic & Medicinal Chemistry Letters, Jun. 2009, 19, 2997-3001.

Cox et al., "Discovery of the Dual Orexin Receptor Antagonist [(7R)-4-(5-Chloro-1,3- benzoxazol-2-yl)-7-methyl-1,4-diazepan-1-yl][5-methyl-2-(2H-1,2,3-triazol-2- yl)phenyl]methanone (MK-4305) for the Treatment of Insomnia", Journal of Medicinal Chemistry, Jul. 2010, 53, 5320-5332.

De Lecea et al., "The hypocretins: Hypothalamus-specific peptides with neuroexcitatory activity", Proc. Natl. Acad. Sci., Jan. 1998, 95, 322-327.

DiFabio et al., "Discovery process and pharmacological characterization of a novel dual orexin 1 and orexin 2 receptor antagonist useful for treatment of sleep disorders", Bioorganic & Medicinal Chemistry Letters, Sep. 2011, 21, 5562-5567.

Dugovic et al., "Blockade of Orexin-1 Receptors Attenuates Orexin-2 Receptor Antagonism-Induced Sleep Promotion in the Rat", The Journal of Pharmacology and Experimental Therapeutics, Jul. 2009, 330(1), 142-151.

Dugovic et al., "Orexin-1 receptor blockade dysregulates Rem sleep in the presence of orexin-2 receptor antagonism", Frontiers in Neuroscience, Feb. 2014, vol. 8, Article 29, 1-8.

Fujimoto et al., "Discovery of potent, selective, orally active benzoxazepine-based Orexin-2 receptor antagonists", Bioorganic & Medicinal Chemistry Letters, Nov. 2011, 21, 64146416.

Fujimoto et al., "Discovery of spiropiperidine-based potent and selective Orexin-2 receptor antagonists", Nov. 2011, 21, 6409-6413.

Gatfield et al., "Orexin Receptor Antagonists: A New Concept in CNS Disorders?", Chem Med Chem, Aug. 2010, 5, 1197-1214.

Girardin et al., "Convergent Kilogram-Scale Synthesis of Dual Orexin Receptor Antagonist", Organic Process Research & Development, Jan. 2013, 17, 61-68.

Gotter et al., "International Union of Basic and Clinical Pharmacology. LXXXVI. Orexin Receptor Function, Nomenclature and Pharmacology", Pharmacological Reviews, Jul. 2012, 64(3), 389-420.

Gotter et al., "Orexin receptors as therapeutic drug targets", Progress in Brain Research, 2012, 198, 163-188.

Gozzi et al., "Functional Magnetic Resonance Imaging Reveals Different Neural Substrates for the Effects of Orexin-1 and Orexin-2 Receptor Antagonists", PLoS ONE, Jan. 2011, 6(1), e16406, 12 pages.

Hirose et al., "N-Acyl 6,7-Dimethoxy-1,2,3,4-tetrahydroisoquinoline: The First Orexin-2 Receptor Selective Non-peptidic Antagonist", Bioorganic & Medicinal Chemistry Letters, Dec. 2003, 13, 4497-4499.

Jiang et al., "Disubstituted piperidines as potent orexin (hypocretin) receptor antagonists", Bioorganic & Medicinal Chemistry Letters, Jun. 2012, 22, 3890-3894.

Kuduk et al., "Synthesis and evaluation of carbon-linked analogs of dual orexin receptor antagonist filorexant", Bioorganic & Medicinal Chemistry Letters, Apr. 2014, 24, 1784-1789.

Lebold et al., "Selective orexin receptor antagonists", Bioorganic & Medicinal Chemistry Letters, Sep. 2013, 23, 4761-4769.

Mang et al., "The Dual Orexin Receptor Antagonist Almorexant Induces Sleep and Decreases Orexin-Induced Locomotion by Blocking Orexin 2 Receptors", SLEEP, Dec. 2012, 35(12), 1625-1635.

McAtee et al., "Novel substituted 4-phenyl-[1,3]dioxanes: potent and selective orexin receptor 2 (OX2R) antagonists", Bioorganic & Medicinal Chemistry Letters, Aug. 2004, 14, 4225-4229.

McElhinny Jr. et al., "Hydrolytic instability of the important orexin 1 receptor antagonist SB-334867: Possible confounding effects on in vivo and in vitro studies", Bioorganic & Medicinal Chemistry Letters, Nov. 2012, 22, 6661-6664.

Mercer et al., "Discovery of 2,5-diarylnicotinamides as selective orexin-2 receptor antagonists (2-SORAs)", Bioorganic & Medicinal Chemistry Letters, Dec. 2013, 23, 6620-6624.

Micheli et al., "2-Methyl-3-furanyl-4H-1,2,4-triazol-3-ylthioamides: a new class of selective orexin 2 antagonists", Bioorganic & Medicinal Chemistry Letters, Nov. 2010, 20, 6405-6407.

Michelson et al., "Safety and efficacy of suvorexant during 1-year treatment of insomnia with subsequent abrupt treatment discontinuation: a phase 3 randomised, double-blind, placebo-controlled trial", The Lancet, May 2014, 13, 461-471.

Nambu et al., "Distribution of orexin neurons in the adult rat brain", Brain Research, May 1999, 827, 243-260.

Oi et al., "Synthesis and Evaluation of Novel Radioligands for Positron Emission Tomography Imaging of the Orexin-2 Receptor", Journal of Medicinal Chemistry, Jul. 2013, 56, 6371-6385.

Perrey et al., "Diaryl urea analogues of SB-334867 as orexin-1 receptor antagonists", Bioorganic & Medicinal Chemistry Letters, May 2011, 21, 2980-2985.

Perrey et al., "Substituted Tetrahydroisoquinolines as Selective Antagonists for the Orexin 1 Receptor", Journal of Medicinal Chemistry, Sep. 2013, 56, 6901-6916.

Porter et al., "1,3-Biarylureas as Selective Non-peptide Antagonists of the Orexin-1 Receptor", Bioorganic & Medicinal Chemistry Letters, Jul. 2001, 11, 1907-1910.

Renzulli et al., "Disposition and Metabolism of [14C]Sb-649868, an Orexin 1 and 2 Receptor Antagonist, in Humans", Drug Metabolism and Disposition, 2011, 39(2), 215-227.

Roecker et al., "Discovery of 5"-Chloro-N-[(5,6-dimethoxypyridin-2-yl)methyl]-2,2':5',3"- terpyridine-3'-carboxamide (Mk-1064): A Selective Orexin 2 Receptor Antagonist (2-Sora) for the Treatment of Insomnia", Chem Med Chem, Feb. 2014, 9, 311-322.

Sakurai, "The neural circuit of orexin (hypocretin): maintaining sleep and wakefulness", Nature Reviews, Mar. 2007, 8, 171-181.

Sifferlen et al., "Discovery of substituted lactams as novel dual orexin receptor antagonists. Synthesis, preliminary structure-activity relationship studies and efforts towards improved metabolic stability and pharmacokinetic properties. Part 1", Bioorganic & Medicinal Chemistry Letters, 24, Feb. 2014, 1201-1208.

(56) References Cited

OTHER PUBLICATIONS

Sifferlen et al., "Novel pyrazolo-tetrahydropyridines as potent orexin receptor antagonists", Bioorganic & Medicinal Chemistry Letters, Mar. 2010, 20, 1539-1542.

Sifferlen et al., "Structure-activity relationship studies and sleep-promoting activity of novel 1-chloro-5,6,7,8-tetrahydroimidazo[1,5-a]pyrazine derivatives as dual orexin receptor antagonists. Part 2", Bioorganic & Medicinal Chemistry Letters, Jul. 2013, 23, 3857-3863.

Sifferlen et al., "Synthesis, structure-activity relationship studies, and identification of novel 5,6,7,8-tetrahydroimidazo[1,5-a]pyrazine derivatives as dual orexin receptor antagonists. Part 1", Bioorganic & Medicinal Chemistry Letters, Apr. 2013, 23, 2212-2216.

Smart et al., "SB-334867-A: the first selective orexin-1 receptor antagonist", British Journal of Pharmacology, Mar. 2001, 132, 1179-1182.

Stasi et al., "Discovery, synthesis, selectivity modulation and DMPK characterization of 5-azaspiro[2.4]heptanes as potent orexin receptor antagonists", Bioorganic & Medicinal Chemistry Letters, May 2013, 23, 2653-2658.

Steiner et al. "Discovery and Characterization of ACT-335827, an Orally Available, Brain Penetrant Orexin Receptor Type 1 Selective Antagonist", Chem Med Chem, Jun. 2013, 8, 898-903.

Steiner et al., "The brain orexin system and almorexant in fear-conditioned startle reactions in the rat", Psychopharmacology, Oct. 2012, 223, 465-475.

Whitman et al., "Discovery of a Potent, Cns-Penetrant Orexin Receptor Antagonist Based on an N,N-Disubstituted-1,4-diazepane Scaffold that Promotes Sleep in Rats", Chem Med Chem, Jul. 2009, 4, 1069-1074.

Winrow et al., "Discovery and development of orexin receptor antagonists as therapeutics for insomnia", British Journal of Pharmacology, Jan. 2014, 171, 283-293.

SUBSTITUTED 2-AZABICYCLES AND THEIR USE AS OREXIN RECEPTOR MODULATORS

CROSS REFERENCE TO RELATED APPLICATIONS

This application is a divisional of pending U.S. Application No. 14/206,722, filed Mar. 12, 2014, which claims priority to U.S. Provisional Application No. 61/780,378, filed Mar. 13, 2013, the entire disclosures of which are incorporated herein by reference in their entirety.

TECHNICAL FIELD

The present invention is directed to substituted 2-azabicyclic compounds, pharmaceutical compositions comprising them, methods of making them, and methods of using them for the modulation of the orexin receptor for the treatment of disease states, disorders, and conditions mediated by orexin receptor activity.

BACKGROUND

Orexin/hypocretin signaling is mediated by two receptors and two peptide agonists. The peptides (orexin-A and orexin-B) are cleavage products of the same gene, pre-pro orexin. In the central nervous system, neurons producing pre-pro orexin are found solely in the perifornical nucleus, the dorsal hypothalamus, and the lateral hypothalamus (Peyron et al., 1998, *J. Neurosci.* 18: 9996-10015). Orexigenic cells in these regions project to many areas of the brain, extending rostrally to the olfactory bulbs and caudally to the spinal cord (Van den Pol, 1999, *J. Neurosci.* 19: 3171-3182).

The orexins bind to two high affinity receptors, referred to as orexin-1 and orexin-2 receptors. Orexin-1 and orexin-2 receptors are G-protein-coupled, seven transmembrane receptors that share over 64% amino acid sequence identity with one another. Both receptors are generally excitatory, the common cellular response to orexin-induced receptor activation being increases in intracellular calcium. Homology between the species orthologs is high and there are no known pharmacological differences. Orexin-A and -B are usually considered equal ligands for orexin-2 receptor but orexin-B is thought to be 5- to 100-fold weaker ligand than orexin-A at the orexin-1 receptor (Sakurai et al., 1998, *Cell* 92: 573-585; Ammoun et al., 2003, *J. Pharmacol. Exp. Ther.* 305: 507-514).

Many regions of the brain have fairly selective expression of the orexin-1 or orexin-2 receptors (Marcus et al., 2001, *J. Comp Neurology* 435, 6-25; Trivedi et al., 1998, *FEBS Letters*, 438, 71-75). Orexin-1 receptors are selective for the limbic system (bed nucleus of the stria terminalis and amygdala), cingulate cortex and noradrenergic neurons in the locus coeruleus. Conversely, the orexin-2 receptor is almost the exclusive orexin receptor in the histaminergic neurons in the tuberomammilary nucleus which play a critical role in wake promotion; in paraventricular neurons and the parabrachial nucleus. In other brain regions like the dorsal raphe, the ventral tegmental area or the prefontal cortex both receptors are coexpressed.

The broad CNS distribution of cells producing orexin, as well as cells expressing the orexin receptors, suggests involvement of orexin in a number of physiological functions, including feeding and metabolism, regulation of wakefulness and sleep, sympathetic activation and stress response (de Lecea, 2012, *Progress in Brain Research*, 198, 15-24; Kukkonen, 2013, *Am J. Physiol. Cell Physiol.*, 304, C2-C32). Orexin also plays a key role regulating motivation and reward associated with food intake and with drugs of abuse (Mahler et al., 2012, *Progress in Brain Research*, 198, 79-121).

Several lines of evidence indicate that the orexin system is an important modulator of arousal. Rodents administered orexin intracerebroventricularly spend more time awake (Piper et al., 2000, *J. Neurosci.* 12: 726-730. Orexin-mediated effects on arousal have been linked to orexin neuronal projections to histaminergic neurons in the tuberomammillary nucleus (Yamanaka et al., 2002, *Biochem. Biophys. Res. Comm.* 290: 1237-1245). Rodents whose pre-pro orexin gene has been knocked out, or whose orexigenic neurons have been killed, display altered sleep/wake cycles similar to narcolepsy (Chemelli et al., 1999, *Cell* 98: 437-451; Hara et al., 2001, *Neuron* 30: 345-354). Dog models of narcolepsy have been shown to have mutant or non-functional orexin-2 receptors (Lin et al., 1999, *Cell* 98: 365-376). Orexin signaling as a target for sleep-promoting therapies was further validated clinically by findings of attenuated orexin levels and loss of orexinergic neurons in human narcoleptic patients (Mignot et al., 2001, *Am. J. Hum. Genet.* 68: 686-699; Minot & Thorsby, 2001, *New England J. Med.* 344: 692) or, in rare cases, to mutations in the orexin-2 gene (Peyron et al., 2000, *Nature Med.* 6: 991-997). Disorders of the sleep-wake cycle are therefore likely targets for orexin-2 receptor modulator activity. Examples of sleep-wake disorders that may be treated by agonists or other modulators that up-regulate orexin-2 receptor-mediated processes include narcolepsy, jet lag (sleepiness) and sleep disorders secondary to neurological disorders such as depression. Examples of disorders that may be treated by antagonists or other modulators that down-regulate orexin-2 receptor-mediated processes include insomnia, restless leg syndrome, jet lag (wakefulness) and sleep disorders secondary to neurological disorders such as mania, schizophrenia, pain syndromes and the like.

Evidence has accumulated to demonstrate a clear involvement of orexin signaling in reward pathways associated with drug dependence (Mahler et al., 2012, *Progress in Brain Research*, 198, 79-121). Orexinergic neurons send projections to the ventral tegmental area and other brain regions involved in reward processing. Orexin ligands mediate reward behavior, and antagonizing these effects with a selective orexin-1 receptor antagonist in various preclinical model of addiction has suggested that these actions are mediated through orexin-1 receptor. Specifically, a selective orexin-1 antagonist attenuates morphine conditioned place preference and reinstatement (Harris et al., 2005, *Nature*, 437, 556-5599; Narita et al., 2006, *J Neurosci.*, 26, 398-405; Harris et al., 2007, *Behav Brain Res*, 183, 43-51), stress-induced cocaine reinstatement, cocaine-induced behavioral and synaptic plasticity (Borgland et al., 2006, *Neuron*, 49, 589-601), and intake and cue and stress-induced reinstatement of ethanol (Lawrence et al., 2006, *Br J Pharmacol*, 148, 752-759), in addition to attenuating precipitated morphine withdrawal (Sharf et al., 2008, *Biol Psychiatry*, 64, 175-183) and nicotine self-administration (Hollander et al., 2008, *Proc Natl Acad Sci USA.*, 105, 19480-19485). Another recent study has also suggested a role for OX2R (Shoblock et al., 2011, *Psychopharmacology*, 215, 191-203).

Orexin's role in more complex emotional behavior is also emerging (Johnson et al., 2012, *Progress in Brain Research*, 198, 133-161). Changes in orexin levels in patients with panic and posttraumatic stress disorders have been noted as have changes in the prevalence of anxiety behaviors in narcoleptic patients (Johnson et al., 2010, *Nature Medicine*, 16, 111-115; Fortuyn et al., 2010, *General Hospital Psychiatry*, 32, 49-56; Strawn et al., 2010, *Psychoneuroendocrinology*, 35, 1001-1007). Lactate infusion or acute hypercapnia, which causes panic in humans, and are used as an animal model of panic, activates orexin neurons in the perifornical hypothalamus. This activation correlates with anxiety in the social interaction test or open field test. Blocking orexin signaling with either siRNA or selective orexin-1 receptor antagonists attenuates panic-like responses to lactate (Johnson et al., 2010, *Nature Medicine*, 16, 111-115; Johnson et al., 2012, *Neuropsychopharmacology*, 37, 1911, 1922).

Cerebral spinal fluid (CSF) levels of orexin are lower in depressed or suicidal patients, and the level of orexin inversely correlates with illness severity (Brundin et al., 2007, *European Neuropsychopharmacology*, 17, 573-579; Salomon et al., 2003, *Biol Psychiatry*, 54, 96-104). A positive correlation between orexin-1 receptor mRNA in the amygdala and depressive behavior in the forced swim test in mice has been reported (Arendt, 2013, *Behavioral Neuroscience*, 127, 86-94).

The orexin system also interacts with brain dopamine systems. Intracerebroventricular injections of orexin in mice increase locomotor activity, grooming and stereotypy; these behavioral effects are reversed by administration of D2 dopamine receptor antagonists (Nakamura et al., 2000, *Brain Res*. 873: 181-187). Therefore, orexin receptor modulators may be useful to treat various neurological disorders; e.g., agonists or up-regulators to treat catatonia, antagonists or down-regulators to treat Parkinson's disease, Tourette's syndrome, anxiety, delerium and dementias.

Orexins and their receptors have been found in both the myenteric and submucosal plexus of the enteric nervous system, where orexins have been shown to increase motility in vitro (Kirchgessner & Liu, 1999, *Neuron* 24: 941-951) and to stimulate gastric acid secretion in vitro (Takahashi et al., 1999, *Biochem. Biophys. Res. Comm*. 254: 623-627). Orexin effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux.

Body weight may also be affected by orexin-mediated regulation of appetite and metabolism. Some effects of orexin on metabolism and appetite may be mediated in the gut, where, as mentioned, orexins alter gastric motility and gastric acid secretion. Orexin antagonists therefore are likely to be useful in treatment of overweight or obesity and conditions related to overweight or obesity, such as insulin resistance/type II diabetes, hyperlipidemia, gallstones, angina, hypertension, breathlessness, tachycardia, infertility, sleep apnea, back and joint pain, varicose veins and osteoarthritis. Conversely, orexin agonists are likely to be useful in treatment of underweight and related conditions such as hypotension, bradycardia, ammenorrhea and related infertility, and eating disorders such as anorexia and bulimia.

Intracerebroventricularly administered orexins have been shown to increase mean arterial pressure and heart rate in freely moving (awake) animals (Samson et al., 1999, *Brain Res*. 831: 248-253; Shirasaka et al., 1999, *Am. J. Physiol*. 277: R1780-R1785) and in urethane-anesthetized animals (Chen et al., 2000, *Am. J. Physiol*. 278: R692-R697), with similar results. Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor modulators, will be of great advantage in the development of therapeutic agents for the treatment of a wide variety of disorders that are mediated through these receptor systems.

SUMMARY

The present invention is directed to compounds of Formula I:

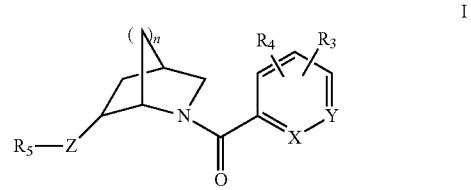

wherein X is N or CR$_1$; Y is N or CR$_2$; R$_1$ is H, alkoxy, halo, triazolyl, pyrimidinyl, oxazolyl, isoxazolyl, oxadiazolyl, or pyrazolyl; R$_2$ is H, alkyl, alkoxy, or halo; Z is NH or O; R$_3$ is H, alkyl, alkoxy, halo, or triazolyl; R$_4$ is H or alkyl; or R$_3$ and R$_4$, together with the atoms to which they are attached, form a 6-membered aryl ring or a 5-membered or 6-membered heteroaryl ring; R$_5$ is pyridyl, pyrazinyl, or pyrimidinyl, wherein the pyridyl, pyrazinyl, or pyrimidinyl is optionally substituted with halo or alkyl; and n is 1 or 2. Enantiomers and diastereomers of the compounds of Formula I are also described, as well as the pharmaceutically acceptable salts.

Methods of making the compounds of Formula I are also described. The invention also relates to pharmaceutical compositions comprising compounds of Formula I. Methods of using the compounds of the invention are also within the scope of the invention.

DETAILED DESCRIPTION OF ILLUSTRATIVE EMBODIMENTS

Figure 1:
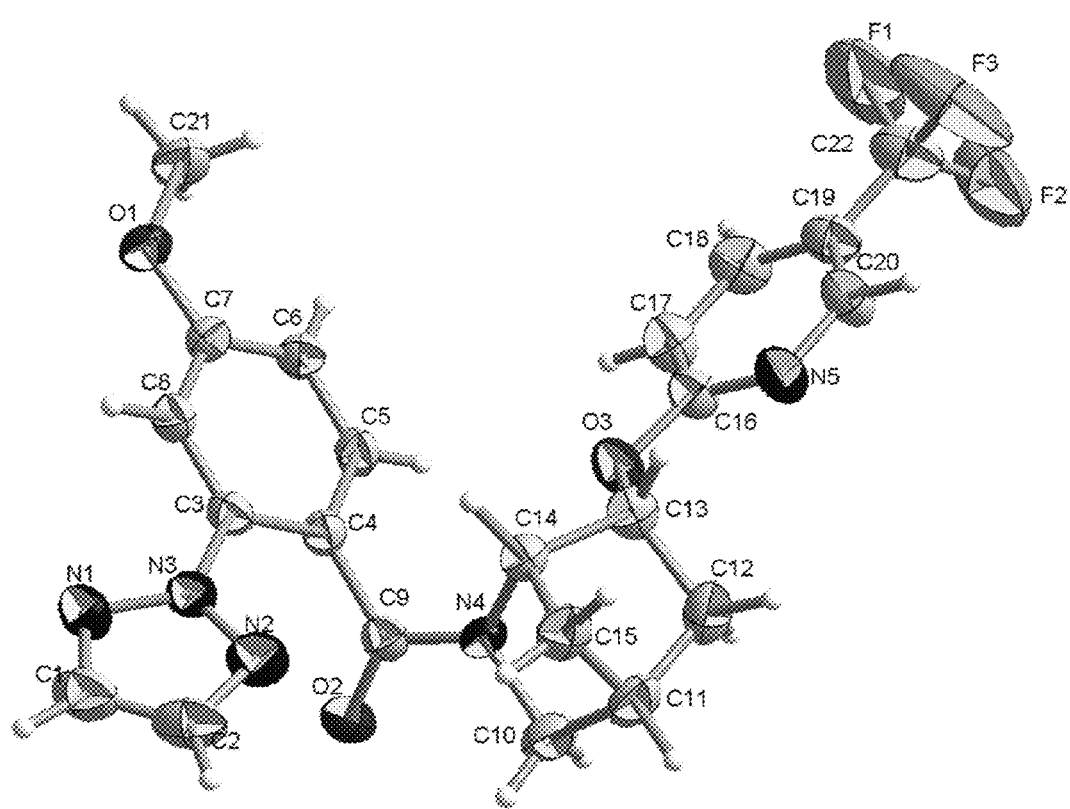
FIG. 1 depicts an Oak Ridge Thermal Ellipsoid Plot Program (ORTEP), shown at 40% probability level, of one embodiment of the invention, Example 13.

The invention may be more fully appreciated by reference to the following description, including the following glossary of terms and the concluding examples.

The term "alkyl" refers to a straight- or branched-chain alkyl group having from 1 to 12 carbon atoms in the chain. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups of the invention can be substituted with, for example, halogen atoms. One exemplary substitutent is fluoro. Preferred substituted alkyl groups of the invention include trihalogenated alkyl groups such as trifluoromethyl groups.

Alkyl groups of the invention can also refer to "cycloalkyl" moieties. Cycloalkyl refers to monocyclic, non-aromatic hydrocarbon groups having from 3 to 7 carbon atoms. Examples of cycloalkyl groups include, for example, cyclopropyl, cyclobutyl, cyclopentyl, cyclohexyl, 1-methylcyclopropyl, 2-methylcyclopentyl, and the like.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "aryl ring" represents" a mono- or bi-cyclic aromatic, hydrocarbon ring structure. Aryl rings can have 6 or 10 carbon atoms in the ring.

The term "halogen" represents chlorine, fluorine, bromine, or iodine. The term "halo" represents chloro, fluoro, bromo, or iodo.

The term "heteroaryl ring" represents a mono- or bicyclic aromoatic ring structure including carbon atoms as well as up to four heteroatoms selected from nitrogen, oxygen, and sulfur. Heteroaryl rings can include a total of 5, 6, 9, or 10 ring atoms.

The term "isoxazolyl" represents the following moiety:
The term "isoxazolyl" represents the following moiety:

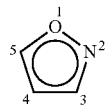

The isoxazolyl moiety can be attached through any one of the 3-, 4-, or 5-position carbon atoms. Isoxazolyl groups of the invention can be optionally substituted with, for example, one or two alkyl groups, for example, one or two methyl groups.

The term "oxazolyl" represents the following moiety:

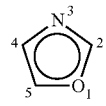

The oxazolyl moiety can be attached through any one of the carbon atoms.

The term "oxadiazolyl" represents a 1,2,3-oxadiazole, 1,2,4-oxadiazole, 1,2,5-oxadiazole, or 1,3,4-oxadiazole moiety:

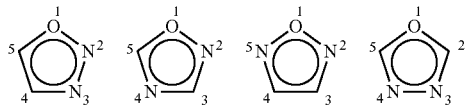

The oxadiazolyl moieties can be attached through any one of the carbon or nitrogen atoms. Within the scope of the invention, "oxadiazolyl" groups can be substituted with an alkyl group, preferably a methyl group.

The term "pyridyl" represents the following moiety:

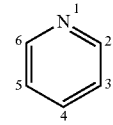

The pyridyl moiety can be attached through any one of the 2-, 3-, 4-, 5-, or 6-position carbon atoms.

The term "pyrimidinyl" represents the following moiety:

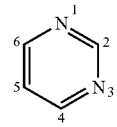

The pyrimidinyl moiety can be attached through any one of the 2-, 4-, 5-, or 6-position carbon atoms. Within the scope of the invention, "pyrimidinyl" groups of the invention can be substituted with halogen, for example fluoro.

The term "pyrazinyl" represents the following moiety:

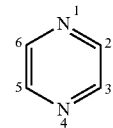

The pyrazinyl moiety can be attached through any one of the 2-, 3-, 5-, or 6-position carbon atoms.

The term "pyridazinyl" represents the following moiety:

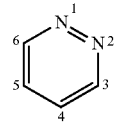

The pyridazinyl moiety can be attached through any one of the 3-, 4-, 5-, or 6-position carbon atoms.

The term "pyrazolyl" represents the following moiety:

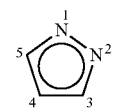

The pyrazolyl moiety can be attached through any one of the 1-, 2-, 3-, 4-, or 5-position carbon atoms. Pyrazolyl groups of the invention can be optionally substituted with, for example, one or two alkyl groups, for example, one or two methyl groups.

The term "triazolyl" represents a 1,2,3-triazole or a 1,2,4-triazole moiety:

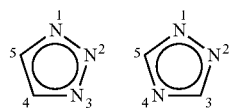

The triazolyl moieties can be attached through any one of their atoms.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present invention," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. Radiolabeled compounds of the invention can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, $^{13}$N and would be useful in Positron Emission Topography (PET) studies for examining substrate receptor occupancy.

All isotopic variants of the compounds of the invention, radioactive or not, are intended to be encompassed within the scope of the invention.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The present invention is directed to compounds of Formula I:

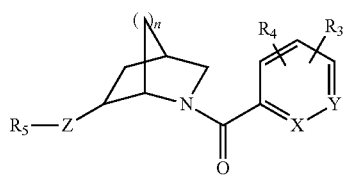

I wherein
X is N or $CR_1$
Y is N or $CR_2$
$R_1$ is H, alkoxy, halo, triazolyl, pyrimidinyl, oxazolyl, isoxazolyl, oxadiazolyl, or pyrazolyl;
$R_2$ is H, alkyl, alkoxy, or halo;
Z is NH or O;
$R_3$ is H, alkyl, alkoxy, halo, or triazolyl;
$R_4$ is H or alkyl;
  or $R_3$ and $R_4$, together with the atoms to which they are attached, form a 6-membered aryl ring or a 5- or 6-membered heteroaryl ring;
$R_5$ is pyridyl, pyrazinyl, or pyrimidinyl, wherein the pyridyl, pyrazinyl, or pyrimidinyl is optionally substituted with halo or alkyl; and
n is 1 or 2.

Enantiomers and diastereomers of the compounds of Formula I are also within the scope of the invention. Also within the scope of the invention are the pharmaceutically acceptable salts of the compounds of Formula I, as well as the pharmaceutically acceptable salts of the enantiomers and diastereomers of the compounds of Formula I.

In preferred embodiments, Z is NH. In other embodiments, Z is O.

In preferred embodiments, X is $CR_1$ and Y is $CR_2$.
In other embodiments, X is $CR_1$ and Y is N.
In yet other embodiments, X is N and Y is $CR_2$.
In those embodiments wherein X is $CR_1$, for example, where X is $CR_1$ and Y is $CR_2$ or X is $CR_1$ and Y is N, $R_1$ is H. In other embodiments, $R_1$ is alkoxy, for example, $C_{1-6}$alkoxy such as methoxy or ethoxy.

In those embodiments wherein X is $CR_1$, for example, where X is $CR_1$ and Y is $CR_2$ or X is $CR_1$ and Y is N, $R_1$ is halo, preferably F, Cl, or Br.

In those embodiments wherein X is $CR_1$, for example, where X is $CR_1$ and Y is $CR_2$ or X is $CR_1$ and Y is N, $R_1$ is triazolyl, with 1,2,3-triazolyl being preferred. In preferred embodiments, the 1,2,3-triazolyl is attached through the 2-position nitrogen atom. In other embodiments, the 1,2,3-triazolyl is attached through the 1-position nitrogen atom.

In those embodiments wherein X is $CR_1$, for example, where X is $CR_1$ and Y is $CR_2$ or X is $CR_1$ and Y is N, $R_1$ is pyrimidinyl, which can be attached through any available atom.

In those embodiments wherein X is $CR_1$, for example, where X is $CR_1$ and Y is $CR_2$ or X is $CR_1$ and Y is N, $R_1$ is oxazolyl, which can be attached through any available atom.

In those embodiments wherein X is $CR_1$, for example, where X is $CR_1$ and Y is $CR_2$ or X is $CR_1$ and Y is N, $R_1$ is isoxazolyl, which can be attached through any available atom.

In those embodiments wherein X is $CR_1$, for example, where X is $CR_1$ and Y is $CR_2$ or X is $CR_1$ and Y is N, $R_1$ is oxadiazolyl, which can be attached through any available atom. The oxadiazolyl group can optionally be substituted with alkyl, for example methyl. In exemplary embodiments, the substituted oxadiazolyl moiety is 1,2,4-oxadiazolyl substituted with methyl.

In those embodiments wherein X is $CR_1$, for example, where X is $CR_1$ and Y is $CR_2$ or X is $CR_1$ and Y is N, $R_1$ is pyrazolyl, which can be attached through any available atom. The pyrazolyl group can optionally be substituted with one or two $C_{1-6}$alkyl, for example methyl.

In preferred embodiments wherein Y is $CR_2$, for example, X is $CR_1$ and Y is $CR_2$ or X is N and Y is $CR_2$, $R_2$ is H. In other embodiments, $R_2$ is alkyl, for example $C_{1-6}$alkyl such as methyl.

In those embodiments wherein Y is $CR_2$, for example, X is $CR_1$ and Y is $CR_2$ or X is N and Y is $CR_2$, $R_2$ is alkoxy, for example, $C_{1-6}$alkoxy such as methoxy or ethoxy.

In those embodiments wherein Y is $CR_2$, for example, X is $CR_1$ and Y is $CR_2$ or X is N and Y is $CR_2$, $R_2$ is halo, preferably one of F, Cl, or Br.

In preferred embodiments, $R_3$ is H. In other embodiments, $R_3$ is alkyl, for example, $C_{1-6}$alkyl such as methyl.

In yet other embodiments, $R_3$ is alkoxy, for example, $C_{1-6}$alkoxy such as methoxy or ethoxy.

In still other embodiments, $R_3$ is halo, preferably F, Cl, or Br.

In other embodiments, $R_3$ is triazolyl, with 1,2,3-triazolyl being preferred. In preferred embodiments, the 1,2,3-triazolyl is attached through the 2-position nitrogen atom. In other embodiments, the 1,2,3-triazolyl is attached through the 1-position nitrogen atom.

In preferred embodiments, $R_4$ is H. In other embodiments, $R_3$ is alkyl, for example $C_{1-6}$alkyl such as methyl.

In alternative embodiments, $R_3$ and $R_4$, together with the atoms to which they are attached, form a 6-membered aryl ring.

In other embodiments, $R_3$ and $R_4$, together with the atoms to which they are attached, form a 5-membered heteroaryl ring. Preferably, the 5-membered heteroaryl ring includes one nitrogen atom.

In other embodiments, $R_3$ and $R_4$, together with the atoms to which they are attached, form a 6-membered heteroaryl ring. Preferably, the 6-membered heteroaryl ring includes one nitrogen atom.

In preferred embodiments, $R_5$ is pyridyl, which can be attached through any available atom, optionally substituted with halo (preferably F, Cl, or Br) or alkyl. In some embodiments, the alkyl is substituted with one or more halogen atoms. A preferred substituted alkyl group is trihaloalkyl such as trifluoromethyl. Preferably, $R_5$ is pyridyl substituted at any available position with trifluoromethyl.

In preferred embodiments, $R_5$ is pyrazinyl, which can be attached through any available atom, optionally substituted with halo (preferably F, Cl, or Br) or alkyl. In some embodiments, the alkyl is substituted with one or more halogen atoms. A preferred substituted alkyl group is trihaloalkyl such as trifluoromethyl. Preferably, $R_5$ is pyrazinyl substituted at any available position with trifluoromethyl.

In preferred embodiments, $R_5$ is pyrimidinyl, which can be attached through any available atom, optionally substituted with halo (preferably F, Cl, or Br) or alkyl. In some embodiments, the alkyl is substituted with one or more halogen atoms. A preferred substituted alkyl group is trihaloalkyl such as trifluoromethyl. Preferably, $R_5$ is pyrimidinyl substituted at any available position with trifluoromethyl.

In preferred embodiments, n is 1. In other embodiments, n is 2.

The invention relates to methods of using the compounds described herein to treat subjects diagnosed with or suffering from a disease, disorder, or condition mediated by orexin receptor activity. These methods are accomplished by administering to the subject a compound of the invention.

Diseases, disorders, and conditions mediated by orexin receptor activity include disorders of the sleep-wake cycle, insomnia, restless legs syndrome, jet-lag, disturbed sleep, sleep disorders secondary to neurological disorders, mania, depression, manic depression, schizophrenia, pain syndromes, fibromyalgia, neuropathic pain, catatonia, Parkinson's disease, Tourette's syndrome, anxiety, delirium, dementia, overweight, obesity, or conditions related to overweight or obesity, insulin resistance, type II diabetes, hyperlipidemia, gallstones, angina, hypertension, breathlessness, tachycardia, infertility, sleep apnea, back and joint pain, varicose veins, osteoarthritis, hypertension, tachycardia, arrhythmias, angina pectoris, acute heart failure, ulcers, irritable bowel syndrome, diarrhea gastroesophageal reflux, mood disorders, post-traumatic stress disorder, panic disorders, attention deficit disorders, cognitive deficiencies, or substance abuse.

Compounds of the invention are particularly suited for the treatment of mood disorders, post-traumatic stress disorder, panic disorders, attention deficit disorders, cognitive deficiencies, or substance abuse.

Sleep disorders include, but are not limited to, sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic).

Metabolic disorders include, but are not limited to, overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis.

Neurological disorders include, but are not limited to, Parkinson's disease, Alzheimer's disease, Tourette's Syndrome, catatonia, anxiety, delirium and dementias.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride.

Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000.mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

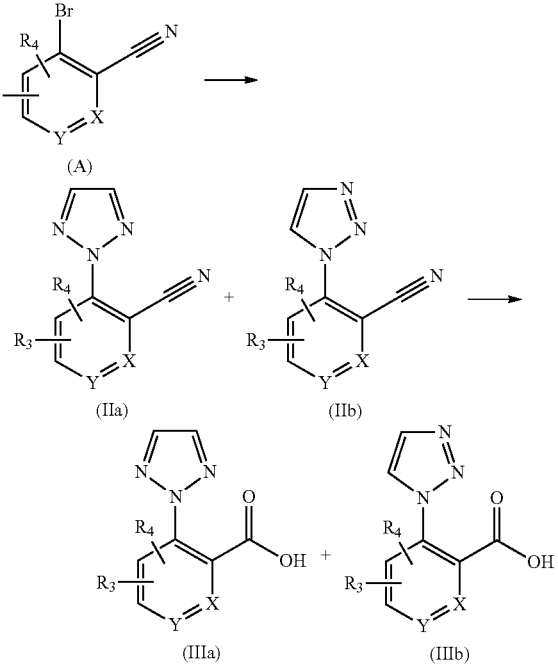

Scheme 1

Intermediate compounds of formula (IIIa) and (IIIb) can be prepared as outlined in Scheme 1 from commercially available or synthetically accessible compounds of formula (A) where $R_3$, $R_4$, X and Y are defined in formula (I) as above. Compounds of formula (IIa) and (IIb), are obtained by reacting a compound of formula (A), with commercially available 1,2,3-triazole, in the presence $K_2CO_3$ in DMF or dioxane, at temperatures ranging from about 60° C. to about 100° C. Compounds of formula (IIIa) and (IIIb) are obtained by reacting compounds of formula (II) in the presence of a base such as NaOH in a solvent such as EtOH at temperatures ranging from about 80° C. to about 100° C. One skilled in the art will recognize that 1,2,3-triazole can exist in two tautomeric forms defined as 2H-[1,2,3]triazole and 1H-[1,2,3]triazole thus accounting for the formation of (IIIa) and (IIIb).

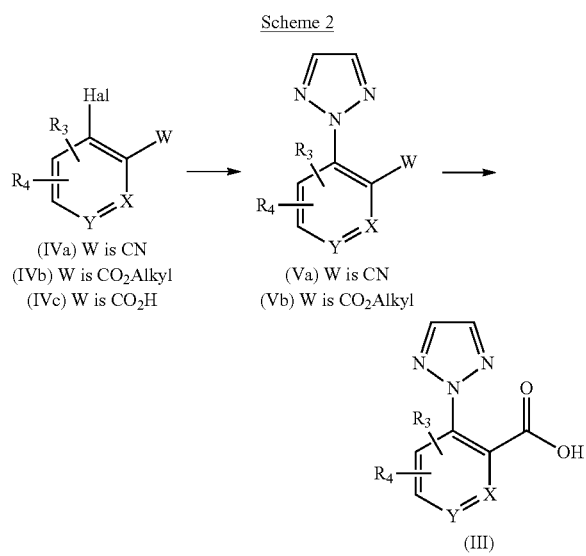

Intermediate compounds of formula (III) can be prepared as outlined in Scheme 2 from commercially available or synthetically accessible compounds of formula (IV$_{a-c}$). Compounds of formula (Va) and (Vb) are obtained by reacting compounds of formula (IVa), (IVb) and (IVc) where Hal is —Br, or —I; W is $CO_2H$, $CO_2Alkyl$, or CN and $R_3$ and $R_4$ are —H, halo, —$C_{1-4}$alkyl, —$C_{1-4}$alkoxy and $R_3$ and $R_4$ together with the atoms to which they are attached form a 6-membered aryl or 6 membered heteroaryl ring, with commercially available 1,2,3-triazole, in the presence of, for example, copper(I)iodide, $Cs_2CO_3$ and trans-N,N'-dimethyl-1,2-cyclohexanediamine in, for example, DMF or dioxane, at temperatures ranging from about 60° C. to about 120° C. Compounds of formula (IVc) can be converted to the corresponding esters (Vb) by treatment with, for example, alkyl iodide in the presence of a base such as $K_2CO_3$ in a solvent such as DMF. Compounds of formula (III) are obtained by reacting a compound of formula (Va) and (Vb) in the presence of a base such as NaOH in a solvent such as EtOH at temperatures ranging from about 80° C. to about 100° C. One skilled in the art will recognize that 1,2,3-triazole can exist in two tautomeric forms defined as 2H-[1,2,3]triazole and 1H-[1,2,3]triazole thus compounds of formula (Va), (Vb), and (III) can also exist as the N1 linked variant (structure not shown).

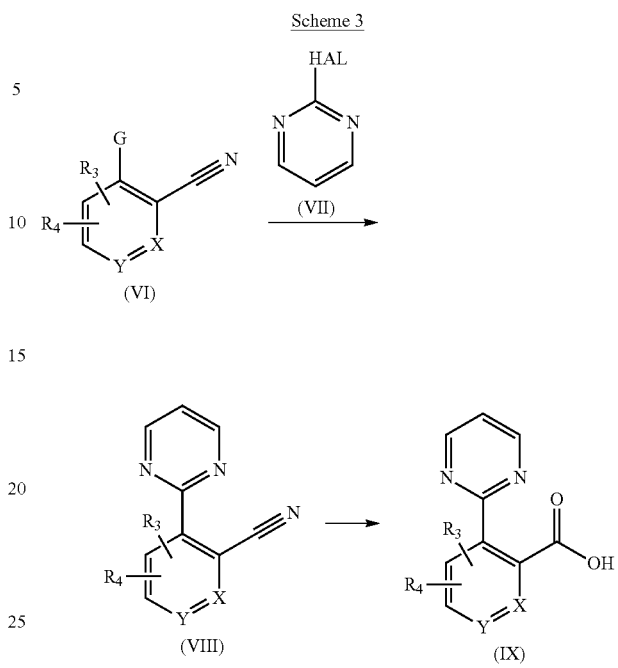

Intermediate compounds of formula (IX) can be prepared as outlined in Scheme 3 from commercially available or synthetically accessible compounds of formula (VI) where $R_3$, $R_4$, X and Y are defined in formula (I) as above, G is $SnBu_3$, or 4,4,5,5 tetramethyl-1,dioxaboralane, and HAL is Cl, or Br, preferably Br. Compounds of formula (VIII) are obtained by reacting a compound of formula (VI) with commercially available (VII) in the presence of a catalyst such as 1,1'-Bis(di-tert-butylphosphino)ferrocene palladium dichloride and a base such as $Na_2CO_3$ in a solvent such as 2-MeTHF or THF at temperatures ranging from about 60° C. to about 90° C. Compounds of formula (IX) are obtained by reacting a compound of formula (VIII) in the presence of a base such as NaOH in a solvent such as MeOH at temperatures ranging from about 80° C. to about 100° C. or acids such as $H_2SO_4$ in solvents such as $H_2O$ at temperatures ranging from about 80° C. to about 100° C.

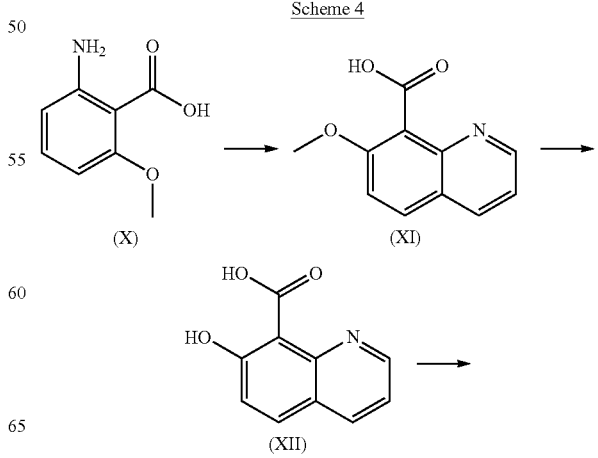

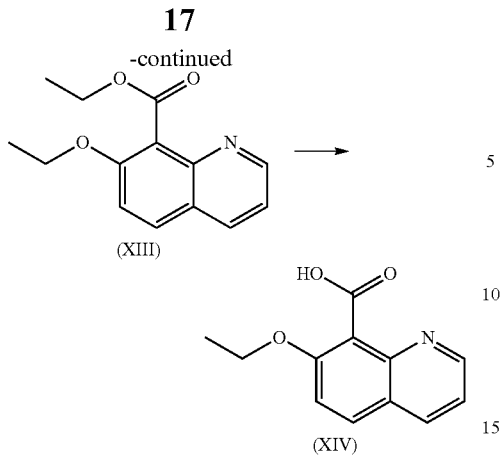

Intermediate compound of formula (XIV) can be prepared as outlined in Scheme 4 from commercially available compound (X). Compound (XI) is obtained by reacting compound (X) with commercially available acrolein in a solvent such as 1,4 dioxane at temperatures of about 200° C. in, for example, a microwave reactor. Compound (XII) can be prepared from compound (XI) by treatment with an acid such as HBr in a solvent such as toluene at a temperature of about about 90° C. Compound (XIII) can be obtained by treatment of compound (XII) with, for example, commercially available iodoethane and a base such as $K_2CO_3$ in a solvent such as DMF at temperatures ranging from about 45° C. to about 65° C. Compound (XIV) is obtained by treating compound (XIII) with a base such as NaOH in a solvent such as MeOH at temperatures ranging from about 80° C. to about 100° C.

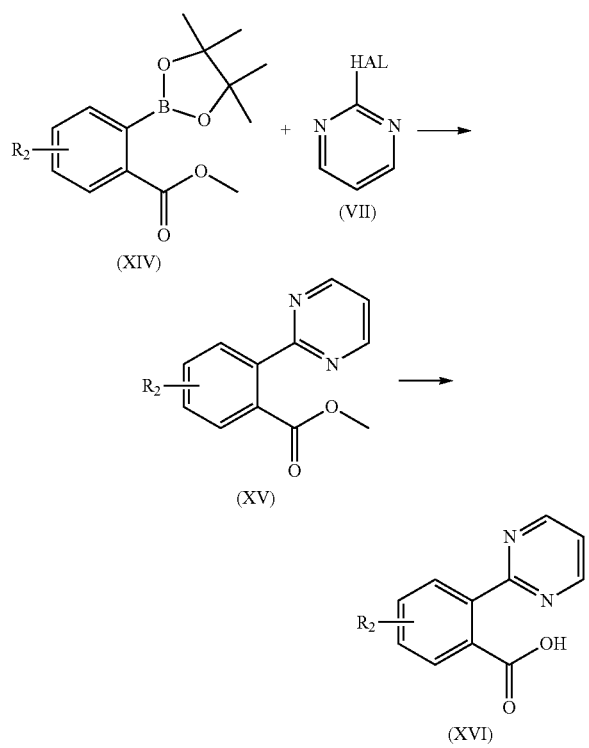

Intermediate compounds of formula (XVI) are prepared as outlined in Scheme 5 from commercially available or synthetically accessible compounds of formula (XIV) where $R_2$ is —H, —$C_{1-4}$alkyl, or —$C_{1-4}$alkoxy, and HAL is Cl, or Br. Compounds of formula (XV) are obtained by reacting a compound of formula (XIV) with commercially available (VII) in the presence of a catalyst such as Pd(dppf)Cl$_2$ and a base such as $Na_2CO_3$ in a solvent such as 2-MeTHF at temperatures ranging from about 75° C. to about 150° C. Compounds of formula (XVI) are obtained by reacting a compound of formula (XV) in the presence of a base such as NaOH in a solvent such as MeOH at temperatures ranging from about 80° C. to about 100° C.

Scheme 6

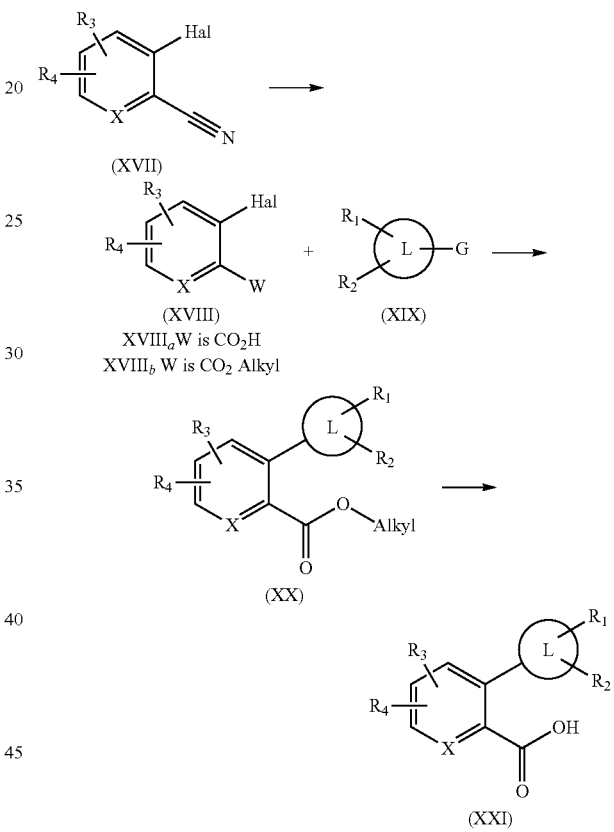

Intermediate compounds of formula (XXI) can be prepared as outlined in Scheme 6 from commercially available or synthetically accessible compounds of formula (XVII) where Hal is Br or I; and where $R_3$ and $R_4$ are —H, halo, —$C_{1-4}$alkyl, —$C_{1-4}$alkoxy. Compounds of formula (XVIIIa) can be converted to the corresponding ester (XVIIIb) by treatment with, for example, thionyl chloride in a solvent such as MeOH. Compounds of the formula (XX) are obtained by reacting compounds of formula (XVIIIb) with commercially available compounds of the formula XIX where L is a heterocycle such as pyrazole, pyridyl, or oxazole; G is SnBu$_3$ or 4,4,5,5 tetramethyl-1,dioxaboralane and $R_1$ and $R_2$ are —H, —$C_{1-4}$alkyl, or —$C_{1-4}$alkoxy in the presence of a catalyst such as Pd(Ph$_3$P)$_4$ and a base such as $Na_2CO_3$ in a mixture of solvents such as DME and $H_2O$ at temperatures ranging from about 100° C. to about 150° C. Compounds of formula (XXI) are obtained by reacting a compound of formula (XX) in the presence of a base such as NaOH in a solvent such as MeOH at temperatures ranging from about 80° C. to about 100° C.

install the hydroxyl group, and, for example, a one-pot palladium mediated hydrogenolysis using hydrogen gas (1

Scheme 7

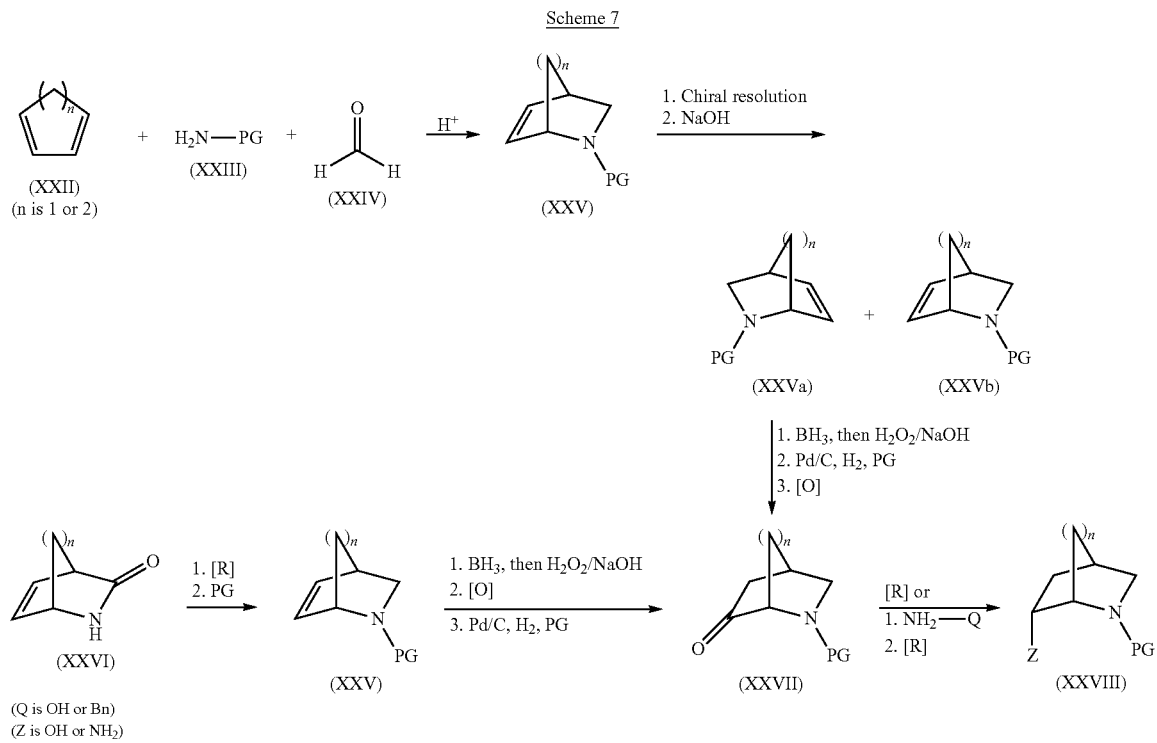

(Q is OH or Bn)
(Z is OH or NH₂)

According to Scheme 7, compound (XXV), where n is 1 or 2, is obtained by reaction of (XXII), (XXIII) where PG of H₂N-PG is H, benzyl (Bn), methyl benzyl, and the like, and (XXIV) in an aqueous medium where H⁺ is HCl, AcOH and the like as described in C. Chiu et al. *Synthetic Communications* 1996, 26, 577-584 and S. Larsen et al. *J. Am. Chem. Soc.* 1985, 107, 1768-1769. In a particularly preferred embodiment, a compound of formula (XXV), where n is 1, is obtained by reacting, for example, commercially available cyclopentadiene, (+)-α-methyl-benzylamine and formaldehyde in an aqueous medium with AcOH. Enantio-enriched compounds of formula (XXVa) and (XXVb) are obtained by chiral resolution of (XXV) using a chiral acid, such as commercially available L or D-dibenzoyl tartaric acid and the like, followed by formation of the free base using a base such as aqueous NaOH and the like, as described in C. Chiu et al. *Synthetic Communications* 1996, 26, 577-584. In a preferred embodiment, a compound of formula (XXV) is treated with, for example, D-dibenzoyl tartaric acid followed by a base such as aqueous NaOH to afford an enantio-enriched compound of formula (XXVa). Compound (XXVII) is obtained from (XXVa) through a hydroboration/oxidation sequence of the olefin to install the hydroxyl group; followed by, for example, an optional one-pot palladium-mediated hydrogenolysis and PG "swap" (i.e. methyl benzyl to Boc); and subsequent oxidation of the hydroxyl group using an oxidant such as IBX, SO₃-pyridine, Swern conditions [(COCl)₂, DMSO, Et₃N], and the like, in a solvent such as EtOAc, DMSO, DCM, and the like, at temperatures ranging from about −78° C. to room temperature (about 23° C.). In a preferred embodiment, a compound of formula (XXVa) where PG is methyl benzyl, is treated with, for example, BH₃ followed by H₂O₂ and NaOH to atm), Pd/C, and Boc₂O, in EtOH at room temperature (23° C.) exchanges the methyl benzyl for a Boc group. The Boc-protected intermediate is oxidized with, for example, IBX in refluxing such as, for example, EtOAc to afford a compound of formula (XXVII). Compound (XXVb) could also be subjected to the same set of transformations as compound (XXVa) to obtain the corresponding opposite enantiomer (structure not shown).

A compound of formula (XXVIII) where Z is OH, is obtained from reduction ([R]) of the ketone in a compound of formula (XXVII), with a reducing agent such as L-Selectride, NaBH₄ and the like, in a solvent such as THF, MeOH and the like at temperatures ranging from about −78° C. to room temperature (about 23° C.). Alternatively, the racemic form of a compound of formula (XXVIII) can be obtained from reduction of commercially available (R/S)-tert-butyl 6-oxo-2-azabicyclo[2.2.1]heptane-2-carboxylate as described in R. Nencka et al. *Tetrahedron* 2012, 68, 1286-1298.

An alternative route to a compound of formula (XXVII) can be prepared from commercially available (1S,4R)-2-azabicyclo[2.2.1]hept-5-en-3-one (XXVI). A compound of formula (XXV) is obtained from treatment of compound (XXVI) with a reducing agent such as LiAlH₄ and the like, followed by protection of the free amine with a suitable protecting group. A compound of formula (XXVII) is obtained from a compound of formula (XXV) by a hydroboration/oxidation sequence of the olefin to install the hydroxyl group; followed by oxidation of the hydroxyl group using an oxidant such as IBX, SO₃-pyridine, Swern conditions [(COCl)₂, DMSO, Et₃N], and the like, in a solvent such as EtOAc, DMSO, DCM, and the like at temperatures ranging from about −78° C. to room temperature (about 23° C.); and, optionally, a one-pot palladium mediated hydrogenolysis and PG "swap" (i.e. Bn to Boc). In a preferred embodiment, a compound of formula (XXV) where PG is Bn is subjected to the conditions described in F. Carroll et al. *J. of Med. Chem.* 1992, 35, 2184-2191, followed by PG swap (Bn to Boc) to obtain a compound of formula (XXVII) where PG is Boc.

A compound of formula (XXVIII) where Z is $NH_2$, is obtained by reacting a compound of formula (XXVII) with an amine $NH_2$-Q, where Q is OH or Bn, followed by reduction of the corresponding oxime or imine with a suitable reducing agent such as $NaBH_4$ (with or without a metal salt additive such as $NiCl_2$ and the like), Raney Ni ($H_2$ atm), $Zn(BH_4)_2$, and the like in a solvent such as MeOH and the like. In a particular embodiment, the oxime intermediate from reaction of a compound of formula (XXVII) with an amine $NH_2$-Q, where Q is OH, is obtained by reacting a compound of formula (XXVII) with commercially available hydroxylamine hydrochloride and triethylamine in EtOH at temperatures ranging from room temperature (about 23° C.) to reflux. The oxime intermediate is reduced with $NaBH_4$ in combination with $NiCl_2$ in MeOH to give a compound of formula (XXVIII) where Z is $NH_2$. Alternatively, the imine intermediate from reaction of a compound of formula (XXVII) with an amine $NH_2$-Q, where Q is Bn, is obtained by reacting a compound of formula (XXVII) with commercially available benzylamine. In-situ reduction of the imine intermediate with a reducing agent such as sodium triacetoxyborohydride and the like, followed by debenzylation under, for example, palladium mediated hydrogenolysis affords a compound of formula (XXVIII) where Z is $NH_2$.

Scheme 8

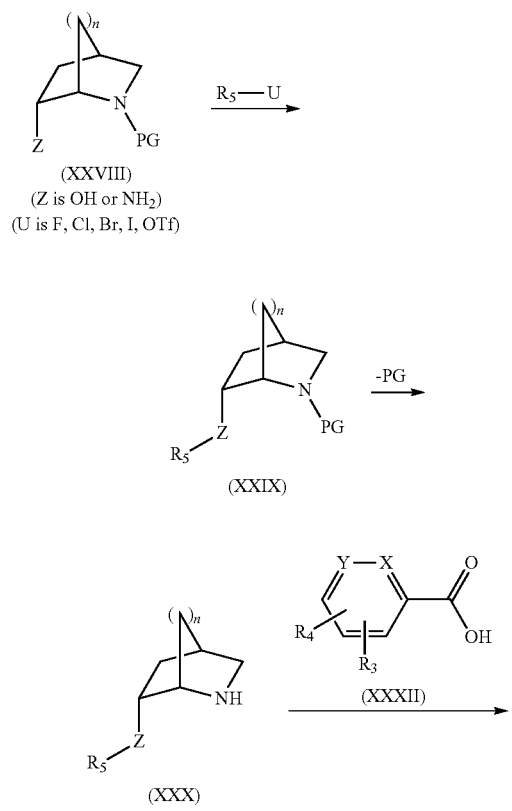

(XXVIII)
(Z is OH or $NH_2$)
(U is F, Cl, Br, I, OTf)

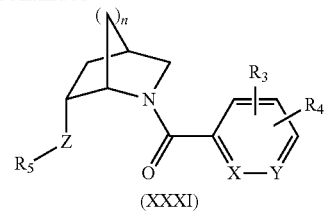

(XXXI)

According to Scheme 8, a compound of formula (XXIX), where Z is O or NH, is obtained from a compound of formula (XXVIII), by a $S_NAr$ reaction or metal mediated cross-coupling reaction with a compound $R_5$—U; where $R_5$—U is a suitable commercially available or synthetically accessible halogen-substituted heteroaryl compound, where $R_5$ is defined in formula (I) as above and W is F, Cl, Br, I, or OTf. A compound of formula (XXIX) where Z is O, is obtained from a compound of formula (XXVIII), where Z is OH, by $S_NAr$ coupling with a compound $R_5$—W as described above, in the presence of a base, such as NaH, $K_2CO_3$ and the like, in a solvent such as DMF at temperatures ranging from room temperature (about 23° C.) to about 90° C. In a preferred embodiment the base is NaH and the solvent is DMF. A compound of formula (XXIX), where Z is NH, is obtained from a compound of formula (XXVIII), where Z is $NH_2$, by metal mediated cross-coupling with a compound $R_5$—W as described above, in the presence of a palladium catalyst, a phosphine ligand such as BINAP and the like, a base such as NaOtBu and the like, in a solvent such as toluene, DME, and DMF, at temperatures ranging from room temperature (about 23° C.) to about 100° C. In a preferred embodiment the palladium catalyst is $Pd(OAc)_2$, the ligand is BINAP, the base is NaOtBu, and the solvent is toluene. Alternatively, a compound of formula (XXIX) where Z is NH, is obtained from a compound of formula (XXVIII), where Z is $NH_2$, by $S_NAr$ coupling with a compound $R_5$—W as described above, in the presence of a base, such as NaH, $K_2CO_3$ in a solvent such as DMF at temperatures ranging from room temperature (about 23° C.) to about 90° C. In a preferred embodiment the base is $K_2CO_3$ and the solvent is DMF. Removal of PG (where PG is Boc, Bn, methyl benzyl, and the like) in compounds of formula (XXIX) is accomplished using methods known to one skilled in the art to give compounds of formula (XXX). In a preferred embodiment, where PG is Boc in a compound of formula (XXIX) and Z is O or NH, is treated with, for example, HCl in dioxane to afford a compound of formula (XXX).

A compound of formula (XXXI) is obtained from a compound of formula (XXX), by reaction of a compound of formula (XXX) with a compound of formula (XXXII), under amide bond formation conditions. Compounds of formula (XXXII), where X, Y, $R_3$, and $R_4$ are as defined in formula (I), are commercially available, as described, or synthetically accessible appropriately substituted aryl or heteroaryl carboxylic acids or acid salts. A compound of formula (XXX), either as a free base or as an acid salt, is reacted with a compound of formula (XXXII) in the presence of a dehydrating agent such as HOBt/EDAC, CDI, HATU, HOAT, $T_3P$; a suitably selected base such as DIPEA, TEA; in an organic solvent or mixture thereof, such as toluene, MeCN, EtOAc, DMF, THF, DCM to afford a compound of formula (XXXI). In a particularly preferred embodiment a compound of formula (XXXI) is obtained using, for example, the dehydrating agent HATU, the base DIPEA, and the solvent DMF; or the dehydrating agent $T_3P$, the base $Et_3N$, and the solvent mixture of DCM/DMF. Alternatively, one skilled in the art can transform a compound of formula (XXXII) to the corresponding acid chloride or an activated ester before amide formation with a compound of formula (XXX).

EXAMPLES

Abbreviations:

| Term | Acronym |
|---|---|
| Acetic Acid | HOAc |
| Acetonitrile | ACN |
| Apparent | app |
| Aqueous | aq |
| Atmosphere | atm |
| 2-(1H-9-Azobenzotriazole-1-yl)-1,1,3,3-tetramethylaminium hexafluorophosphate | HATU |
| Benzyl | Bn |
| 2,2'-bis(diphenylphosphino)-1,1'-binaphthalene | BINAP |
| [1,1'-Bis(di-tert-butylphosphino)ferrocene]dichloropalladium(II) | $PdCl_2(dtbpf)$ |
| Broad | br |
| tert-Butylcarbamoyl | Boc/Boc |
| Dichloromethane | DCM |
| Diisopropylethylamine | DIPEA |
| 1,2-Dimethoxyethane | DME |
| N,N-Dimethylformamide | DMF |
| Dimethylsulfoxide | DMSO |
| Doublet | d |
| Electrospray ionization | ESI |
| Enantiomeric excess | ee |
| Ethanol | EtOH |
| Ethyl Acetate | EtOAc, or EA |
| Grams | g |
| Hertz | Hz |
| High-pressure liquid chromatography | HPLC |
| Hours | h |
| Liquid chromatography and mass spectrometry | LCMS |
| Mass spectrometry | MS |
| Mass to charge ratio | m/z |
| Methanol | MeOH |
| Microliter | μL |
| Milligrams | mg |
| Milliliter | mL |
| Millimoles | mmol |
| Minute | min |
| Molar | M |
| Multiplet | m |
| Normal | N |
| Nuclear magnetic resonance | NMR |
| Palladium on carbon | Pd/C |
| Palladium hydroxide on carbon | $Pd(OH)_2/C$ |
| Parts per million | ppm |
| Phenyl | Ph |
| Propylphosphonic anhydride | $T_3P$ |
| Retention time | $R_t$ |
| Room temperature | rt |
| Quartet | q |
| Singlet | s |
| Supercritical Fluid Chromatography | SFC |
| Temperature | T |
| Thin layer chromatography | TLC |
| Times | X |
| Triethylamine | TEA |
| Trifluoroacetic acid | TFA |
| Triplet | t |

Chemistry:

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Where compounds were "purified via silica gel chromatography" normal-phase flash column chromatography was performed on silica gel ($SiO_2$) using prepackaged cartridges, eluting with the indicated solvents.

Where compounds were purified by "Shimadzu Method X" the method employed was either:

Preparative reverse-phase high performance liquid chromatography (HPLC) was performed on a Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min. or Preparative reverse-phase high performance liquid chromatography (HPLC) was performed on a Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

Where compounds were purified by "Agilent Prep Method X" the method employed was either:

Preparative reverse-phase high performance liquid chromatography (HPLC) was performed on a Agilent 1100 Series HPLC with an XBridge C18 OBD column (5 μm, 30×100 mm), mobile phase of 5% ACN in 20 mM $NH_4OH$ was held for 2 min, then a gradient of 5-99% ACN over 15 min, then held at 99% ACN for 5 min, with a flow rate of 40 mL/min.

or

Preparative reverse-phase high performance liquid chromatography (HPLC) was performed on a Agilent 1100 Series HPLC with an XBridge C18 OBD column (5 μm, 50×100 mm), mobile phase of 5% ACN in 20 mM $NH_4OH$ was held for 2 min, then a gradient of 5-99% ACN over 15 min, then held at 99% ACN for 5 min, with a flow rate of 80 mL/min.

Mass spectra (MS) were obtained on an Agilent series 1100 MSD using electrospray ionization (ESI) in positive mode unless otherwise indicated. Calculated (calcd.) mass corresponds to the exact mass.

Where acids are employed for amide bond coupling the free acid or acid salt may be used interchangeably.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration). Definitions for multiplicity are as follows: s=singlet, d=doublet, t=triplet, q=quartet, m=multiplet, br=broad. For compounds that are present as a mixture of rotamers the ratio is represented so that the total is 1, e.g. 0.80:0.20. $^1H$ NMR data may be reported for only the major as indicated.

Chemical names were generated using ChemDraw Ultra 12.0 (CambridgeSoft Corp., Cambridge, Mass.) or ACD/Name Version 10.01 (Advanced Chemistry Development, Toronto, Ontario, Canada)

Compounds designated (R/S) are racemic compounds where the relative stereochemistry is as drawn.

INTERMEDIATES

| Intermediate | Name | Structure | Reference |
|---|---|---|---|
| A-1 | 2-(2H-1,2,3-triazol-2-yl)benzoic acid | 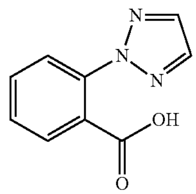 [SMILES: O=C(O)c1ccccc1-n1nccn1] | Prepared according to WO 2011/050198 Intermediate 2 |
| A-2 | 3-fluoro-2-(pyrimidin-2-yl)benzoic acid | 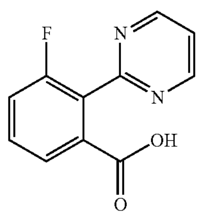 [SMILES: O=C(O)c1cccc(F)c1-c1ncccn1] | Prepared according to WO 2011/050198 Intermediate 50 |
| A-3 | 6-methyl-2-(2H-1,2,3-triazol-2-yl)nicotinic acid | 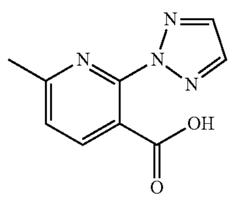 | Prepared according to WO 2011/050198 Intemediate 70 |
| A-4 | 6-methyl-2-(1H-1,2,3-triazol-1-yl)nicotinic acid | 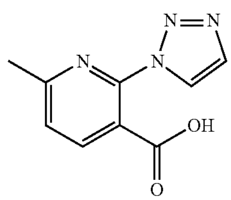 | Prepared according to WO 201//050198 Intermediate 71 |
| A-5 | 4-methoxy-2-(2H-1,2,3-triazol-2-yl)benzoic acid | 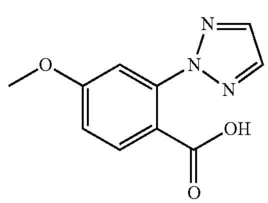 [SMILES: COc1ccc(C(=O)O)c(-n2nccn2)c1] | Prepared according to WO 2011/050198 Intermediate 54 |
| A-6 | 2-fluoro-6-(pyrimidin-2-yl)benzoic acid | 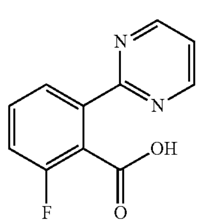 [SMILES: O=C(O)c1c(F)cccc1-c1ncccn1] | Prepared according to WO 2011/050198 Intermediate 14 |
| A-7 | 5-fluoro-2-(pyrimidin-2-yl)benzoic acid. | 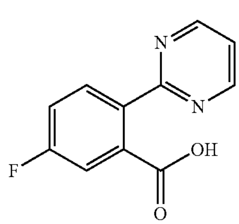 [SMILES: O=C(O)c1cc(F)ccc1-c1ncccn1] | Prepared according to WO 2011/050198 Intermediate 13 |

-continued

| Intermediate | Name | Structure | Reference |
|---|---|---|---|
| A-8 | 3-ethoxy-6-methylpicolinic acid | 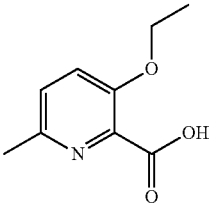 | WO 2010/063663 Description 39 |
| A-9 | 2-(4H-1,2,4-triazol-4-yl)benzoic acid | 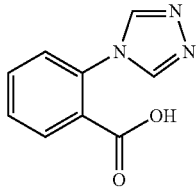 [SMILES: O=C(O)c1ccccc1-n1cnnc1] | Commercially available, CAS 167626-65-5 |
| A-10 | 5-fluoro-2-(2H-1,2,3-triazol-2-yl)benzoic acid | 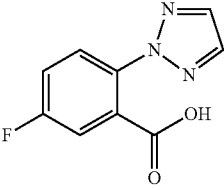 [SMILES: O=C(O)c1cc(F)ccc1-n1nccn1] | Prepared according to WO 2011/050198 Intermediate 1 |
| A-11 | 2-fluoro-6-(2H-1,2,3-triazol-2-yl)benzoic acid | 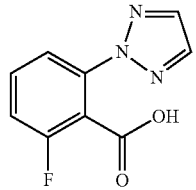 [SMILES: O=C(O)c1c(F)cccc1-n1nccn1] | Prepared according to WO 2011/050198 Intermediate 12 |
| A-12 | 4-fluoro-2-(2H-1,2,3-triazol-2-yl)benzoic acid | 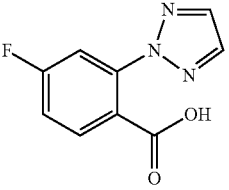 [SMILES: O=C(O)c1ccc(F)cc1-n1nccn1] | Prepared according to WO 2011/050198 Intermediate 4 |
| A-13 | 2-methoxy-6-(2H-1,2,3-triazol-2-yl(benzoic acid | 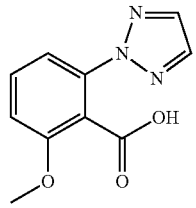 [SMILES: COc1cccc(-n2nccn2)c1C(=O)O] | Prepared analogous to Intermediate A-X using 2-bromo-6-(2H-1,2,3-triazol-2-yl)benzoic acid |
| A-15 | 4-methoxy-2-(pyrimidin-2-yl)benzoic acid | 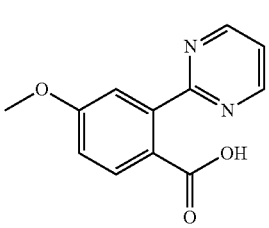 [SMILES: COc1ccc(C(=O)O)c(-c2ncccn2)c1] | Prepared according to WO 2011/050198 Intermediate 88 |

-continued

| Intermediate | Name | Structure | Reference |
|---|---|---|---|
| A-16 | 3-fluoro-2-(2H-1,2,3-triazol-2-yl)benzoic acid | 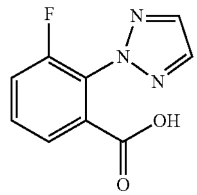 [SMILES: O=C(O)c1cccc(F)c1-n1nccn1] | Prepared according to WO 2011/050198 Intermediate 5 |
| A-18 | 3-fluoro-2-methoxybenzoic acid | 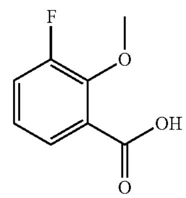 | Commercially available, CAS 106428-05-1 |

Synthesis of 3-fluoro-2-(pyrimidin-2-yl)benzonitrile
(Intermediate in the synthesis of intermediate A-2)

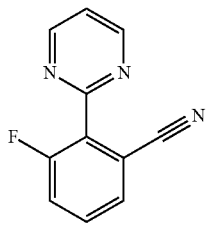 [SMILES: N#Cc1cccc(F)c1-c1ncccn1]

To a solution of 3-fluoro-2-(4,4,5,5-tetramethyl-1,3,2-dioxaborolan-2-yl)benzonitrile (4.98 g, 19.1 mmol) and 2-bromopyridine (3.85 g, 23 mmol) in THF (96 mL) was added Na$_2$CO$_3$ (6 g, 57.4 mmol) followed by water (43 mL). The reaction mixture was degassed with N$_2$ for 10 minutes. PdCl$_2$(dtbpf) (374 mg, 0.57 mmol) was added and the reaction mixture was stirred at 80° C. for 5 h. The solution was cooled to room temperature and a mixture of EtOAc and water was added. The aqueous was extracted twice with EtOAc and the combined organic layers were dried over MgSO4, filtered and evaporated. The title compound was precipitated by dissolving the residue in a minimum amount of EtOAc and then adding hexanes. The solid was filtered, washed with hexanes and dried to afford the title compound (2.46 g, 64%). MS (ESI) mass calcd. for C$_{11}$H$_6$FN$_3$, 199.1. m/z found 200.1 [M+H]$^+$. $^1$H NMR (400 MHz, Chloroform-d) δ 9.02-8.91 (m, 2H), 7.65 (dt, J=7.7, 1.0 Hz, 1H), 7.60-7.52 (m, 1H), 7.51-7.43 (m, 1H), 7.41 (t, J=4.9 Hz, 1H).

Intermediate A-19

5-methyl-3-(2H-1,2,3-triazol-2-yl)picolinic acid

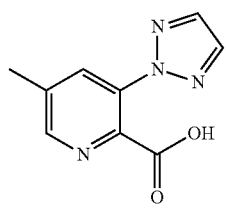

Step A: 5-methyl-3-(2H-1,2,3-triazol-2-yl)picolinonitrile. To 3-bromo-5-methylpicolinic acid (1.5 g, 7.6 mmol) in DMF (19 mL) was added K$_2$CO$_3$ (1.2 g, 8.4 mmol) and 2H-1,2,3-triazole (440 μL, 7.6 mmol). The mixture was heated to 100° C. for 16 h, cooled to room temperature and extracted with EtOAc (2x). The combined organics were dried (Na$_2$SO$_4$) and concentrated. Purification via silica gel chromatography (5-60% EtOAc in hexanes) gave the title compound (490 mg, 35%) $^1$H NMR (500 MHz, Chloroform-d) 8.58-8.53 (m, 1H), 8.29-8.24 (m, 1H), 7.98 (s, 2H), 2.54 (s, 3H) and 5-methyl-3-(1H-1,2,3-triazol-1-yl)picolinonitrile (387 mg, 27%).

Step B: (sodium 5-methyl-3-(2H-1,2,3-triazol-2-yl)picolinate). To a solution of the title compound of Step A (489 mg, 2.6 mmol) in EtOH (7 mL) was added 4 N NaOH (660 μL, 2.6 mmol). The mixture was heated at 100° C. for 24 h. The reaction mixture was concentrated in vacuo to a white solid which was used without further purification in subsequent steps. MS (ESI) mass calcd. for C$_9$H$_8$N$_4$O$_2$, 204.1. m/z found 205.0 [M+H]$^+$.

Intermediate A-20

6-methyl-3-(2H-1,2,3-triazol-2-yl)picolinic acid

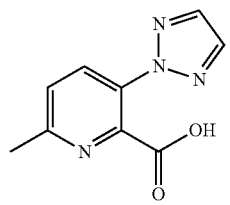

Step A: 6-methyl-3-(2H-1,2,3-triazol-2-yl)picolinonitrile. To 3-bromo-5-methylpicolinonitrile (2.2 g, 11 mmol) in DMF (28 mL) was added K$_2$CO$_3$ (1.7 g, 12 mmol) and 2H-1,2,3-triazole (650 μL, 11 mmol). The mixture was heated to 100° C. for 36 h, cooled to rt and extracted with EtOAc. The combined organics were dried (Na$_2$SO$_4$) and concentrated. Purification via silica gel chromatography (10-100% EtOAc in hexanes) gave the title compound (1 g, 48%).

Step B: 6-methyl-3-(2H-1,2,3-triazol-2-yl)picolinic acid. To a solution of the title compound of Step A (730 mg, 4 mmol) in EtOH (10 mL) was added 4 N NaOH (1 mL, 4 mmol). The mixture was heated at 100° C. for 24 h. The reaction mixture was concentrated in vacuo to a white solid which was used without further purification in subsequent steps. MS (ESI) mass calcd. for $C_9H_8N_4O_2$, 204.1. m/z found 205.1 $[M+H]^+$.

Intermediate A-21

3-ethoxyisoquinoline-4-carboxylic acid

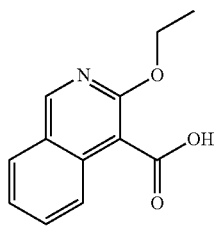 [SMILES: CCOc1ncc2ccccc2c1C(=O)O]

Step A: ethyl 3-hydroxyisoquinoline-4-carboxylate. To a suspension of ethyl 3-aminoisoquinoline-4-carboxylate (583 mg, 2.70 mmol) in 6.8 mL of $H_2SO_4$ 5 N cooled to 0° C. was added sodium nitrite (223 mg, 3.24 mmol, dissolved in 1 mL of water). The reaction mixture was stirred at 0° C. for 2.5 h and then $NaOH_{(aq)}$ 1N was added until pH=7. The aqueous phase was extracted twice with DCM and the combined organic phases were dried over $MgSO_4$, filtered and evaporated to give the title compound of Step A which was used without further purification in the next step (583 mg, 99%). MS (ESI) mass calcd. for $C_{12}H_{11}NO_3$, 217.1. m/z found 218.1 $[M+H]^+$.

Step B: ethyl 3-ethoxyisoquinoline-4-carboxylate. To the title compound of Step A (583 mg, 2.68 mmol) in THF (13 mL) was added triphenylphosphine (1.06 g, 4.03 mmol), ethanol (0.24 mL, 4.03 mmol) and DIAD (0.79 mL, 4.03 mmol). The reaction mixture was stirred at room temperature for 16 h and then the solvent was evaporated. The crude was purified via silica gel chromatography (0-30% EtOAc in hexanes) to afford the title compound of Step B (498 mg, 76%). MS (ESI) mass calcd. for $C_{14}H_{15}NO_3$, 245.1. m/z found 246.1 $[M+H]^+$. $^1H$ NMR (500 MHz, Chloroform-d) δ 8.97 (s, 1H), 7.91-7.82 (m, 2H), 7.65-7.60 (m, 1H), 7.42-7.36 (m, 1H), 4.59-4.48 (m, 4H), 1.48-1.39 (m, 6H).

Step C: 3-ethoxyisoquinoline-4-carboxylic acid. The title compound of Step B (492 mg, 2 mmol) dissolved in MeOH (15 mL) was added $NaOH_{(aq)}$ 2M (2.5 mL). The reaction mixture was stirred at 60° C. for 16 h and then $NaOH_{(aq)}$ 4M (2 mL) was added and the mixture was stirred at 70° C. for 4 h. MeOH was evaporated and the aqueous phase was cooled to 0° C. and acidified with the addition of $HCl_{(aq)}$ 6N. The solid was filtered, washed with cold water and dried to afford the title compound (285 mg, 65%). MS (ESI) mass calcd. for $C_{12}H_{11}NO_3$, 217.1. m/z found 218.1 $[M+H]^+$. $^1H$ NMR (400 MHz, DMSO-d6) δ 13.36 (s, 1H), 9.15 (s, 1H), 8.13-8.06 (m, 1H), 7.82-7.70 (m, 2H), 7.54-7.47 (m, 1H), 4.50 (q, J=7.0 Hz, 2H), 1.35 (t, J=7.0 Hz, 3H).

| Intermediate | Name | Structure | Reference |
|---|---|---|---|
| A-22 | 3-methyl-2-(2H-1,2,3-triazol-2-yl)benzoic acid | 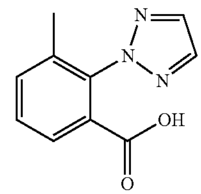 | Prepared according to WO 2011/050198 Intermediate 82 |
| A-23 | 4-fluoro-2-(pyrimidin-2-yl)benzoic acid | 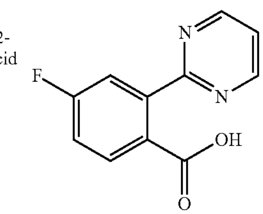 | Prepared according to WO 2011/050198 Intermediate 87 |

Intermediate A-24

2-methoxy-6-(pyrimidin-2-yl)benzoic acid

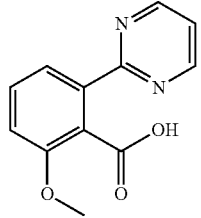 [SMILES: COc1cccc(-c2ncccn2)c1C(=O)O]

Step A: Methyl 2-methoxy-6-(pyrimidin-2-yl)benzoate. In a microwave vial was dissolved methyl 2-methoxy-6-(4,4,5,5-tetramethyl-1,3,2-dioxaborolan-2-yl)benzoate (CAS 1146214-77-8) (500 mg, 1.71 mmol) and 2-bromopyrimidine (344 mg, 2.05 mmol) in THF (8.5 mL). $Na_2CO_3$ (544 mg, 5.14 mmol) was then added followed by water (4 mL) and the reaction mixture was degassed with $N_2$ for 10 minutes. $PdCl_2(dtbpf)$ (CAS 95408-45-0) (45 mg, 0.069 mmol) was then added and the reaction mixture was heated at 80° C. for 4 h. The mixture was cooled to room temperature and water and EtOAc added. The reaction mixture was extracted with EtOAc (3×). The combined organic layers were dried over $Na_2SO_4$, filtered and concentrated. The crude was purified via silica gel chromatography (0-70% EtOAc in hexanes) to afford the title compound (265 mg, 63%). MS (ESI) mass calcd. for $C_{13}H_{12}N_2O_3$, 244.1. m/z found 245.1 $[M+H]^+$. $^1H$ NMR (400 MHz, Chloroform-d) δ 8.78 (d, J=4.9 Hz, 2H), 7.99 (dd, J=7.9, 0.9 Hz, 1H), 7.49 (t, J=8.1 Hz, 1H), 7.19 (t, J=4.8 Hz, 1H), 7.09 (dd, J=8.3, 0.9 Hz, 1H), 3.90 (s, 3H), 3.89 (s, 3H).

Step B: 2-methoxy-6-(pyrimidin-2-yl)benzoic acid. To a solution of the title compound of Step A (265 mg, 1.09 mmol) in THF (4 mL) was added 2 M NaOH (2 mL). The mixture was heated at 50° C. for 72 h. The reaction mixture was cooled to room temperature and concentrated in vacuo to remove THF. Then, 1 M $HCl_{(aq)}$ was added and the aqueous was extracted with 10:1 DCM/2,2,2-trifluoroethanol (3×). The combined organic layers were dried over $Na_2SO_4$, filtered and concentrated to give intermediate A-24, which was used without further purification in subsequent steps. MS (ESI) mass calcd. for $C_{12}H_{10}N_2O_3$, 230.1. m/z found 231.1 $[M+H]^+$. $^1H$ NMR (500 MHz, DMSO-$d_6$) δ 12.63 (s, 1H), 8.86 (d, J=4.9 Hz, 2H), 7.77 (dd, J=7.9, 1.0

Hz, 1H), 7.51 (t, J=8.1 Hz, 1H), 7.45 (t, J=4.9 Hz, 1H), 7.25 (dd, J=8.4, 1.0 Hz, 1H), 3.83 (s, 3H).

Intermediate A-25

7-ethoxyquinoline-8-carboxylic acid

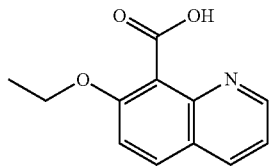 [SMILES: CCOc1ccc2cccnc2c1C(=O)O]

Step A: 7-methoxyquinoline-8-carboxylic acid. In separate batches (1 g) a mixture of 2-amino-6-methoxybenzoic acid (11 g, 66 mmol) and acrolein (4.8 mL, 72 mmol) in 1,4-dioxane (66 mL) was heated in a microwave reactor for 20 min at 200° C. After combining the reactions, the mixture was concentrated and purified via silica gel chromatography (0-10% MeOH in DCM) to give the title compound (2.8 g, 20%). MS (ESI) mass calcd. for $C_{11}H_{19}NO_3$, 203.1. m/z found 204.0 [M+H]$^+$.

Step B: 7-hydroxyquinoline-8-carboxylic acid. The title compound of Step A (2.9 g, 14.1 mmol) in HBr (14 mL) was heated at 90° C. for 1 h. The mixture was then concentrated washed with PhCH$_3$ and used without further purification in subsequent steps.

Step C: ethyl 7-ethoxyquinoline-8-carboxylate. To the title compound of Step B (800 mg, 3.9 mmol) and K$_2$CO$_3$ (1.4 g, 10.4 mmol) in DMF (15 mL) was added iodoethane (560 mL, 6.9 mmol). After stirring overnight at room temperature, the reaction was concentrated and purified via silica gel chromatography (0-30% EtOAc in hexanes) to give the title compound. MS (ESI) mass calcd. for $C_{14}H_{15}NO_3$, 245.1. m/z found 246.0 [M+H]$^+$.

Step D: 7-ethoxyquinoline-8-carboxylic acid. To the title compound of Step C (1.3 g, 5.4 mmol) in THF (22 mL) and H$_2$O (11 mL) was added LiOH hydrate (675 mg, 16.5 mmol) and MeOH. The mixture was heated at 67° C. for 12 h. Additional LiOH hydrate (675 mg, 16.5 mmol) was added and the heating was continued at 70° C. for 1 day. Additional LiOH hydrate (1.4 g, 33 mmol) was added and the heating was continued at 75° C. for 1 day. The reaction was allowed to cool to room temperature, acidified to pH=3 with 1 N HCl$_{(aq)}$ and concentrated. Purification via prep HPLC gave the title compound (1 g, 84%). MS (ESI) mass calcd. for $C_{12}H_{11}NO_3$, 217.1. m/z found 218.0 [M+H]$^+$.

Intermediate A-27

3-methyl-2-(oxazol-2-yl)benzoic acid

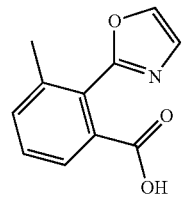

Step A: ethyl 3-methyl-2-(oxazol-2-yl)benzoate. In a microwave vial was dissolved ethyl 2-iodo-3-methylbenzoate (627 mg, 2.16 mmol) and 2-(tributylstannyl)oxazole (0.54 mL, 0.07 mmol) in DME (2.59 mL). The solution was degassed with N$_2$ for 5 minutes then CuI (21 mg, 0.11 mmol) and Pd(PPh$_3$)$_4$ (125 mg, 0.11 mmol) were added. The reaction was purged with N$_2$ and heated at 150° C. for 1 h. The reaction was cooled to room temperature, filtered through a pad of Celite and purified via silica gel chromatography (0-40% EtOAc in hexanes) to give the title compound of step A (333 mg, 67%). MS (ESI) mass calcd. for $C_{13}H_{13}NO_3$, 231.1. m/z found 232.1 [M+H]$^+$. $^1$H NMR (500 MHz, Chloroform-d) δ 7.89-7.82 (m, 1H), 7.79 (d, J=0.8 Hz, 1H), 7.48-7.43 (m, 2H), 7.30 (d, J=0.9 Hz, 1H), 4.17 (q, J=7.1 Hz, 2H), 2.27 (s, 3H), 1.18 (t, J=7.1 Hz, 3H).

Step B: 3-methyl-2-(oxazol-2-yl)benzoic acid. To the title compound of step A (166 mg, 0.72 mmol) was added MeOH (7.2 mL) and 1M NaOH$_{(aq)}$ (7.2 mL). MeOH was evaporated and then 1 M HCl$_{(aq)}$ was added. To the solution was added DCM and the aqueous was extracted with DCM (3×). The combined organic layers were dried over MgSO$_4$, filtered and evaporated to give the title compound (145 mg). MS (ESI) mass calcd. for $C_{11}H_9NO_3$, 203.1. m/z found 204.1 [M+H]$^+$. $^1$H NMR (400 MHz, DMSO-d$_6$) δ 8.20 (s, 1H), 7.79-7.68 (m, 1H), 7.65-7.49 (m, 2H), 7.35 (s, 1H), 4.34 (s, 1H), 2.20 (s, 3H).

| Intermediate | Name | Structure | Reference |
|---|---|---|---|
| A-28 | 3-(2H-1,2,3-triazol-2-yl)picolinic acid | 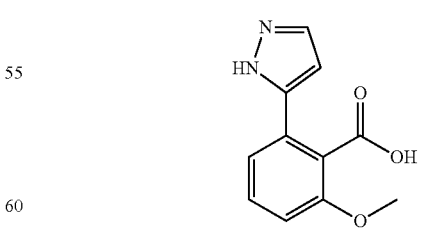 | Prepared according to WO 2011/050198 Intermediate 72 |
| A-29 | 1H-indole-7-carboxylic acid | 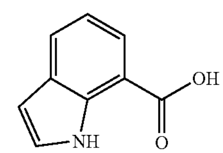 [SMILES: O=C(O)c1cccc2cc[nH]c12] | Commercially available, CAS 1670-83-3 |

Intermediate A-30

2-methoxy-6-(1H-pyrazol-5-yl)benzoic acid

Step A: Ethyl 2-methoxy-6-(1H-pyrazol-5-yl)benzoate. In a microwave vial was dissolved ethyl 2-bromo-6-methoxybenzoate (500 mg, 1.54 mmol) and 5-(4,4,5,5-tetramethyl-1,3,2-dioxaborolan-2-yl)-1H-pyrazole (330 mg, 1.70 mmol) in DME (10 mL) and water (2 mL). Na$_2$CO$_3$ (259 mg, 3.09 mmol) was then added followed by Pd(PPh₃)₄ (89 mg, 0.077 mmol) and the reaction mixture was degassed with N₂ for 10 minutes. The reaction mixture was then heated at 100° C. for 1 h in the microwave. The mixture was cooled to room temperature, filtered through Celite and washed with EtOAc and DCM. The crude solution was concentrated in vacuo and directly purified via silica gel chromatography (10-80% EtOAc in hexanes) to afford the title compound (125 mg, 33%). MS (ESI) mass calcd. for $C_{13}H_{14}N_2O_3$, 246.3. m/z found 247.1 [M+H]⁺. ¹H NMR (400 MHz, Chloroform-d) δ 7.63 (d, J=2.2 Hz, 1H), 7.44-7.37 (m, 1H), 7.24 (d, J=8.1 Hz, 1H), 6.94 (dd, J=8.3, 0.9 Hz, 1H), 6.53 (d, J=2.3 Hz, 1H), 4.29 (q, J=7.2 Hz, 2H), 3.88 (s, 3H), 1.25-1.16 (m, 3H).

Step B: 2-methoxy-6-(1H-pyrazol-5-yl)benzoic acid. Prepared analogous to intermediate A-24 step B to give title compound. MS (ESI) mass calcd. for $C_{11}H_{10}N_2O_3$, 218.1. m/z found 219.1 [M+H]⁺. ¹H NMR (500 MHz, DMSO-d₆) δ 12.85 (br. s, 1H), 7.71 (d, J=2.2 Hz, 1H), 7.39 (t, J=8.0 Hz, 1H), 7.35-7.28 (m, 1H), 7.04 (dd, J=8.3, 1.0 Hz, 1H), 6.51 (d, J=2.3 Hz, 1H), 3.80 (s, 3H).

Intermediate A-31

2-(1,4-dimethyl-1H-pyrazol-5-yl)benzoic acid

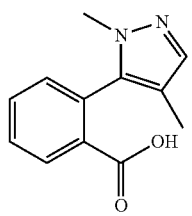 [SMILES: Cc1cnn(C)c1-c1ccccc1C(=O)O]

Step A: Methyl 2-(1,4-dimethyl-1H-pyrazol-5-yl)benzoate. Prepared analogous to intermediate A-30 step A to give title compound. MS (ESI) mass calcd. for $C_{13}H_{14}N_2O_2$, 230.1. m/z found 231.1 [M+H]⁺. ¹H NMR (400 MHz, Chloroform-d) δ 8.04 (dd, J=7.8, 1.5 Hz, 1H), 7.61 (td, J=7.5, 1.5 Hz, 1H), 7.53 (td, J=7.7, 1.4 Hz, 1H), 7.35 (s, 1H), 7.28 (dd, J=7.6, 1.4 Hz, 1H), 3.71 (s, 3H), 3.58 (s, 3H), 1.84 (s, 3H).

Step B: 2-(1,4-dimethyl-1H-pyrazol-5-yl)benzoic acid. To a solution of the title compound of Step A (680 mg, 2.95 mmol) in MeOH (15 mL) was added 4 M LiOH (4 mL). The mixture was heated at 50° C. overnight. MeOH was removed and HCl added until pH=2. White solids precipitated from the reaction mixture and the precipitate was filtered, washed with EtOAc and collected to give intermediate A-31, which was used without further purification in subsequent steps. MS (ESI) mass calcd. for $C_{12}H_{12}N_2O_2$, 216.1. m/z found 217.1 [M+H]⁺. ¹H NMR (400 MHz, DMSO-d₆) δ 12.87 (s, 1H), 7.95 (dd, J=7.8, 1.5 Hz, 1H), 7.67 (td, J=7.5, 1.5 Hz, 1H), 7.59 (td, J=7.6, 1.4 Hz, 1H), 7.33 (dd, J=7.6, 1.4 Hz, 1H), 7.25 (s, 1H), 3.48 (s, 3H), 1.77 (s, 3H).

| Intermediate | Name | Structure | Reference |
|---|---|---|---|
| A-33 | 2-bromo-3-fluorobenzoic acid | 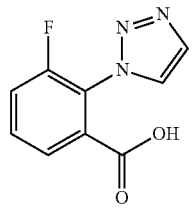 [SMILES: O=C(O)c1cccc(F)c1-n1ccnn1] | Commercially available, CAS 132715-69-6 |

Intermediate A-33

3-fluoro-2-(1H-1,2,3-triazol-1-yl)benzoic acid

To 3-fluoro-2-iodobenzoic acid (4.5 g, 16.9 mmol) dissolved in dioxane (33.8 mL) and H₂O (0.09 mL) was added Cs₂CO₃ (11.02 g, 33.8 mmol), CuI (161 mg, 0.85 mmol), 2H-1,2,3-triazole (1.96 mL, 33.8 mmol), and trans-N,N-dimethyl-1,2-cyclohexanediamine (0.53 mL, 3.38 mmol). The mixture was then heated to 100° C. overnight, cooled to room temperature, diluted with H₂O, and extracted with EtOAc. The aqueous layer was then acidified and extracted with EtOAc. The combined organics were dried and concentrated. From this concentrate a solid precipitated to provide intermediate A-33 (285 mg, 8%). MS (ESI) mass calcd for $C_9H_6FN_3O_2$, 207.0. m/z found 208.1 [M+H]⁺. ¹H NMR (500 MHz, Methanol-d₄) δ 6.81-6.77 (m, 1H), 6.46-6.40 (m, 2H), 6.30-6.23 (m, 1H), 6.18-6.12 (m, 1H).

Enantiopure Route A
(2-azabicyclo[2.2.1]heptan-6-ol)

Intermediate B-1

(1S,4R)-2-((R)-1-phenylethyl)-2-azabicyclo[2.2.1]hept-5-ene

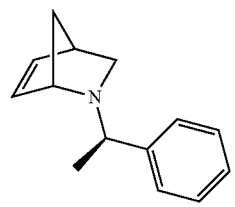

Intermediate B-1 was prepared according to the procedure of C. Chiu et al. [*Synthetic Communications* 1996, 26, 577-584] with the substitution of (+)-α-Methyl-benzylamine for (−)-α-Methyl-benzylamine and D-dibenzoyl tartaric acid for L-dibenzoyl tartaric acid. MS (ESI) mass calcd. for C₁₄H₁₇N, 199.1. m/z found 200.1 [M+H]⁺. ¹H NMR (400 MHz, Chloroform-d) δ 7.36-7.25 (m, 4H), 7.23-7.17 (m, 1H), 6.35-6.30 (m, 1H), 6.11 (dd, J=5.7, 2.0 Hz, 1H), 4.16-4.12 (m, 1H), 3.05 (q, J=6.5 Hz, 1H), 2.89 (dd, J=8.9, 3.1 Hz, 1H), 2.85-2.81 (m, 1H), 1.65-1.59 (m, 1H), 1.48-1.43 (m, 1H), 1.37-1.31 (m, 4H).

Intermediate B-2

(1S,4R,6S)-2-((R)-1-phenylethyl)-2-azabicyclo[2.2.1]heptan-6-ol

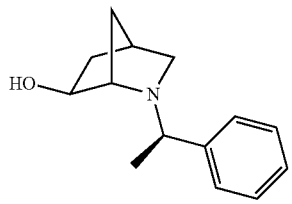 [SMILES: C[C@H](c1ccccc1)N1CC2CC(O)C1C2]

Intermediate B-2 was synthesized according to the procedure of F. Carroll et al. [*J. Med. Chem.* 1992, 35, 2184-2191] on a similar substrate. A 1 M solution of BH₃-THF (1 M BH₃-THF in THF, 359.3 mL, 359.3 mmol) was added dropwise via addition funnel to a stirred solution of intermediate B-1 (35.8 g, 179.6 mmol) in THF (359 mL) at 0° C. Upon complete addition of BH₃-THF, the reaction mixture was stirred at 0° C. for 2 h. Then, excess BH₃ was quenched with a solution of THF-H₂O. A 3 M NaOH (132 mL) solution was added followed by the dropwise addition of H₂O₂ (30% w/w in H₂O, 140 mL), and the reaction mixture was warmed to 40° C. and stirred for 1.5 h. The biphasic mixture was then cooled to room temperature and K₂CO₃ (17 g) added in one portion. The resulting mixture was concentrated under reduced pressure to remove THF and re-dissolved in DCM. The crude reaction mixture was washed with H₂O and the aqueous phase extracted with DCM (3×). The combined organics were then washed with brine, dried with Na₂SO₄, filtered, and concentrated to give a clear oil, which was further purified by silica gel chromatography (5-10% MeOH (with 10% 2 M NH₃) in DCM) to give intermediate B-2 as a clear oil (20.2 g, 93.0 mmol, 52%). MS (ESI) mass calcd. for C₁₄H₁₉NO, 217.2. m/z found 218.1 [M+H]⁺. ¹H NMR (500 MHz, Chloroform-d) δ 7.34-7.27 (m, 4H), 7.24-7.19 (m, 1H), 4.03 (d, J=6.9 Hz, 1H), 3.46 (q, J=6.5 Hz, 1H), 3.01 (s, 1H), 2.56-2.48 (m, 1H), 2.42-2.33 (m, 1H), 2.25 (dd, J=8.8, 1.3 Hz, 1H), 1.82 (ddd, J=13.1, 6.9, 2.2 Hz, 1H), 1.53-1.43 (m, 2H), 1.33-1.28 (m, 1H), 1.27 (d, J=6.5 Hz, 3H).

Intermediate B-3

(1S,4R,6S)-tert-butyl 6-hydroxy-2-azabicyclo[2.2.1]heptane-2-carboxylate

To a solution of intermediate B-2 (500 mg, 2.3 mmol) in EtOH (11.5 mL) was added Boc₂O (603 mg, 2.76 mmol) and 10 wt % Pd/C wet Degussa (490 mg, 0.46 mmol). The reaction mixture was stirred under an atmosphere of H₂ (balloon) at room temperature for 22 h. Then, the reaction mixture was filtered through a pad of Celite and washed with EtOAc. The filtrate was concentrated to a clear oil to give the title compound in quantitative yield, which was used without further purification. MS (ESI) mass calcd. for C₁₁H₁₉NO₃, 213.1. m/z found 158.1 [M+2H-tBu]⁺. ¹H NMR (400 MHz, Chloroform-d, Compound present as a mixture of rotamers) δ 4.08-3.99 (m, 1H), 3.99-3.92 (m, 1H), 3.18-3.09 (m, 1H), 2.80 (dd, J=28.1, 9.2 Hz, 1H), 2.18-1.37 (m, 14H).

Intermediate B-4

(1S,4R)-tert-butyl 6-oxo-2-azabicyclo[2.2.1]heptane-2-carboxylate

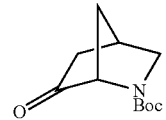 [SMILES: CC(C)(C)OC(=O)N1CC2CC(=O)C1C2]

To a solution of intermediate B-3 (7 g, 33 mmol) in EtOAc (219 mL) was added IBX (24.5 g, 39.4 mmol), and the heterogeneous reaction mixture was stirred at 80° C. overnight. Upon completion, the reaction mixture was then filtered through Celite, washed with EtOAc and concentrated to a white solid. The crude reaction mixture was re-dissolved in EtOAc and washed once with a 5% aqueous Na₂CO₃ solution. The aqueous layer was further extracted with EtOAc (2×) and the combined organics were washed with brine, dried with Na₂SO₄, filtered, and concentrated to afford intermediate B-4 as a light yellow solid (6.12 g, 28.9 mmol, 88%), which was used in the next step without further purification. MS (ESI) mass calcd. for C₁₁H₁₂NO₃, 211.1. m/z found 156.1 [M+2H-tBu]⁺. ¹H NMR (400 MHz, Chloroform-d) δ 4.32-4.04 (m, 1H), 3.45 (ddd, J=9.6, 3.1, 1.8 Hz, 1H), 3.25-3.04 (m, 1H), 2.89-2.77 (m, 1H), 2.21 (ddd, J=18.0, 4.6, 1.8 Hz, 1H), 2.04-1.96 (m, 1H), 1.95-1.82 (m, 1H), 1.75-1.66 (m, 1H), 1.45 (s, 9H).

Intermediate B-5

(1S,4R,6R)-tert-butyl 6-hydroxy-2-azabicyclo[2.2.1]heptane-2-carboxylate

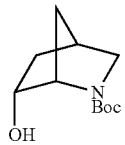

A 1 M solution of L-Selectride (1 M in THF, 19.8 mL, 19.8 mmol) was added to a solution of intermediate B-4 (1.67 g, 7.91 mmol) in dry THF (40 mL) at −78° C., and the reaction mixture was stirred at that temperature for 3 h. Then, the reaction mixture was warmed to 0° C. and a 3 M NaOH (8.4 mL) solution was added followed by a solution of $H_2O_2$ (30% w/w in $H_2O$, 4.3 mL). The resulting mixture was warmed to room temperature and stirred for 2 h. The biphasic mixture was then concentrated in vacuo to remove THF and the aqueous layer extracted with DCM (3×). The combined organics were washed with brine, dried with $Na_2SO_4$, filtered, and concentrated to an oil, which was further purified by silica gel chromatography (10-90% EtOAc in hexanes), to give intermediate B-2 as a white solid (1.16 g, 5.44 mmol, 67%). MS (ESI) mass calcd. for $C_{11}H_{19}NO_3$, 213.1. m/z found 158.1 [M+2H-tBu]$^+$. $^1$H NMR (400 MHz, Chloroform-d, Compound present as a mixture of rotamers) δ 4.38-4.10 (m, 2H), 3.36 (br. s, 1H), 3.09 (dd, J=9.6, 1.4 Hz, 1H), 2.54-1.38 (m, 14H), 1.16-1.00 (m, 1H). Intermediate B-5 can also be prepared from commercially available (1S,4R)-2-azabicyclo[2.2.1]hept-5-en-3-one. The procedure is as follows:

Enantiopure Route B
(2-azabicyclo[2.2.1]heptan-6-ol)

Intermediate B-6

(1 S,4R,6S)-2-benzyl-2-azabicyclo[2.2.1]heptan-6-ol

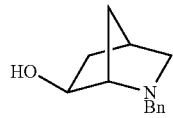

To a round bottom flask containing commercially available, (1S,4R)-2-azabicyclo[2.2.1]hept-5-en-3-one (2.0 g, 18.3 mmol), in THF (100 mL) at 0° C. was added a solution of LiAlH$_4$ (1 M in THF, 40.3 mL, 40.3 mmol), and the reaction mixture was refluxed overnight. The reaction mixture was then cooled to 0° C. and carefully quenched by the dropwise addition of $H_2O$ (15 mL). Celite and solid $Na_2CO_3$ were added to the slurry and the reaction mixture was vigorously stirred at room temperature for 3 h. The slurry was then filtered and the solids washed with THF. Benzyl bromide (2.4 mL, 20.2 mmol) and an aqueous solution of $Na_2CO_3$ (3.2 g in 30 mL $H_2O$) were added to the filtrate and the reaction mixture stirred at room temperature overnight. Upon completion of the reaction, the reaction mixture was extracted with EtOAc (3×). The combined organics were washed with $H_2O$, brine, dried with MgSO$_4$, filtered, and concentrated to provide crude (1S,4R)-2-benzyl-2-azabicyclo[2.2.1]hept-5-ene as a yellow oil, which was directly hydroborated according to the procedure of F. Carroll et al. [*J. Med. Chem.* 1992, 35, 2184-2191]. The crude alcohol was purified by silica gel chromatography (0-15% MeOH (with 5% NH$_4$OH) in DCM) to give intermediate B-6 as a clear oil (2.66 g, 13.1 mmol, 71% over 3 steps). MS (ESI) mass calcd for $C_{13}H_{17}NO$, 203.1. m/z found 204.1 [M+H]$^+$. $^1$H NMR (500 MHz, Chloroform-d) δ 7.39-7.28 (m, 4H), 7.26-7.21 (m, 1H), 4.18-4.09 (m, 1H), 3.76-3.66 (m, 2H), 3.06 (br. s, 1H), 2.51 (dt, J=9.0, 3.0 Hz, 1H), 2.44-2.35 (m, 2H), 1.90-1.81 (m, 1H), 1.68-1.53 (m, 2H), 1.38-1.30 (m, 1H).

Intermediate B-7

(1S,4R,6R)-2-benzyl-2-azabicyclo[2.2.1]heptan-6-ol

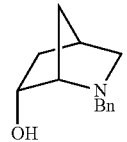

Intermediate B-7 was prepared from intermediate B-6 according to the procedure of F. Carroll et al. [*J Med. Chem.* 1992, 35, 2184-2191]. MS (ESI) mass calcd for $C_{13}H_{12}NO$, 203.1. m/z found 204.1 [M+H]$^+$. $^1$H NMR (500 MHz, Chloroform-d) δ 7.37-7.22 (m, 5H), 4.56 (s, 1H), 4.05-3.94 (m, 1H), 3.80 (d, J=13.0 Hz, 1H), 3.62 (d, J=12.9 Hz, 1H), 3.20-3.11 (m, 1H), 2.77 (d, J=9.2 Hz, 1H), 2.45-2.34 (m, 2H), 1.88-1.79 (m, 1H), 1.76-1.64 (m, 1H), 1.30 (d, J=10.4 Hz, 1H), 0.99 (dt, J=13.3, 2.9 Hz, 1H).

Intermediate B-5

(1S,4R,6R)-tert-butyl
6-hydroxy-2-azabicyclo[2.2.1]heptane-2-carboxylate

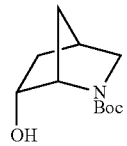

To a solution of intermediate B-7 (3.41 g, 16.8 mmol) in EtOH (168 mL) was added Boc$_2$O (5.49 g, 25.2 mmol) and 20 wt % Pd(OH)$_2$/C (2.36 g, 3.36 mmol). The reaction mixture was stirred under an atmosphere of H$_2$ (balloon) at room temperature overnight. Then, the reaction mixture was filtered through a pad of Celite and washed with EtOAc. The filtrate was concentrated to a clear oil, which was further purified by silica gel chromatography (10-60% EtOAc in hexanes), to give intermediate B-5 as a white solid (3.1 g, 1.5 mmol, 87%). MS (ESI) mass calcd. for $C_{11}H_{19}NO_3$, 213.1. m/z found 158.1 [M+2H-tBu]$^+$. $^1$H NMR (500 MHz, Chloroform-d, Compound present as a mixture of rotamers) δ 4.39-4.12 (m, 2H), 3.35 (br. s, 1H), 3.08 (dd, J=9.4, 1.4 Hz, 1H), 2.56-1.39 (m, 14H), 1.15-0.99 (m, 1H).

Racemic Route (2-azabicyclo[2.2.1]heptan-6-ol)

Intermediate B-8

(R/S)-tert-butyl
6-hydroxy-2-azabicyclo[2.2.1]heptane-2-carboxylate

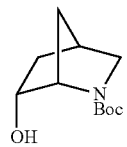

Intermediate B-8 was prepared from commercially available (R/S)-tert-butyl 6-oxo-2-azabicyclo[2.2.1]heptane-2-carboxylate following the procedure of R. Nencka et. al. [*Tetrahedron* 2012, 68, 1286-1298]. MS (ESI) mass calcd. for $C_{11}H_{19}NO_3$, 213.1. m/z found 158.1 [M+2H-tBu]$^+$. $^1$H NMR (400 MHz, Chloroform-d) δ 4.39-4.08 (m, 2H), 3.36 (br.s, 1H), 3.10 (dd, J=9.6, 1.4 Hz, 1H), 2.56-1.41 (m, 14H), 1.17-1.01 (m, 1H).

Enantiopure Route
(2-azabicyclo[2.2.1]heptan-6-amine)

Intermediate B-9

(1S,4R)-tert-butyl 6-(hydroxyimino)-2-azabicyclo[2.2.1]heptane-2-carboxylate

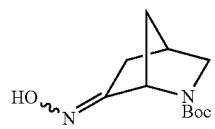

To a flask containing Intermediate B-4 (1.0 g, 4.7 mmol) dissolved in EtOH (20 mL) was added NEt$_3$ (2.0 ml, 14.4 mmol), and hydroxylamine hydrochloride (789 mg, 2.40 mmol) and the reaction mixture was brought to reflux. Upon completion, the reaction mixture was concentrated, diluted with H$_2$O, and the aqueous layer extracted with EtOAc (3×). The combined organics were then washed with H$_2$O, brine, dried with MgSO$_4$, filtered, and concentrated to provide intermediate B-7 as an off-white solid (1.018 g) which was used without further purification. MS (ESI) mass calcd. for $C_{11}H_{18}N_2O_3$, 226.1. m/z found 171.1 [M+2H-tBu]$^+$. $^1$H NMR (500 MHz, Chloroform-d) δ 7.71 and 7.41 (2s, 1H), 4.62 and 4.48 (2s, 1H), 3.40-3.33 (m, 1H), 3.15-2.96 (m, 1H), 2.79-2.70 (m, 1H), 2.54-2.43 (m, 1H), 2.29-2.19 (m, 1H), 1.87-1.64 (m, 1H), 1.61-1.53 (m, 1H), 1.45 (s, 9H).

Intermediate B-10

(1S,4S,6R)-tert-butyl 6-amino-2-azabicyclo[2.2.1]heptane-2-carboxylate

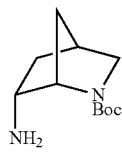

A mixture of NiCl$_2$ (1.15 g, 8.84 mmol) and intermediate B-9 (1.0 g, 4.4 mmol) in MeOH (30 mL) was cooled to −35° C. and NaBH$_4$ (3.34 g, 88.4 mmol) was added portion wise to the reaction mixture over 30 min. Upon complete addition of NaBH$_4$, the reaction mixture was stirred for an additional 25 min and then warmed to room temperature. After 30 min at room temperature the reaction mixture was quenched with H$_2$O and concentrated under reduced pressure to a dark brown residue, which was re-dissolved in a mixture of DCM and 15% aqueous NaOH solution, and the aqueous layer extracted with DCM (3×). The combined organics were dried with MgSO$_4$, filtered, and concentrated to provide intermediate B-10 (209 mg). 5 N NH$_4$OH solution was then added to the aqueous layer along with DCM, NaCl, and Celite and after several minutes of stirring the mixture was filtered to remove solids. The filtrate was then transferred to a separatory funnel, the layers separated, and the aqueous layer extracted with DCM (2×). The combined organics were dried with MgSO$_4$, filtered, and concentrated to provide additional intermediate B-10 (582 mg) which was combined with the above fraction to provide intermediate B-10 (791 mg) as a brown oil which was used without further purification. MS (ESI) mass calcd. for $C_{11}H_{20}N_2O_2$, 212.2. m/z found 213.1 [M+H]$^+$. $^1$H NMR (500 MHz, Chloroform-d) δ 4.13-3.92 (m, 1H), 3.41-3.27 (m, 2H), 2.99 (dd, J=24.3, 9.6 Hz, 1H), 2.51-2.39 (m, 1H), 2.16-2.05 (m, 1H), 1.68-1.57 (m, 1H), 1.47 (s, 10H), 1.22-1.07 (m, 2H), 0.85-0.74 (m, 1H).

Example 1

(R/S)-(2-(2H-1,2,3-triazol-2-yl)phenyl)(6-((5-(trifluoromethyl)pyrazin-2-yl)oxy)-2-azabicyclo[2.2.1]heptan-2-yl)methanone

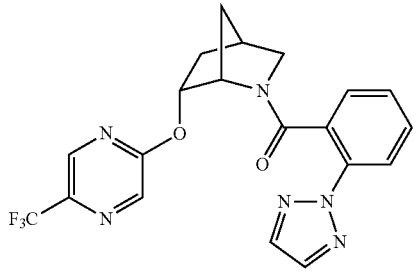 [SMILES: O=C(c1ccccc1-n1nccn1)N1CC2CC(Oc3cnc(C(F)(F)F)cn3)C1C2]

Step A: (R/S)-tert-butyl 6-((5-(trifluoromethyl)pyrazin-2-yl)oxy)-2-azabicyclo[2.2.1]heptane-2-carboxylate. To intermediate B-8 (100 mg, 0.469 mmol) dissolved in DMF (3 mL) was added NaH (28 mg, 0.70 mmol, 60% dispersion in mineral oil). After 5 minutes 2-chloro-5-(trifluoromethyl)pyrazine (0.087 mL, 0.70 mmol) was then added and the mixture heated to 90° C. After heating at 90° C. for 3.5 h, the mixture was cooled to room temperature, quenched with saturated NH$_4$Cl solution, and diluted with EtOAc and H$_2$O. The aqueous layer was extracted with EtOAc (3×). The combined organics were washed with H$_2$O, brine, dried with MgSO$_4$, filtered and concentrated. Purification via silica gel chromatography (0-20% EtOAc in hexanes) gave the title compound (151 mg, 0.420 mmol, 90%). MS (ESI) mass calcd. for $C_{16}H_{20}F_3N_3O_3$, 359.1. m/z found 304.1 [M+2H-tBu]$^+$. $^1$H NMR (400 MHz, Chloroform-d. compound present as a mixture of rotamers) δ 8.46-8.41 (m, 1H), 8.27-8.24 and 8.16-8.12 (2m, 1H), 5.45-5.30 (m, 1H), 4.63-4.48 (m, 1H), 3.48-3.33 (m, 1H), 3.28-3.13 (m, 1H), 2.67-2.54 (m, 1H), 2.32-2.19 (m, 1H), 1.85-1.04 (m, 12H).

Step B: (R/S)-6-((5-(trifluoromethyl)pyrazin-2-yl)oxy)-2-azabicyclo[2.2.1]heptane.xHCl. To the title compound of step A (151 mg, 0.42 mmol) in EtOAc (1 mL) was added 4 M HCl in dioxane (6 mL). After 3.25 h, the reaction was concentrated to give the title compound of step B which was used without further purification. MS (ESI) mass calcd. for $C_{11}H_{12}F_3N_3O$, 259.1. m/z found 260.1 [M+H]$^+$.

Step C: (R/S)-(2-(2H-1,2,3-triazol-2-yl)phenyl)(6-((5-(trifluoromethyl)pyrazin-2-yl)oxy)-2-azabicyclo[2.2.1]heptan-2-yl)methanone. To the title compound of step B (43 mg) and intermediate A-1 (24 mg, 0.13 mmol) in DMF (1.5 mL) was added DIPEA (0.4 mL, 2.32 mmol) and HATU (48 mg, 0.13 mmol). Upon completion of the reaction, purification was performed using Agilent Prep Method X to give the title compound (9 mg). MS (ESI) mass calcd. for $C_{20}H_{17}F_3N_6O_2$, 430.1. m/z found 431.1 [M+H]$^+$. $^1$H NMR (400 MHz, Chloroform-d, Compound present as a mixture of rotamers (0.80:0.20), major rotamer reported) δ 8.25 (s, 1H), 8.02-7.98 (m, 1H), 7.87-7.79 (m, 3H), 7.32 (ddd, J=8.2, 7.4, 1.5 Hz, 1H), 7.04 (dd, J=7.7, 1.5 Hz, 1H), 6.81 (t, J=7.5 Hz, 1H), 4.97 (dt, J=10.2, 3.3 Hz, 1H), 4.03-3.96 (m, 1H), 3.62 (dt, J=11.0, 3.2 Hz, 1H), 3.44 (dd, J=10.9, 1.5 Hz, 1H), 2.68-2.63 (m, 1H), 2.27-2.18 (m, 1H), 1.48 (dt, J=13.6, 3.6 Hz, 1H), 1.40 (d, J=10.6 Hz, 1H), 1.33-1.25 (m, 1H).

Example 2

(R/S)-(6-methyl-3-(2H-1,2,3-triazol-2-yl)pyridin-2-yl)(6-((5-(trifluoromethyl)pyrazin-2-yl)oxy)-2-azabicyclo[2.2.1]heptan-2-yl)methanone

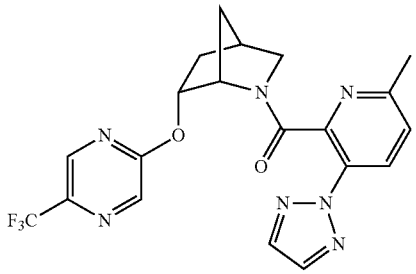 [SMILES: Cc1ccc(-n2nccn2)c(C(=O)N2CC3CC(Oc4cnc(C(F)(F)F)cn4)C2C3)n1]

Prepared analogous to Example 1 substituting intermediate A-1 with intermediate A-20. MS (ESI) mass calcd. for $C_{20}H_{18}F_3N_7O_2$, 445.1. m/z found 446.2 [M+H]$^+$. $^1$H NMR (400 MHz, Chloroform-d, Compound present as a mixture of rotamers (0.78:0.22), major rotamer reported) δ 8.30-8.27 (m, 1H), 8.05-8.00 (m, 2H), 7.83 (s, 2H), 7.11-7.07 (m, 1H), 5.01 (dt, J=10.2, 3.2 Hz, 1H), 4.27-4.23 (m, 1H), 3.70 (dt, J=11.0, 3.2 Hz, 1H), 3.49 (dd, J=11.0, 1.4 Hz, 1H), 2.72-2.67 (m, 1H), 2.30-2.21 (m, 4H), 1.60-1.48 (m, 3H).

Example 3

(R/S)-(3-ethoxyisoquinolin-4-yl)((5-(trifluoromethyl)pyrazin-2-yl)oxy)-2-azabicyclo[2.2.1]heptan-2-yl)methanone

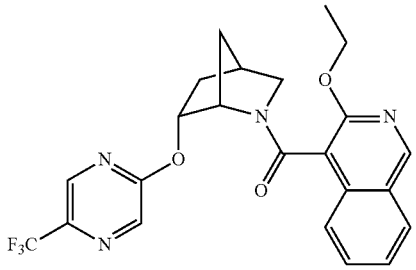 [SMILES: CCOc1ncc2ccccc2c1C(=O)N1CC2CC(Oc3cnc(C(F)(F)F)cn3)C1C2]

Prepared analogous to Example 1 substituting intermediate A-1 with intermediate A-21. MS (ESI) mass calcd. for $C_{23}H_{21}F_3N_4O_3$, 458.2. m/z found 459.2 [M+H]$^+$. $^1$H NMR (400 MHz, Chloroform-d, Compound present as a mixture of rotamers, major rotamer reported) δ 8.72 (d, J=0.8 Hz, 1H), 7.77-7.72 (m, 1H), 7.71-7.68 (m, 1H), 7.64-7.58 (m, 2H), 7.52-7.47 (m, 1H), 7.30 (ddd, J=8.1, 6.8, 1.1 Hz, 1H), 4.87 (dt, J=10.2, 3.4 Hz, 1H), 4.68-4.39 (m, 3H), 3.87 (dt, J=11.1, 3.2 Hz, 1H), 3.56 (dd, J=11.1, 1.6 Hz, 1H), 2.83-2.77 (m, 1H), 2.35-2.26 (m, 1H), 2.01-1.95 (m, 1H), 1.84-1.75 (m, 1H), 1.56-1.38 (m, 4H).

Example 4

(R/S)-5-methyl-3-(2H-1,2,3-triazol-2-yl)pyridin-2-yl)(6-((5-(trifluoromethyl)pyrazin-2-yl)oxy)-2-azabicyclo[2.2.1]heptan-2-yl)methanone

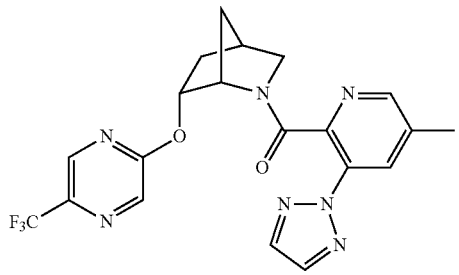 [SMILES: Cc1cnc(C(=O)N2CC3CC(Oc4cnc(C(F)(F)F)cn4)C2C3)c(-n2nccn2)c1]

Prepared analogous to Example 1 substituting intermediate A-1 with intermediate A-19. MS (ESI) mass calcd. for $C_{20}H_{18}F_3N_7O_2$, 445.1. m/z found 446.1 [M+H]$^+$. $^1$H NMR (400 MHz, Chloroform-d, Compound present as a mixture of rotamers (0.88:0.12), major rotamer reported) δ 8.34 (d, J=1.3 Hz, 1H), 8.00-7.95 (m, 2H), 7.84-7.80 (m, 2H), 7.62-7.59 (m, 1H), 5.10 (dt, J=10.3, 3.2 Hz, 1H), 4.27-4.24 (m, 1H), 3.71 (dt, J=11.0, 3.2 Hz, 1H), 3.49 (dd, J=11.0, 1.5 Hz, 1H), 2.76-2.70 (m, 1H), 2.34-2.22 (m, 4H), 1.71-1.54 (m, 3H).

Example 5

General Method

Step A: (R/S)-tert-butyl 6-((5-(trifluoromethyl)pyridin-2-yl)oxy)-2-azabicyclo[2.2.1]heptane-2-carboxylate. To intermediate B-8 (200 mg, 0.94 mmol) dissolved in DMF (5 mL) was added NaH (56 mg, 1.41 mmol, 60% dispersion in mineral oil). After 5 minutes 2-chloro-5-(trifluoromethyl) pyridine (340 mg, 1.87 mmol) was then added and the mixture heated to 80° C. After heating at 80° C. for 5.75 h, the mixture was cooled to room temperature, quenched with saturated NH$_4$Cl solution, diluted with H$_2$O, and the aqueous layer extracted with EtOAc (3×). The combined organics were washed with H$_2$O, brine, dried with MgSO$_4$, filtered and concentrated. Purification via silica gel chromatography (0-30% EtOAc in hexanes) gave the title compound (300 mg, 0.84 mmol, 89%). MS (ESI) mass calcd. for $C_{17}H_{21}F_3N_2O_3$, 358.2. m/z found 359.1 [M+H]$^+$. $^1$H NMR (400 MHz, Chloroform-d) δ 8.47-8.37 (m, 1H), 7.84-7.69 (m, 1H), 6.87-6.68 (m, 1H), 5.45-5.29 (m, 1H), 4.63-4.52 (m, 1H), 3.47-3.34 (m, 1H), 3.26-3.11 (m, 1H), 2.66-2.52 (m, 1H), 2.31-2.16 (m, 1H), 1.80-1.09 (series of m, 12H).

Step B: (R/S)-6-((5-(trifluoromethyl)pyridin-2-yl)oxy)-2-azabicyclo[2.2.1]heptane.xHCl. To the title compound of step A (300 mg, 0.84 mmol) in EtOAc (1 mL) was added 4 M HCl in dioxane (5 mL). After 7 h, the reaction was concentrated to give the title compound of step B (243 mg) which was used without further purification. MS (ESI) mass calcd. for $C_{12}H_{13}F_3N_2O$, 258.1. m/z found 259.1 [M+H]+.

Step C: To the title compound of step B (30 mg) and intermediate A-XX (0.10 mmol) in DMF (1 mL) was added DIPEA (0.1 mL, 0.58 mmol) and HATU (38 mg, 0.10 mmol). Upon completion, the reaction was diluted with $H_2O$ and the aqueous layer extracted with EtOAc (3×). The combined organics were washed with $H_2O$, brine, dried with $MgSO_4$, filtered, and concentrated. Purification of the concentrate was performed using Agilent Prep Method X to give the final compound.

Example 7

(R/S)-(2-(2H-1,2,3-triazol-2-yl)phenyl)(6-((5-(trifluoromethyl)pyridin-2-yl)oxy)-2-azabicyclo[2.2.1]heptan-2-yl)methanone

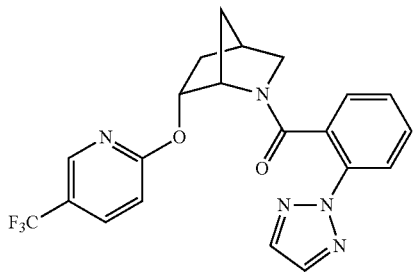 [SMILES: O=C(c1ccccc1-n1nccn1)N1CC2CC(Oc3ccc(C(F)(F)F)cn3)C1C2]

Prepared analogous to Example 5 using intermediate A-1. MS (ESI) mass calcd. for $C_{21}H_{18}F_3N_5O_2$, 429.2. m/z found 430.1 [M+H]+. 1H NMR (400 MHz, Chloroform-d, Compound present as a mixture of rotamers, major rotamer reported) δ 8.02-7.99 (m, 1H), 7.87-7.74 (m, 4H), 7.35-7.29 (m, 1H), 7.03 (dd, J=7.7, 1.5 Hz, 1H), 6.84-6.78 (m, 2H), 5.00 (dt, J=10.1, 3.3 Hz, 1H), 4.07-4.03 (m, 1H), 3.61 (dt, J=11.0, 3.2 Hz, 1H), 3.40 (dd, J=10.9, 1.5 Hz, 1H), 2.65-2.60 (m, 1H), 2.25-2.16 (m, 1H), 1.45-1.37 (m, 2H), 1.33-1.25 (m, 1H).

Example 8

(R/S)-(3-ethoxyisoquinolin-4-yl)(6-((5-(trifluoromethyl)pyridin-2-yl)oxy)-2-azabicyclo[2.2.1]heptan-2-yl)methanone

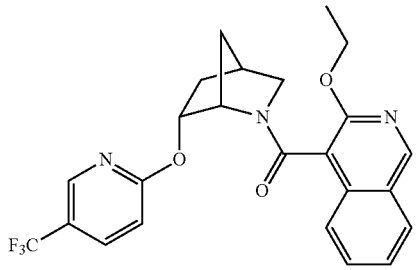 [SMILES: CCOc1ncc2ccccc2c1C(=O)N1CC2CC(Oc3ccc(C(F)(F)F)cn3)C1C2]

Prepared analogous to Example 5 using intermediate A-21 and additional purification using Shimadzu Prep Method X. MS (ESI) mass calcd. for $C_{24}H_{22}F_3N_3O_3$, 457.2. m/z found 458.2 [M+H]+. 1H NMR (400 MHz, Chloroform-d) δ 8.71 (s, 1H), 7.81-7.76 (m, 1H), 7.71-7.68 (m, 1H), 7.61 (d, J=8.2 Hz, 1H), 7.46 (ddd, J=8.4, 6.8, 1.3 Hz, 1H), 7.29-7.23 (buried m, 1H), 7.10 (dd, J=8.7, 2.5 Hz, 1H), 6.11 (d, J=8.6 Hz, 1H), 4.91 (dt, J=10.3, 3.4 Hz, 1H), 4.68-4.66 (m, 1H), 4.65-4.58 (m, 1H), 4.49-4.40 (m, 1H), 3.86 (dt, J=11.2, 3.2 Hz, 1H), 3.58 (dd, J=11.1, 1.7 Hz, 1H), 2.84-2.76 (m, 1H), 2.36-2.24 (m, 1H), 1.99-1.94 (m, 1H), 1.80 (d, J=10.4 Hz, 1H), 1.50 (dt, J=13.7, 3.8 Hz, 1H), 1.44 (t, J=7.1 Hz, 3H).

Example 9

(R/S)-(5-methyl-3-(2H-1,2,3-triazol-2-yl)pyridin-2-yl)(6-((5-(trifluoromethyl)pyridin-2-yl)oxy)-2-azabicyclo[2.2.1]heptan-2-yl)methanone

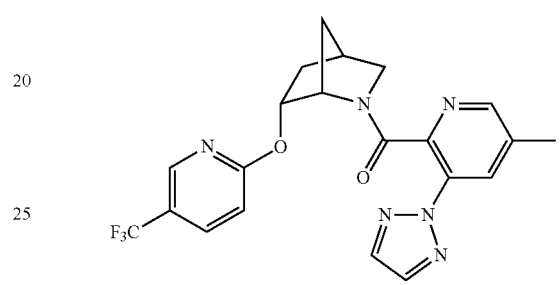

Prepared analogous to Example 5 using intermediate A-19. MS (ESI) mass calcd. for $C_{21}H_{19}F_3N_6O_2$, 444.2. m/z found 445.2 [M+H]+. 1H NMR (400 MHz, Chloroform-d, Compound present as a mixture of rotamers (0.93:0.07), major rotamer reported) δ 7.98-7.95 (m, 1H), 7.95-7.92 (m, 1H), 7.82 (s, 2H), 7.71 (dd, J=8.8, 2.6 Hz, 1H), 7.67-7.64 (m, 1H), 6.88-6.83 (m, 1H), 5.02 (dt, J=10.2, 3.2 Hz, 1H), 4.28-4.21 (m, 1H), 3.68 (dt, J=10.9, 3.2 Hz, 1H), 3.45 (dd, J=11.0, 1.2 Hz, 1H), 2.71-2.64 (m, 1H), 2.28 (s, 3H), 2.28-2.17 (m, 1H), 1.59-1.46 (m, 3H).

Example 10

(R/S)-(7-ethoxyquinolin-8-yl)(6-((5-(trifluoromethyl)pyridin-2-yl)oxy)-2-azabicyclo[2.2.1]heptan-2-yl)methanone

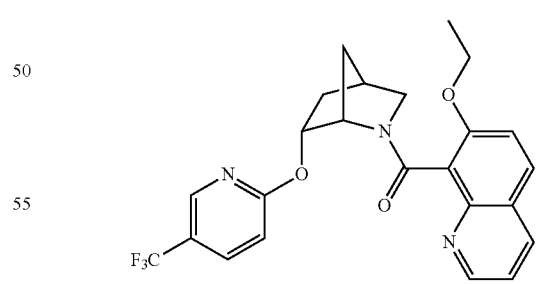

Prepared analogous to Example 5 using intermediate A-25. MS (ESI) mass calcd. for $C_{24}H_{22}F_3N_3O_3$, 457.2. m/z found 458.2 [M+H]+. Analytical HPLC was obtained on a Agilent 1100 Series using a XBridge C18 column (5 um, 100×4.6 mm), mobile phase of 10-100% ACN in 20 mM $NH_4OH$ over 8 min and then hold at 100% ACN for 3 min, at a flow rate of 1 mL/min (Temperature=30° C.). $R_t$=6.49 min (major rotamer) at 254 nm.

Example 11

(R/S)-(3-fluoro-2-(pyrimidin-2-yl)phenyl)(6-((5-(trifluoromethyl)pyridin-2-yl)oxy)-2-azabicyclo[2.2.1]heptan-2-yl)methanone

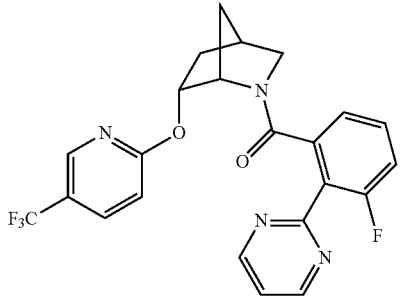 [SMILES: O=C(c1cccc(F)c1-c1ncccn1)N1CC2CC(Oc3ccc(C(F)(F)F)cn3)C1C2]

Prepared analogous to Example 5 using intermediate A-2. MS (ESI) mass calcd. for $C_{23}H_{18}F_4N_4O_2$, 458.1. m/z found 459.2 [M+H]+. $^1$H NMR (400 MHz, Chloroform-d, Compound present as a mixture of rotamers (0.82:0.18), major rotamer reported) δ 8.86 (d, J=4.9 Hz, 2H), 8.14-8.10 (m, 1H), 7.79 (dd, J=8.8, 2.6 Hz, 1H), 7.30-7.26 (m, 1H), 7.10-7.03 (m, 1H), 6.95-6.81 (m, 3H), 5.06 (dt, J=10.2, 3.4 Hz, 1H), 4.27-4.23 (m, 1H), 3.34-3.30 (m, 2H), 2.57-2.51 (m, 1H), 2.25-2.14 (m, 1H), 1.46-1.40 (m, 1H), 1.36 (dt, J=13.6, 3.6 Hz, 1H), 0.94-0.87 (m, 1H).

Example 12

(R/S)-(4-methoxy-2-(pyrimidin-2-yl)phenyl)(6-((5-(trifluoromethyl)pyridin-2-yl)oxy)-2-azabicyclo[2.2.1]heptan-2-yl)methanone

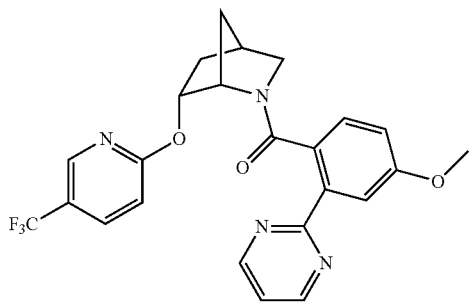 [SMILES: COc1ccc(C(=O)N2CC3CC(Oc4ccc(C(F)(F)F)cn4)C2C3)c(-c2ncccn2)c1]

To the title compound of Example 5 step B (20 mg) and intermediate A-15 (15 mg, 0.066 mmol) was added DCM (0.8 mL) and DIPEA (0.05 mL, 0.29 mmol). T$_3$P (0.11 mL, 0.18 mmol, 50% solution in DMF) was then added dropwise and the mixture heated to 45° C. Upon completion the reaction was quenched with saturated NaHCO$_3$ solution and the aqueous layer extracted with EtOAc (3×). The combined organics were washed saturated NaHCO$_3$ solution, brine, dried with MgSO$_4$, filtered, and concentrated. Purification of the concentrate was performed using Agilent Prep Method X to give the title compound (9.3 mg). MS (ESI) mass calcd. for $C_{24}H_{21}F_3N_4O_3$, 470.2. m/z found 471.2 [M+H]+. $^1$H NMR (400 MHz, Chloroform-d, Compound present as a mixture of rotamers (0.82:0.18), major rotamer reported) δ 8.78 (d, J=4.8 Hz, 2H), 8.11-8.09 (m, 1H), 7.83-7.77 (m, 1H), 7.70 (d, J=2.6 Hz, 1H), 7.20 (t, J=4.9 Hz, 1H), 6.96 (d, J=8.4 Hz, 1H), 6.87-6.80 (m, 1H), 6.45 (dd, J=8.4, 2.7 Hz, 1H), 5.03 (dt, J=10.1, 3.3 Hz, 1H), 4.16-4.12 (m, 1H), 3.81 (s, 3H), 3.62 (dt, J=10.9, 3.2 Hz, 1H), 3.40 (dd, J=10.8, 1.4 Hz, 1H), 2.66-2.60 (m, 1H), 2.26-2.16 (m, 1H), 1.45-1.35 (m, 2H), 1.29-1.17 (m, 1H).

Example 13

(R/S)-4-methoxy-2-(2H-1,2,3-triazol-2-yl)phenyl)(6-((5-(trifluoromethyl)pyridin-2-yl)oxy)-2-azabicyclo[2.2.1]heptan-2-yl)methanone

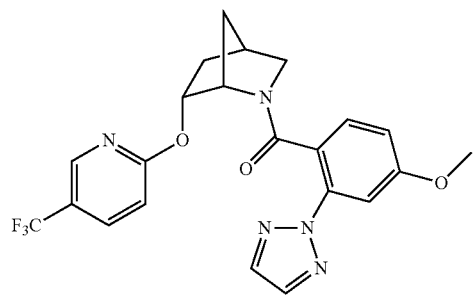 [SMILES: COc1ccc(C(=O)N2CC3CC(Oc4ccc(C(F)(F)F)cn4)C2C3)c(-n2nccn2)c1]

Prepared analogous to Example 5 using intermediate A-5. MS (ESI) mass calcd. for $C_{22}H_{20}F_3N_5O_3$, 459.1. m/z found 460.2 [M+H]+. $^1$H NMR (400 MHz, Chloroform-d, Compound present as a mixture of rotamers (0.88:0.12), major rotamer reported) δ 8.11-8.07 (m, 1H), 7.84-7.75 (m, 3H), 7.37 (d, J=2.5 Hz, 1H), 6.96 (d, J=8.5 Hz, 1H), 6.81 (d, J=8.7 Hz, 1H), 6.37 (dd, J=8.5, 2.5 Hz, 1H), 5.01 (dt, J=10.1, 3.3 Hz, 1H), 4.08-4.01 (m, 1H), 3.80 (s, 3H), 3.58 (dt, J=10.9, 3.2 Hz, 1H), 3.39 (dd, J=10.9, 1.4 Hz, 1H), 2.65-2.58 (m, 1H), 2.25-2.14 (m, 1H), 1.45-1.35 (m, 2H), 1.30-1.22 (m, 1H).

An ORTEP of Example 13 is depicted in FIG. 1.

Example 14

(R/S)-(5-fluoro-2-(2H-1,2,3-triazol-2-yl)phenyl)(6-((5-(trifluoromethyl)pyridin-2-yl)oxy)-2-azabicyclo[2.2.1]heptan-2-yl)methanone

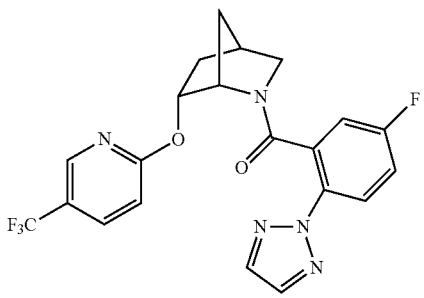 [SMILES: O=C(c1cc(F)ccc1-n1nccn1)N1CC2CC(Oc3ccc(C(F)(F)F)cn3)C1C2]

Prepared analogous to Example 5 using intermediate A-10. MS (ESI) mass calcd. for $C_{21}H_{17}F_4N_5O_2$, 447.1. m/z found 448.1 [M+H]+. $^1$H NMR (400 MHz, Chloroform-d, Compound present as a mixture of rotamers (0.85:0.15), major rotamer reported) δ 8.09-8.05 (m, 1H), 7.85-7.78 (m, 4H), 7.00 (ddd, J=9.0, 7.6, 2.9 Hz, 1H), 6.82 (d, J=8.7 Hz, 1H), 6.78 (dd, J=8.1, 2.9 Hz, 1H), 5.02 (dt, J=10.2, 3.3 Hz, 1H), 4.06-4.01 (m, 1H), 3.59 (dt, J=10.9, 3.2 Hz, 1H), 3.40 (dd, J=10.9, 1.5 Hz, 1H), 2.66-2.60 (m, 1H), 2.28-2.17 (m, 1H), 1.47-1.37 (m, 2H), 1.34-1.27 (m, 1H).

Figure 2:
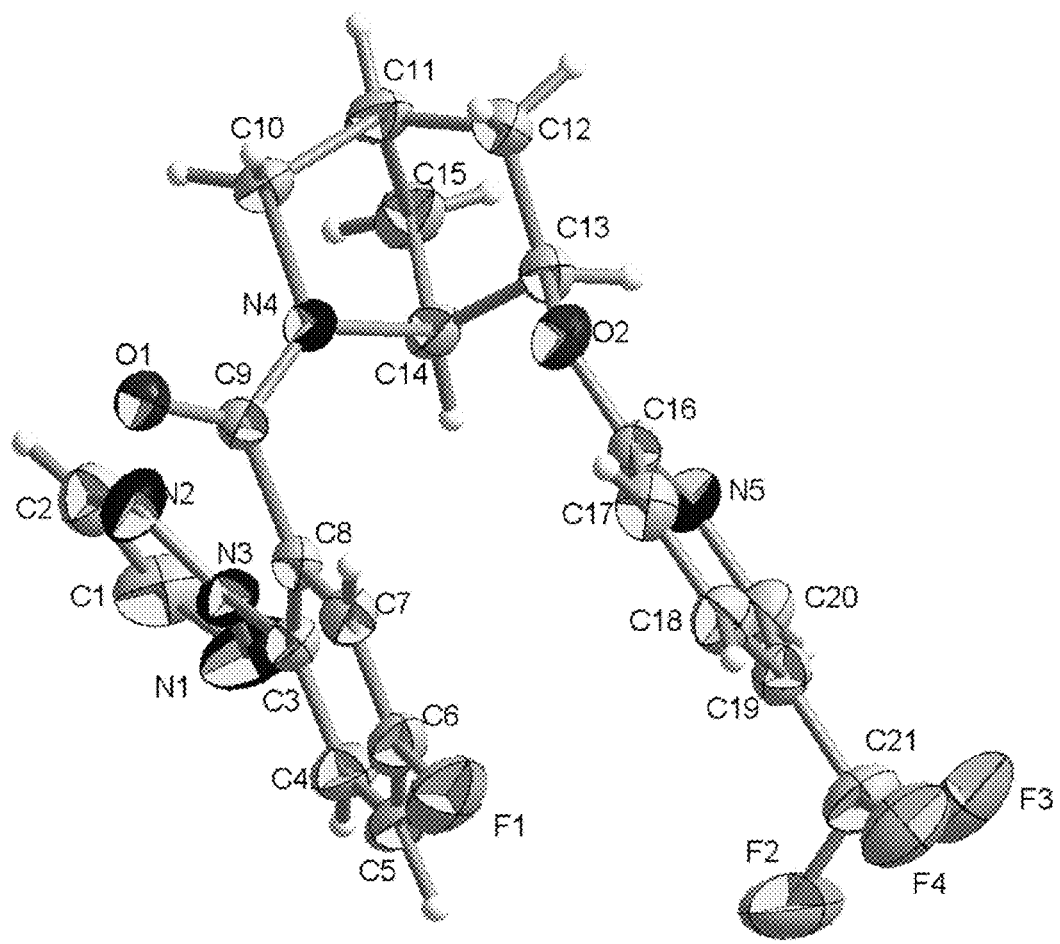
FIG. 2 depicts an ORTEP, shown at 40% probability level, of one embodiment of the invention, Example 14.

An ORTEP of Example 14 is depicted in FIG. 2.

Example 15

(R/S)-2-methoxy-6-(2H-1,2,3-triazol-2-yl)phenyl)(6-((5-(trifluoromethyl)pyridin-2-yl)oxy)-2-azabicyclo[2.2.1]heptan-2-yl)methanone

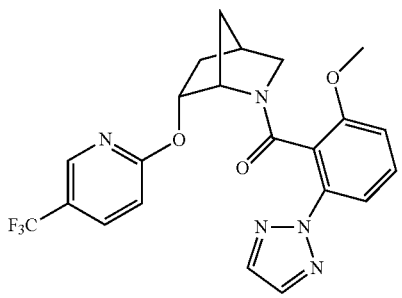 [SMILES: COc1cccc(-n2nccn2)c1C(=O)N1CC2CC(Oc3ccc(C(F)(F)F)cn3)C1C2]

Prepared analogous to Example 5 using intermediate A-13. MS (ESI) mass calcd. for $C_{22}H_{20}F_3N_5O_3$, 459.2. m/z found 460.2 [M+H]$^+$. $^1$H NMR (400 MHz, Chloroform-d, Compound present as a mixture of rotamers, major rotamer reported) δ 8.00-7.95 (m, 1H), 7.82 (s, 2H), 7.73 (d, J=10.6 Hz, 1H), 7.46 (dd, J=8.2, 0.9 Hz, 1H), 7.28-7.21 (m, 1H), 6.75-6.71 (m, 1H), 6.42 (dd, J=8.4, 0.9 Hz, 1H), 4.82 (dt, J=10.2, 3.4 Hz, 1H), 4.18-4.12 (m, 1H), 3.63-3.58 (m, 1H), 3.57 (s, 3H), 3.37 (dd, J=11.0, 1.5 Hz, 1H), 2.58-2.52 (m, 1H), 2.19-2.09 (m, 1H), 1.74-1.66 (m, 1H), 1.45-1.37 (m, 1H), 1.32-1.23 (m, 1H).

Example 16

(R/S)-(3-fluoro-2-(2H-1,2,3-triazol-2-yl)phenyl)(6-((5-(trifluoromethyl)pyridin-2-yl)oxy)-2-azabicyclo[2.2.1]heptan-2-yl)methanone

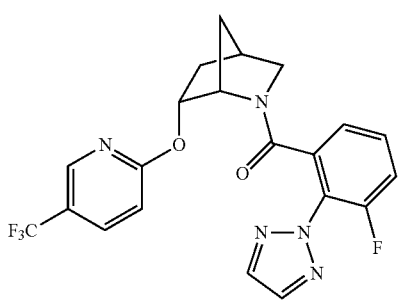 [SMILES: O=C(c1cccc(F)c1-n1nccn1)N1CC2CC(Oc3ccc(C(F)(F)F)cn3)C1C2]

Prepared analogous to Example 5 using intermediate A-16. MS (ESI) mass calcd. for $C_{21}H_{17}F_4N_5O_2$, 447.1. m/z found 448.1[M+H]$^+$. $^1$H NMR (400 MHz, Chloroform-d, Compound present as a mixture of rotamers (0.86:0.14), major rotamer reported) δ 8.14-8.09 (m, 1H), 7.89 (s, 2H), 7.83-7.78 (m, 1H), 7.16 (ddd, J=9.9, 8.1, 1.6 Hz, 1H), 6.98-6.81 (m, 3H), 5.06 (dt, J=10.1, 3.3 Hz, 1H), 4.19-4.15 (m, 1H), 3.38-3.30 (m, 2H), 2.59-2.53 (m, 1H), 2.26-2.16 (m, 1H), 1.50-1.43 (m, 1H), 1.39-1.30 (m, 1H), 1.19-1.10 (m, 1H).

Example 17

(R/S)-(3-methyl-2-(2H-1,2,3-triazol-2-yl)phenyl)(6-((5-(trifluoromethyl)pyridin-2-yl)oxy)-2-azabicyclo[2.2.1]heptan-2-yl)methanone

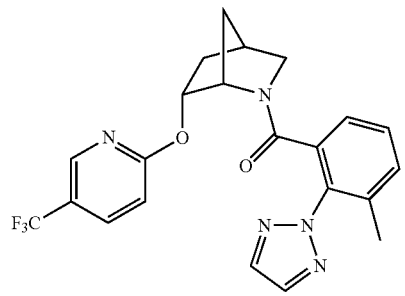 [SMILES: Cc1cccc(C(=O)N2CC3CC(Oc4ccc(C(F)(F)F)cn4)C2C3)c1-n1nccn1]

Prepared analogous to Example 5 using intermediate A-22. MS (ESI) mass calcd. for $C_{22}H_{20}F_3N_5O_2$, 443.2. m/z found 444.2 [M+H]$^+$. $^1$H NMR (400 MHz, Chloroform-d, Compound present as a mixture of rotamers (0.85:0.15), major rotamer reported) δ 8.15-8.11 (m, 1H), 7.86-7.77 (m, 3H), 7.24-7.19 (m, 1H), 6.99-6.82 (m, 3H), 5.09 (dt, J=10.1, 3.3 Hz, 1H), 4.25-4.19 (m, 1H), 3.31-3.23 (m, 2H), 2.57-2.50 (m, 1H), 2.27-2.11 (m, 4H), 1.53-1.47 (m, 1H), 1.37-1.28 (m, 1H), 1.27-1.21 (m, 1H).

Example 18

(R/S)-(2-fluoro-6-(2H-1,2,3-triazol-2-yl)phenyl)(6-((5-(trifluoromethyl)pyridin-2-yl)oxy)-2-azabicyclo[2.2.1]heptan-2-yl)methanone

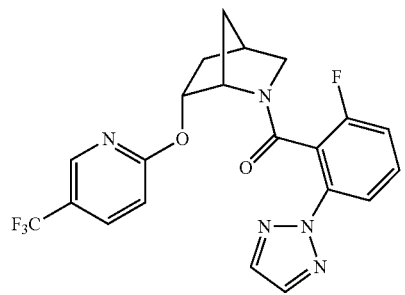 [SMILES: O=C(c1c(F)cccc1-n1nccn1)N1CC2CC(Oc3ccc(C(F)(F)F)cn3)C1C2]

Prepared analogous to Example 5 using intermediate A-11. MS (ESI) mass calcd. for $C_{21}H_{17}F_4N_5O_2$, 447.1. m/z found 448.1 [M+H]$^+$. $^1$H NMR (400 MHz, Chloroform-d, Compound present as a mixture of rotamers, major rotamer reported) δ 8.04-8.02 (m, 1H), 7.85-7.72 (m, 4H), 7.32-7.26 (m, 1H), 6.92-6.88 (m, 1H), 6.61 (td, J=8.4, 1.0 Hz, 1H), 5.00-4.94 (m, 1H), 4.03-4.00 (m, 1H), 3.65 (dt, J=11.0, 3.2 Hz, 1H), 3.44 (dd, J=10.9, 1.5 Hz, 1H), 2.68-2.60 (m, 1H), 2.28-2.17 (m, 1H), 1.46-1.37 (m, 2H), 1.31-1.25 (m, 1H).

Example 19

(R/S)-(5-fluoro-2-(pyrimidin-2-yl)phenyl)(6-((5-(trifluoromethyl)pyridin-2-yl)oxy)-2-azabicyclo[2.2.1]heptan-2-yl)methanone

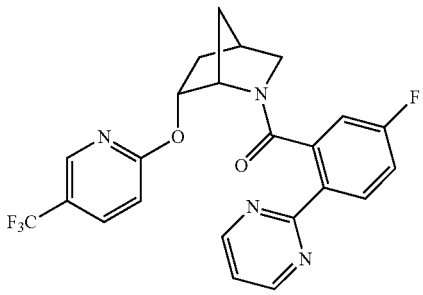 [SMILES: O=C(c1cc(F)ccc1-c1ncccn1)N1CC2CC(Oc3ccc(C(F)(F)F)cn3)C1C2]

Prepared analogous to Example 5 using intermediate A-7. MS (ESI) mass calcd. for $C_{23}H_{18}F_4N_4O_2$, 458.1. m/z found 459.2 [M+H]$^+$. $^1$H NMR (400 MHz, Chloroform-d, Compound present as a mixture of rotamers (0.88:0.12), major rotamer reported) δ 8.77 (d, J=4.9 Hz, 2H), 8.22 (dd, J=8.8, 5.6 Hz, 1H), 8.11-8.06 (m, 1H), 7.82 (dd, J=8.7, 2.5 Hz, 1H), 7.19 (t, J=4.9 Hz, 1H), 6.98 (ddd, J=8.8, 7.9, 2.7 Hz, 1H), 6.85 (d, J=8.8 Hz, 1H), 6.77 (dd, J=8.6, 2.7 Hz, 1H), 5.03 (dt, J=10.1, 3.4 Hz, 1H), 4.16-4.11 (m, 1H), 3.66 (dt, J=10.8, 3.2 Hz, 1H), 3.42 (dd, J=10.8, 1.5 Hz, 1H), 2.70-2.63 (m, 1H), 2.30-2.19 (m, 1H), 1.50-1.39 (m, 2H), 1.35-1.27 (m, 1H).

Example 20

(R/S)-(4-fluoro-2-(pyrimidin-2-yl)phenyl)(-6-((5-(trifluoromethyl)pyridin-2-yl)oxy)-2-azabicyclo[2.2.1]heptan-2-yl)methanone Prepared analogous to Example 5 using intermediate A-23. MS (ESI) mass calcd. for $C_{23}H_{18}F_4N_4O_2$, 458.1. m/z found 459.2 [M+H]$^+$. $^1$H NMR (400 MHz, Chloroform-d, Compound present as a mixture of rotamers (0.84:0.16), major rotamer reported) δ 8.80 (d, J=4.8 Hz, 2H), 8.12-8.09 (m, 1H), 7.93 (dd, J=9.9, 2.6 Hz, 1H), 7.83-7.78 (m, 1H), 7.25-7.21 (m, 1H), 7.01 (dd, J=8.4, 5.6 Hz, 1H), 6.85-6.81 (m, 1H), 6.63-6.55 (m, 1H), 5.03 (dt, J=10.1, 3.3 Hz, 1H), 4.16-4.09 (m, 1H), 3.65 (dt, J=10.8, 3.3 Hz, 1H), 3.46-3.36 (m, 1H), 2.69-2.62 (m, 1H), 2.29-2.17 (m, 1H), 1.48-1.37 (m, 2H), 1.31-1.23 (m, 1H).

Example 21

(R/S)-(2-(4H-1,2,4-triazol-4-yl)phenyl)(6-((5-(trifluoromethyl)pyridin-2-yl)oxy)-2-azabicyclo[2.2.1]heptan-2-yl)methanone

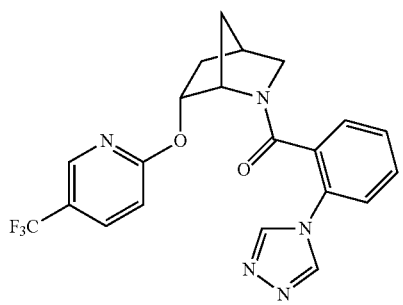 [SMILES: O=C(c1ccccc1-n1cnnc1)N1CC2CC(Oc3ccc(C(F)(F)F)cn3)C1C2]

Prepared analogous to Example 5 using intermediate A-9. MS (ESI) mass calcd. for $C_{21}H_{18}F_3N_5O_2$, 429.1. m/z found 430.2 [M+H]$^+$. $^1$H NMR (400 MHz, Chloroform-d, Compound present as a mixture of rotamers (0.84:0.16), major rotamer reported) δ 8.44 (s, 2H), 8.03-7.95 (m, 1H), 7.80 (dd, J=8.9, 2.5 Hz, 1H), 7.44-7.34 (m, 1H), 7.30-7.24 (m, 1H), 7.08-6.92 (m, 2H), 6.83 (d, J=8.7 Hz, 1H), 5.04-4.94 (m, 1H), 3.90 (br.s, 1H), 3.47-3.32 (m, 2H), 2.65-2.57 (m, 1H), 2.26-2.13 (m, 1H), 1.52-1.33 (m, 2H), 1.05-0.86 (m, 1H).

Example 22

(R/S)-(6-methyl-3-(2H-1,2,3-triazol-2-yl)pyridin-2-yl)(6-((5-(trifluoromethyl)pyridin-2-yl)oxy)-2-azabicyclo[2.2.1]heptan-2-yl)methanone

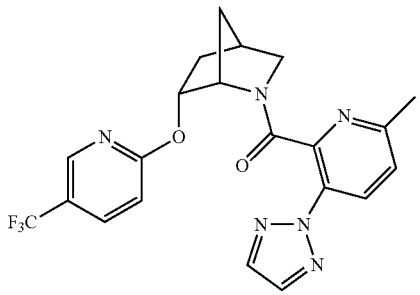 [SMILES: Cc1ccc(-n2nccn2)c(C(=O)N2CC3CC(Oc4ccc(C(F)(F)F)cn4)C2C3)n1]

Prepared analogous to Example 5 using intermediate A-20. MS (ESI) mass calcd. for $C_{21}H_{19}F_3N_6O_2$, 444.2. m/z found 445.1 [M+H]$^+$. $^1$H NMR (400 MHz, Chloroform-d, Compound present as a mixture of rotamers (0.82:0.18), major rotamer reported) δ 8.05-7.98 (m, 2H), 7.83 (s, 2H), 7.71-7.66 (m, 1H), 7.10-7.05 (m, 1H), 6.86-6.80 (m, 1H), 5.01-4.93 (m, 1H), 4.28-4.22 (m, 1H), 3.68 (dt, J=10.9, 3.2 Hz, 1H), 3.46 (dd, J=10.9, 1.2 Hz, 1H), 2.67-2.62 (m, 1H), 2.28-2.16 (m, 4H), 1.53-1.42 (m, 3H).

Example 23

(6-methyl-3-(2H-1,2,3-triazol-2-yl)pyridin-2-yl)((1R,4S,6S)-6-((5-(trifluoromethyl)pyridin-2-yl)oxy)-2-azabicyclo[2.2.1]heptan-2-yl)methanone

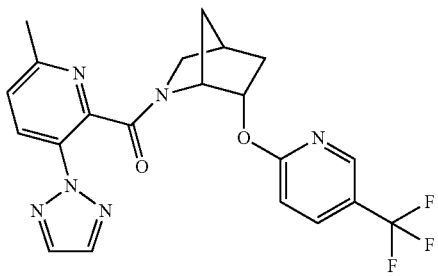 [SMILES: Cc1ccc(-n2nccn2)c(C(=O)N2CC3CC(Oc4ccc(C(F)(F)F)cn4)C2C3)n1]

The title compound, absolute configuration confirmed by Example 25, was obtained as a single enantiomer by Chiral SFC purification of Example 22 performed using a Chiralpak IC column (5 um 250×21 mm), mobile phase of 20% EtOH: 80% $CO_2$, and a flow rate of 40 mL/min (Temperature=40° C.). Elution was monitored following absorbance at 270 nm. The enantiomeric purity was confirmed by analytical SFC using a Chiralpak IC column (5 um 250×4.6 mm), mobile phase of 20% EtOH: 80% $CO_2$, and a flow rate of 2 mL/min over 45 minutes (Temperature=40° C.). Elution was monitored following absorbance at 270 nm. (enantiopurity >98%) which elutes as two peaks with an initial minor peak followed by a second major peak (due to rotamers), 6.77 min and 23.40 min retention time). MS (ESI) mass calcd. for $C_{21}H_{19}F_3N_6O_2$, 444.2. m/z found 445.2 $[M+H]^+$. $^1H$ NMR data is in agreement with Example 22.

Example 24

(6-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone

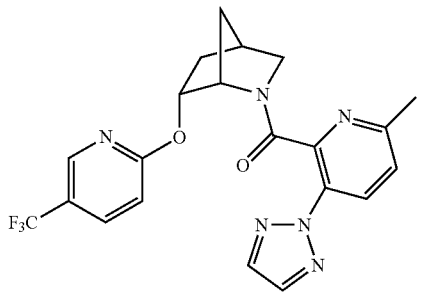 [SMILES: Cc1ccc(-n2nccn2)c(C(=O)N2CC3CC(Oc4ccc(C(F)(F)F)cn4)C2C3)n1]

The title compound, absolute configuration confirmed by Example 25, was obtained as a single enantiomer by Chiral SFC purification of Example 22 performed using a Chiralpak IC column (5 um 250×21 mm), mobile phase of 20% EtOH: 80% $CO_2$, and a flow rate of 40 mL/min (Temperature=40° C.). Elution was monitored following absorbance at 270 nm. The enantiomeric purity was confirmed by analytical SFC using a Chiralpak IC column (5 um 250×4.6 mm), mobile phase of 20% EtOH: 80% $CO_2$, and a flow rate of 2 mL/min over 45 minutes (Temperature=40° C.). Elution was monitored following absorbance at 270 nm. (enantiopurity >98%) which elutes as two peaks with an initial minor peak followed by a second major peak (due to rotamers), 7.75 min and 11.79 min retention time). MS (ESI) mass calcd. for $C_{21}H_{19}F_3N_6O_2$, 444.2. m/z found 445.2 $[M+H]^+$. $^1H$ NMR data is in agreement with Example 22.

Example 25

(6-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone

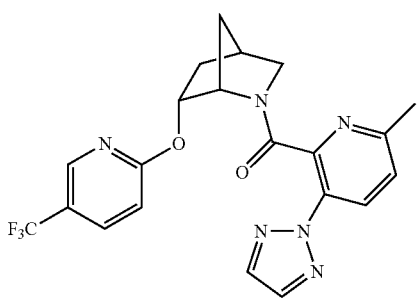 [SMILES: Cc1ccc(-n2nccn2)c(C(=O)N2CC3CC(Oc4ccc(C(F)(F)F)cn4)C2C3)n1]

Step A: (1 S,4R,6R)-tert-butyl 6-((5-(trifluoromethyl)pyridin-2-yl)oxy)-2-azabicyclo[2.2.1]heptane-2-carboxylate. To intermediate B-5 (422 mg, 1.98 mmol) dissolved in DMF (8 mL) was added NaH (119 mg, 2.97 mmol, 60% dispersion in mineral oil). After 5 minutes 2-chloro-5-(trifluoromethyl)pyridine (718 mg, 3.96 mmol) was then added and the mixture heated to 80° C. After heating at 80° C. for 4.75 h, the mixture was cooled to room temperature, quenched with saturated $NH_4Cl$ solution, diluted with $H_2O$, and the aqueous layer extracted with EtOAc (3×). The combined organics were washed with $H_2O$, brine, dried with $MgSO_4$, filtered and concentrated. Purification via silica gel chromatography (0-25% EtOAc in hexanes) gave the title compound (622 mg, 1.74 mmol, 88%). MS (ESI) mass calcd. for $C_{12}H_{21}F_3N_2O_3$, 358.2. m/z found 359.2 $[M+H]^+$. $^1H$ NMR (400 MHz, Chloroform-d, compound present as a mixture of rotamers (0.75:0.25)) δ 8.44-8.37 (m, 1H), 7.80-7.74 (m, 0.75H), 7.73-7.66 (m, 0.25H), 6.82-6.77 (m, 0.75H), 6.73-6.68 (m, 0.25H), 5.44-5.37 (m, 0.25H), 5.34 (dt, J=10.1, 3.2 Hz, 0.75H), 4.58-4.53 (m, 1H), 3.44-3.34 (m, 1H), 3.20 (dd, J=9.6, 1.3 Hz, 0.75H), 3.13 (d, J=9.5 Hz, 0.25H), 2.61-2.52 (m, 1H), 2.29-2.15 (m, 1H), 1.79-1.58 (m, 2H), 1.47-1.23 (m, 3H), 1.12 (s, 7H).

Step B: (1S,4R,6R)-6-((5-(trifluoromethyl)pyridin-2-yl)oxy)-2-azabicyclo[2.2.1]heptane.xHCl. To the title compound of step A (622 mg, 1.74 mmol) in EtOAc (1 mL) was added 4M HCl in dioxane (10 mL). After 2 h, the reaction was concentrated to give the title compound of step B (507 mg) which was used without further purification. MS (ESI) mass calcd. for $C_{12}H_{13}F_3N_2O$, 258.1. m/z found 259.1 $[M+H]^+$.

Step C: (6-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone To the title compound of step B (100 mg) and intermediate A-20 (84 mg, 0.37 mmol) in DMF (4 mL) was added DIPEA (0.3 mL, 1.74 mmol) and HATU (142 mg, 0.37 mmol). Upon completion, the reaction was diluted with $H_2O$ and the aqueous layer extracted with EtOAc (3×). The combined organics were washed with H₂O, brine, dried with MgSO₄, filtered, and concentrated. Purification of the concentrate was performed using Agilent Prep Method X to give the title compound (112 mg). The enantiomeric purity was confirmed by analytical SFC using a Chiralpak IC column (5 um 250×4.6 mm), mobile phase of 20% EtOH: 80% CO₂, and a flow rate of 2 mL/min over 45 minutes (Temperature=40° C.). Elution was monitored following absorbance at 270 nm. (100% single enantiomer) which elutes as two peaks with an initial minor peak followed by a second major peak (due to rotamers), 7.69 min and 11.90 min retention time). MS (ESI) mass calcd. for $C_{21}H_{19}F_3N_6O_2$, 444.2. m/z found 445.2 [M+H]⁺. ¹H NMR data is in agreement with Example 22.

Example 26

(4-fluoro-2-(pyrimidin-2-yl)phenyl)((1S,4R,6R)-6-((5-(trifluoromethyl)pyridin-2-yl)oxy)-2-azabicyclo[2.2.1]heptan-2-yl)methanone

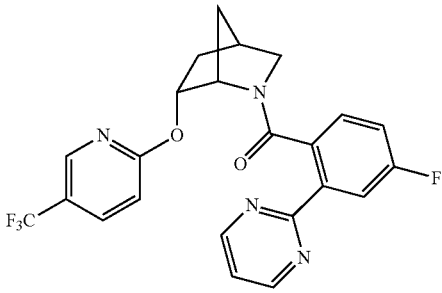 [SMILES: O=C(c1ccc(F)cc1-c1ncccn1)N1CC2CC(Oc3ccc(C(F)(F)F)cn3)C1C2]

Prepared analogous to Example 25 substituting intermediate A-20 with intermediate A-23. MS (ESI) mass calcd. for $C_{23}H_{18}F_4N_4O_2$, 458.1. m/z found 459.1 [M+H]⁺. ¹H NMR (400 MHz, Chloroform-d, Compound present as a mixture of rotamers (0.85:0.15), major rotamer reported) δ 8.80 (d, J=4.8 Hz, 2H), 8.13-8.07 (m, 1H), 7.95-7.90 (m, 1H), 7.84-7.78 (m, 1H), 7.23 (t, J=4.8 Hz, 1H), 7.01 (dd, J=8.4, 5.6 Hz, 1H), 6.87-6.81 (m, 1H), 6.59 (ddd, J=8.5, 7.9, 2.7 Hz, 1H), 5.03 (dt, J=10.1, 3.3 Hz, 1H), 4.15-4.10 (m, 1H), 3.65 (dt, J=10.8, 3.2 Hz, 1H), 3.44-3.38 (m, 1H), 2.69-2.62 (m, 1H), 2.29-2.18 (m, 1H), 1.48-1.37 (m, 2H), 1.34-1.23 (m, 1H).

Example 27

(3-fluoro-2-(pyrimidin-2-yl)phenyl)((1S,4R,6R)-6-((5-(trifluoromethyl)pyridin-2-yl)oxy)-2-azabicyclo[2.2.1]heptan-2-yl)methanone

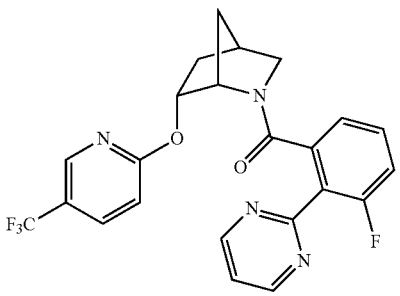 [SMILES: O=C(c1cccc(F)c1-c1ncccn1)N1CC2CC(Oc3ccc(C(F)(F)F)cn3)C1C2]

Prepared analogous to Example 25 substituting intermediate A-20 with intermediate A-2. MS (ESI) mass calcd. for $C_{23}H_{18}F_4N_4O_2$, 458.1. m/z found 459.2 [M+H]⁺. ¹H NMR (400 MHz, Chloroform-d, Compound present as a mixture of rotamers (0.88:0.12), major rotamer reported) δ 8.86 (d, J=4.9 Hz, 2H), 8.14-8.08 (m, 1H), 7.79 (dd, J=8.8, 2.5 Hz, 1H), 7.30-7.26 (m, 1H), 7.10-7.02 (m, 1H), 6.95-6.80 (m, 3H), 5.06 (dt, J=10.3, 3.4 Hz, 1H), 4.28-4.22 (m, 1H), 3.34-3.30 (m, 2H), 2.56-2.51 (m, 1H), 2.25-2.15 (m, 1H), 1.45-1.40 (m, 1H), 1.36 (dt, J=13.6, 3.6 Hz, 1H), 0.95-0.86 (m, 1H).

Example 28

(5-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone

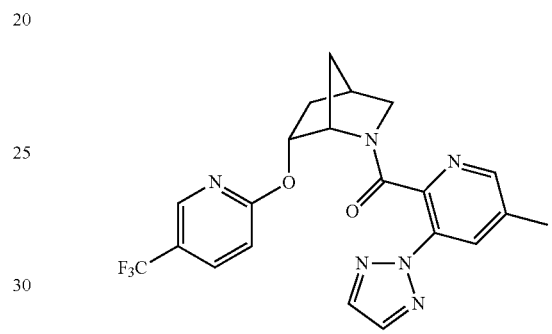

Prepared analogous to Example 25 substituting intermediate A-20 with intermediate A-19. MS (ESI) mass calcd. for $C_{21}H_{19}F_3N_6O_2$, 444.2. m/z found 445.2 [M+H]⁺. ¹H NMR (400 MHz, Chloroform-d, Compound present as a mixture of rotamers (0.86:0.14), major rotamer reported) δ 7.98-7.92 (m, 2H), 7.83 (s, 2H), 7.75-7.69 (m, 1H), 7.67-7.63 (m, 1H), 6.89-6.83 (m, 1H), 5.02 (dt, J=10.3, 3.2 Hz, 1H), 4.27-4.21 (m, 1H), 3.69 (dt, J=10.9, 3.2 Hz, 1H), 3.51-3.42 (m, 1H), 2.70-2.64 (m, 1H), 2.33-2.16 (m, 4H), 1.58-1.46 (m, 3H).

Example 29

(6-methyl-2-(2H-1,2,3-triazol-2-yl)pyridin-3-yl)((1S,4R,6R)-6-((5-(trifluoromethyl)pyridin-2-yl)oxy)-2-azabicyclo[2.2.1]heptan-2-yl)methanone

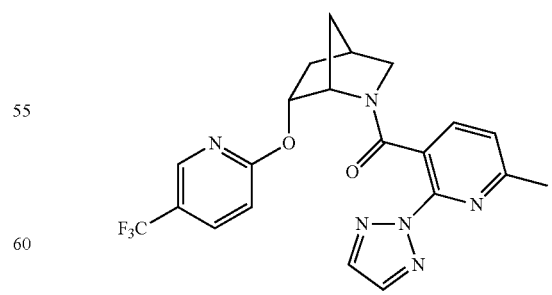

Prepared analogous to Example 25 substituting intermediate A-20 with intermediate A-3. MS (ESI) mass calcd. $C_{21}H_{19}F_3N_6O_2$, 444.2. m/z found 445.2 [M+H]⁺. ¹H NMR (400 MHz, Chloroform-d, Compound present as a mixture of rotamers (0.83:0.17), major rotamer reported) δ 8.06-8.02 (m, 1H), 7.88 (s, 2H), 7.80 (dd, J=8.7, 2.5 Hz, 1H), 7.31-7.24 (m, 1H), 6.82 (d, J=8.7 Hz, 1H), 6.61 (d, J=7.8 Hz, 1H), 4.98 (dt, J=10.1, 3.3 Hz, 1H), 4.06-4.02 (m, 1H), 3.62 (dt, J=11.0, 3.2 Hz, 1H), 3.41 (dd, J=10.9, 1.5 Hz, 1H), 2.68-2.61 (m, 1H), 2.56 (s, 3H), 2.27-2.14 (m, 1H), 1.48-1.40 (m, 2H), 1.37-1.29 (m, 1H).

Example 30

(3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone

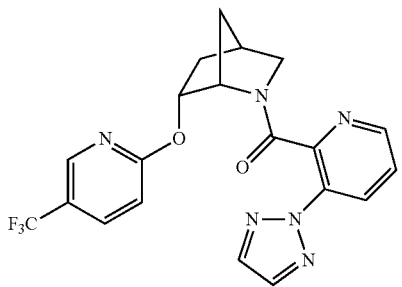 [SMILES: O=C(c1ncccc1-n1nccn1)N1CC2CC(Oc3ccc(C(F)(F)F)cn3)C1C2]

Prepared analogous to Example 25 substituting intermediate A-20 with intermediate A-28. MS (ESI) mass calcd. $C_{20}H_{17}F_3N_6O_2$, 430.1. m/z found 431.2 [M+H]$^+$. $^1$H NMR (400 MHz, Chloroform-d, Compound present as a mixture of rotamers (0.80:0.20), major rotamer reported) δ 8.17 (dd, J=8.4, 1.5 Hz, 1H), 7.95-7.91 (m, 1H), 7.88-7.81 (m, 3H), 7.72 (dd, J=8.7, 2.6 Hz, 1H), 7.20 (dd, J=8.3, 4.7 Hz, 1H), 6.86 (d, J=8.8 Hz, 1H), 5.03 (dt, J=10.2, 3.2 Hz, 1H), 4.27-4.23 (m, 1H), 3.74-3.68 (m, 1H), 3.47 (dd, J=11.0, 1.3 Hz, 1H), 2.71-2.66 (m, 1H), 2.29-2.19 (m, 1H), 1.64-1.48 (m, 3H).

Example 31

(3-fluoro-2-methoxyphenyl)((1S,4R,6R)-6-((5-(trifluoromethyl)pyridin-2-yl)oxy)-2-azabicyclo[2.2.1]heptan-2-yl)methanone

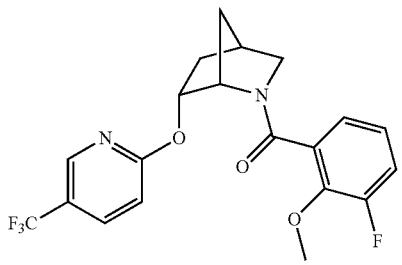 [SMILES: COc1c(F)cccc1C(=O)N1CC2CC(Oc3ccc(C(F)(F)F)cn3)C1C2]

Prepared analogous to Example 25 substituting intermediate A-20 with intermediate A-18. MS (ESI) mass calcd. $C_{20}H_{18}F_4N_2O_3$, 410.1. m/z found 411.1 [M+H]$^+$. $^1$H NMR (400 MHz, Chloroform-d, Compound present as a mixture of rotamers (0.83:0.17), major rotamer reported) δ 8.01-7.97 (m, 1H), 7.74-7.71 (m, 1H), 6.92 (ddd, J=11.5, 8.1, 1.7 Hz, 1H), 6.79 (d, 8.7 Hz, 1H), 6.67-6.49 (m, 2H), 5.07 (dt, J=10.1, 3.2 Hz, 1H), 4.43-4.38 (m, 1H), 3.90 (d, J=1.7 Hz, 3H), 3.69 (dt, J=11.1, 3.3 Hz, 1H), 3.45 (dd, J=11.1, 1.5 Hz, 1H), 2.76-2.70 (m, 1H), 2.33-2.21 (m, 1H), 1.90-1.83 (m, 1H), 1.75-1.69 (m, 1H), 1.44 (dt, J=13.5, 3.6 Hz, 1H).

Example 32

(3-methyl-2-(oxazol-2-yl)phenyl)((1S,4R,6R)-6-((5-(trifluoromethyl)pyridin-2-yl)oxy)-2-azabicyclo[2.2.1]heptan-2-yl)methanone

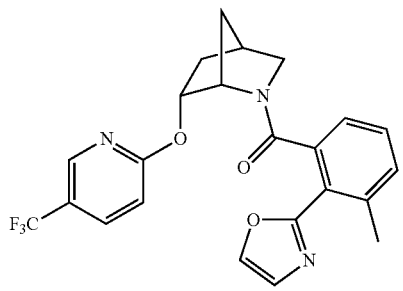

Prepared analogous to Example 25 substituting intermediate A-20 with intermediate A-27. MS (ESI) mass calcd. $C_{23}H_{20}F_3N_3O_3$, 443.1. m/z found 444.2 [M+H]$^+$. $^1$H NMR (400 MHz, Chloroform-d, Compound present as a mixture of rotamers (0.81:0.19), major rotamer reported) δ 8.07-8.03 (m, 1H), 7.81-7.73 (m, 2H), 7.30-7.25 (m, 1H), 7.18-7.13 (m, 1H), 6.91-6.80 (m, 3H), 5.04 (dt, J=10.2, 3.2 Hz, 1H), 4.22-4.17 (m, 1H), 3.49-3.41 (m, 1H), 3.40-3.33 (m, 1H), 2.63-2.57 (m, 1H), 2.44 (s, 3H), 2.26-2.16 (m, 1H), 1.49 (d, J=10.4 Hz, 1H), 1.41-1.26 (m, 2H).

Example 33

(3-fluoro-2-(1H-1,2,3-triazol-1-yl)phenyl)((1S,4R,6R)-6-((5-(trifluoromethyl)pyridin-2-yl)oxy)-2-azabicyclo[2.2.1]heptan-2-yl)methanone

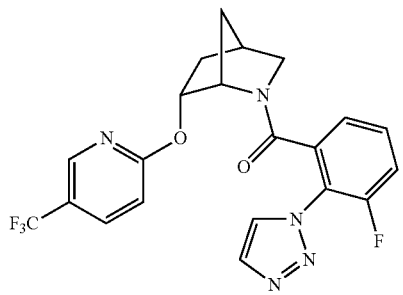 [SMILES: O=C(c1cccc(F)c1-n1ccnn1)N1CC2CC(Oc3ccc(C(F)(F)F)cn3)C1C2]

Prepared analogous to Example 25 substituting intermediate A-20 with intermediate A-33. MS (ESI) mass calcd. $C_{21}H_{17}F_4N_5O_2$, 447.1. m/z found 448.2 [M+H]$^+$. $^1$H NMR (400 MHz, Chloroform-d, Compound present as a mixture of rotamers (0.76:0.24), major rotamer reported) δ 8.20-8.15 (m, 1H), 7.92-7.88 (m, 1H), 7.87-7.80 (m, 2H), 7.24-7.16 (m, 1H), 7.07-6.99 (m, 1H), 6.92-6.85 (m, 2H), 5.14 (dt, J=9.9, 3.2 Hz, 1H), 4.28-4.24 (m, 1H), 3.37-3.31 (m, 1H), 3.30-3.24 (m, 1H), 2.62-2.56 (m, 1H), 2.32-2.21 (m, 1H), 1.42-1.31 (m, 2H), 0.94-0.89 (m, 1H).

Example 34

(6-methyl-2-(1H-1,2,3-triazol-1-yl)pyridin-3-yl)((1S,4R,6R)-6-((5-(trifluoromethyl)pyridin-2-yl)oxy)-2-azabicyclo[2.2.1]heptan-2-yl)methanone

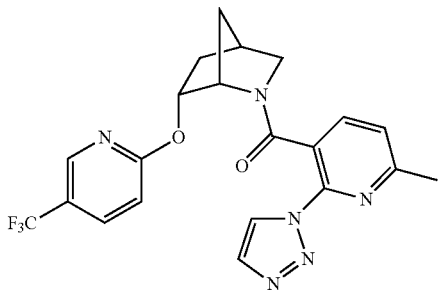 [SMILES: Cc1ccc(C(=O)N2CC3CC(Oc4ccc(C(F)(F)F)cn4)C2C3)c(-n2ccnn2)n1]

Prepared analogous to Example 25 substituting intermediate A-20 with intermediate A-4. MS (ESI) mass calcd. $C_{21}H_{19}F_3N_6O_2$, 444.2. m/z found 445.2 [M+H]$^+$. $^1$H NMR (400 MHz, Chloroform-d, Compound present as a mixture of rotamers (0.87:0.13), major rotamer reported) δ 8.44 (d, J=1.2 Hz, 1H), 8.09-8.05 (m, 1H), 7.84-7.78 (m, 2H), 7.28 (d, J=7.8 Hz, 1H), 6.88-6.83 (m, 1H), 6.65 (d, J=7.8 Hz, 1H), 5.05 (dt, J=10.1, 3.3 Hz, 1H), 4.13-4.06 (m, 1H), 3.73 (dt, J=11.0, 3.2 Hz, 1H), 3.38 (dd, J=10.9, 1.5 Hz, 1H), 2.72-2.65 (m, 1H), 2.50 (s, 3H), 2.31-2.21 (m, 1H), 1.73-1.67 (m, 1H), 1.51-1.40 (m, 2H).

Example 35

(3-fluoro-2-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone

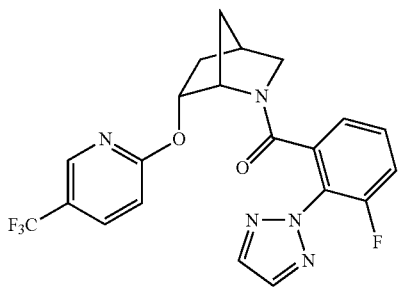

Prepared analogous to Example 25 substituting intermediate A-20 with intermediate A-16. MS (ESI) mass calcd. $C_{21}H_{17}F_4N_5O_2$, 447.1. m/z found 448.2 [M+H]$^+$. $^1$H NMR (400 MHz, Chloroform-d, Compound present as a mixture of rotamers (0.85:0.15), major rotamer reported) δ 8.14-8.08 (m, 1H), 7.89 (s, 2H), 7.80 (dd, J=8.7, 2.5 Hz, 1H), 7.16 (ddd, J=9.9, 8.2, 1.6 Hz, 1H), 6.98-6.81 (m, 3H), 5.06 (dt, J=10.1, 3.3 Hz, 1H), 4.21-4.13 (m, 1H), 3.39-3.30 (m, 2H), 2.60-2.52 (m, 1H), 2.26-2.15 (m, 1H), 1.51-1.43 (m, 1H), 1.39-1.30 (m, 1H), 1.20-1.10 (m, 1H).

Example 36

(2-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone

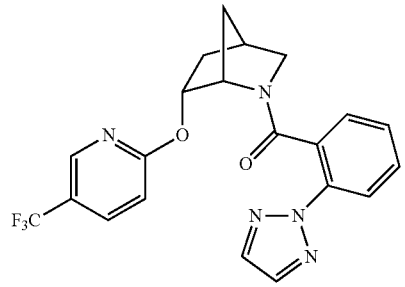

Prepared analogous to Example 25 substituting intermediate A-20 with intermediate A-1. MS (ESI) mass calcd. $C_{21}H_{18}F_3N_5O_2$, 429.1. m/z found 430.2 [M+H]$^+$. $^1$H NMR (400 MHz, Chloroform-d, Compound present as a mixture of rotamers (0.87:0.13), major rotamer reported) δ 8.04-7.98 (m, 1H), 7.89-7.74 (m, 4H), 7.36-7.28 (m, 1H), 7.02 (dd, J=7.7, 1.5 Hz, 1H), 6.85-6.77 (m, 2H), 4.99 (dt, J=10.2, 3.3 Hz, 1H), 4.10-4.00 (m, 1H), 3.61 (dt, J=10.9, 3.3 Hz, 1H), 3.40 (dd, J=10.9, 1.5 Hz, 1H), 2.67-2.58 (m, 1H), 2.26-2.15 (m, 1H), 1.47-1.23 (m, 3H).

Example 37

(3-ethoxy-6-methylpyridin-2-yl)((1S,4R,6R)-6-((5-(trifluoromethyl)pyridin-2-yl)oxy)-2-azabicyclo[2.2.1]heptan-2-yl)methanone

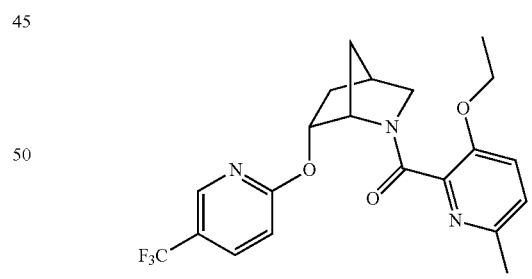

Prepared analogous to Example 25 substituting intermediate A-20 with intermediate A-8. MS (ESI) mass calcd. $C_{21}H_{22}F_3N_3O_3$, 421.2. m/z found 422.2 [M+H]$^+$. $^1$H NMR (400 MHz, Chloroform-d, Compound present as a mixture of rotamers (0.83:0.17), major rotamer reported) δ 7.92-7.88 (m, 1H), 7.71-7.66 (m, 1H), 6.92 (d, J=8.5 Hz, 1H), 6.87-6.82 (m, 2H), 5.00 (dt, J=10.2, 3.3 Hz, 1H), 4.68-4.63 (m, 1H), 4.05-3.85 (m, 2H), 3.72 (dt, J=11.0, 3.2 Hz, 1H), 3.51 (dd, J=11.0, 1.6 Hz, 1H), 2.74-2.68 (m, 1H), 2.31-2.16 (m, 4H), 1.96-1.88 (m, 1H), 1.78-1.70 (m, 1H), 1.48 (dt, J=13.5, 3.6 Hz, 1H), 1.43-1.35 (m, 3H).

Example 38

(2-fluoro-6-(pyrimidin-2-yl)phenyl)((1S,4R,6R)-6-((5-(trifluoromethyl)pyridin-2-yl)oxy)-2-azabicyclo[2.2.1]heptan-2-yl)methanone

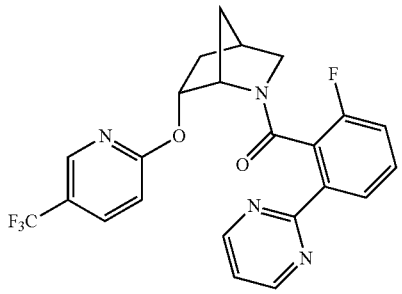 [SMILES: O=C(c1c(F)cccc1-c1ncccn1)N1CC2CC(Oc3ccc(C(F)(F)F)cn3)C1C2]

Prepared analogous to Example 25 substituting intermediate A-20 with intermediate A-6 and substituting purification by Agilent Prep Method X by silica gel chromatography (15-80% EtOAc (with 10% MeOH) in hexanes). MS (ESI) mass calcd. $C_{23}H_{18}F_4N_4O_2$, 458.1. m/z found 459.1 [M+H]$^+$. $^1$H NMR (500 MHz, Chloroform-d, Compound present as a mixture of rotamers (0.78:0.22), major rotamer reported) δ 8.81 (d, J=4.9 Hz, 2H), 8.11-8.05 (m, 1H), 8.05-8.00 (m, 1H), 7.77 (dd, J=8.7, 2.3 Hz, 1H), 7.31-7.27 (m, 1H), 7.23 (t, J=4.8 Hz, 1H), 6.91 (d, J=8.7 Hz, 1H), 6.72-6.64 (m, 1H), 4.97 (dt, J=10.1, 3.4 Hz, 1H), 4.14-4.09 (m, 1H), 3.68 (dt, J=10.9, 3.2 Hz, 1H), 3.46 (dd, J=10.9, 1.5 Hz, 1H), 2.65 (s, 1H), 2.28-2.18 (m, 1H), 1.48-1.38 (m, 2H), 1.25-1.18 (m, 1H).

Example 39

(2-methoxy-6-(1H-pyrazol-5-yl)phenyl)((1S,4R,6R)-6-((5-(trifluoromethyl)pyridin-2-yl)oxy)-2-azabicyclo[2.2.1]heptan-2-yl)methanone

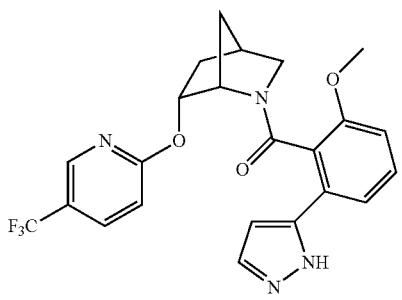 [SMILES: COc1cccc(-c2ccn[nH]2)c1C(=O)N1CC2CC(Oc3ccc(C(F)(F)F)cn3)C1C2]

Prepared analogous to Example 25 substituting intermediate A-20 with intermediate A-30. MS (ESI) mass calcd. $C_{23}H_{21}F_3N_4O_3$, 458.2. m/z found 459.3 [M+H]$^+$. $^1$H NMR (400 MHz, Chloroform-d, Compound present as a mixture of rotamers, major rotamer reported) δ 8.00 (s, 1H), 7.75 (dd, J=8.7, 2.6 Hz, 1H), 7.62-7.57 (m, 1H), 7.34-7.26 (m, 1H), 7.25-7.21 (m, 1H), 6.76 (d, J=8.7 Hz, 1H), 6.53 (d, J=2.0 Hz, 1H), 6.46 (d, J=8.4 Hz, 1H), 4.84 (dt, J=10.2, 3.4 Hz, 1H), 4.15 (s, 1H), 3.54-3.46 (m, 4H), 3.34 (d, J=10.8 Hz, 1H), 2.49 (s, 1H), 2.19-2.07 (m, 1H), 1.55-1.22 (m, 3H).

Example 40

(2-methoxy-6-(pyrimidin-2-yl)phenyl)((1S,4R,6R)-6-((5-(trifluoromethyl)pyridin-2-yl)oxy)-2-azabicyclo[2.2.1]heptan-2-yl)methanone

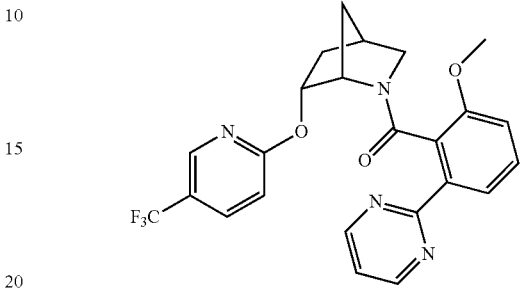

Prepared analogous to Example 25 substituting intermediate A-20 with intermediate A-24. MS (ESI) mass calcd. $C_{24}H_{21}F_3N_4O_3$, 470.2. m/z found 471.1 [M+H]$^+$. Analytical HPLC using a XBridge C18 column (5 um, 100×4.6 mm), mobile phase of 10-100% ACN in 20 mM NH$_4$OH over 2 min and then hold at 100% ACN for 2 min, at a flow rate of 2.5 mL/min (Temperature=45° C.). R$_t$=2.01 and 2.24 min (major rotamers) at 254 nm.

Example 41

(2-(1,4-dimethyl-1H-pyrazol-5-yl)phenyl)((1S,4R,6R)-6-((5-(trifluoromethyl)pyridin-2-yl)oxy)-2-azabicyclo[2.2.1]heptan-2-yl)methanone

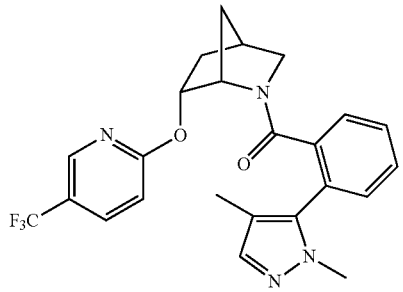

Prepared analogous to Example 25 substituting intermediate A-20 with intermediate A-31. MS (ESI) mass calcd. $C_{24}H_{23}F_3N_4O_2$, 456.2. m/z found 457.2 [M+H]$^+$. $^1$H NMR (500 MHz, Chloroform-d, Compound present as a mixture of rotamers (0.74:0.26), major rotamer reported) δ 7.95-7.90 (m, 1H), 7.75 (dd, J=9.0, 1.7 Hz, 1H), 7.39 (s, 1H), 7.30-7.27 (m, 1H), 7.13 (dd, J=7.7, 0.7 Hz, 1H), 7.03 (dd, J=7.7, 0.8 Hz, 1H), 6.91-6.87 (m, 1H), 6.80 (d, J=8.8 Hz, 1H), 4.96-4.91 (m, 1H), 4.05-4.03 (m, 1H), 3.61 (s, 3H), 3.39-3.35 (m, 1H), 3.34-3.29 (m, 1H), 2.54-2.49 (m, 1H), 2.19-2.10 (m, 1H), 2.08 (s, 3H), 1.44-1.34 (m, 2H), 0.95-0.89 (m, 1H).

Example 42

(1H-indol-7-yl)((1S,4R,6R)-6-((5-(trifluoromethyl)pyridin-2-yl)oxy)-2-azabicyclo[2.2.1]heptan-2-yl)methanone

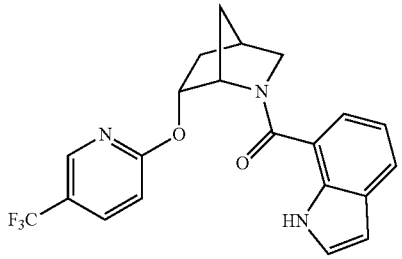 [SMILES: O=C(c1cccc2cc[nH]c12)N1CC2CC(Oc3ccc(C(F)(F)F)cn3)C1C2]

Prepared analogous to Example 25 substituting intermediate A-20 with intermediate A-29 and substituting purification by Agilent Prep Method X by silica gel chromatography (0-60% EtOAc (with 10% MeOH) in hexanes). MS (ESI) mass calcd. $C_{21}H_{18}F_3N_3O_2$, 401.1. m/z found 402.1 [M+H]$^+$. $^1$H NMR (400 MHz, DMSO-$d_6$) δ 10.82 (s, 1H), 7.92 (br. s, 1H), 7.62 (dd, J=8.9, 2.7 Hz, 1H), 7.32 (d, J=7.9 Hz, 1H), 7.21 (t, J=2.8 Hz, 1H), 6.93 (d, J=7.3 Hz, 1H), 6.69 (t, J=7.5 Hz, 1H), 6.57 (d, J=8.7 Hz, 1H), 6.32-6.25 (m, 1H), 5.06 (dt, J=10.0, 3.1 Hz, 1H), 4.67 (br. s, 1H), 3.60-3.53 (m, 1H), 3.52-3.44 (m, 1H), 2.70-2.62 (m, 1H), 2.29-2.17 (m, 1H), 2.06-1.99 (m, 1H), 1.73 (d, J=10.2 Hz, 1H), 1.30 (dt, J=13.4, 3.5 Hz, 1H).

Example 43

(5-fluoro-2-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone

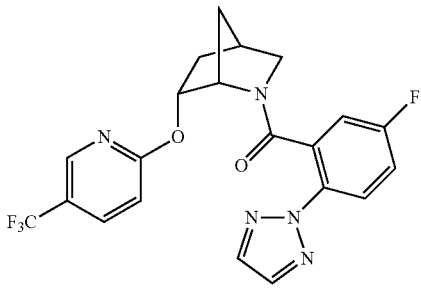 [SMILES: O=C(c1cc(F)ccc1-n1nccn1)N1CC2CC(Oc3ccc(C(F)(F)F)cn3)C1C2]

Prepared analogous to Example 25 substituting intermediate A-20 with intermediate A-10. MS (ESI) mass calcd. for $C_{21}H_{17}F_4N_5O_2$, 447.2. m/z found 448.2 [M+H]$^+$. $^1$H NMR (400 MHz, Chloroform-d, Compound present as a mixture of rotamers (0.91:0.09), major rotamer reported) δ 8.09-8.03 (m, 1H), 7.84-7.81 (m, 1H), 7.81-7.78 (m, 3H), 7.05-6.95 (m, 1H), 6.82 (d, J=8.7 Hz, 1H), 6.78 (dd, J=8.1, 2.9 Hz, 1H), 5.01 (dt, J=10.1, 3.3 Hz, 1H), 4.07-3.99 (m, 1H), 3.58 (dt, J=11.0, 3.2 Hz, 1H), 3.40 (dd, J=10.9, 1.5 Hz, 1H), 2.67-2.60 (m, 1H), 2.29-2.17 (m, 1H), 1.46-1.37 (m, 2H), 1.33-1.27 (m, 1H).

Example 44

(4-fluoro-2-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone

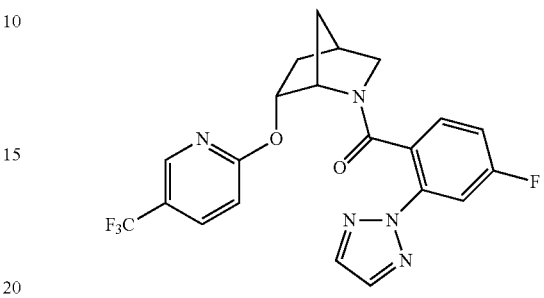

Prepared analogous to Example 25 substituting intermediate A-20 with intermediate A-12. MS (ESI) mass calcd. for $C_{21}H_{17}F_4N_5O_2$, 447.2. m/z found 448.2 [M+H]$^+$. $^1$H NMR (400 MHz, Chloroform-d, Compound present as a mixture of rotamers (0.88:0.12), major rotamer reported) δ 8.13-8.07 (m, 1H), 7.83 (s, 2H), 7.81-7.78 (m, 1H), 7.63 (dd, J=9.5, 2.5 Hz, 1H), 7.02 (dd, J=8.5, 5.9 Hz, 1H), 6.82 (d, J=8.7 Hz, 1H), 6.52 (td, J=8.1, 2.5 Hz, 1H), 5.01 (dt, J=10.2, 3.3 Hz, 1H), 4.03 (s, 1H), 3.63 (dt, J=11.0, 3.2 Hz, 1H), 3.40 (dd, J=10.9, 1.4 Hz, 1H), 2.68-2.61 (m, 1H), 2.28-2.16 (m, 1H), 1.46-1.38 (m, 2H), 1.38-1.28 (m, 1H).

Example 45

(2-bromo-3-fluorophenyl)((1S,4R,6R)-6-((5-(trifluoromethyl)pyridin-2-yl)oxy)-2-azabicyclo[2.2.1]heptan-2-yl)methanone

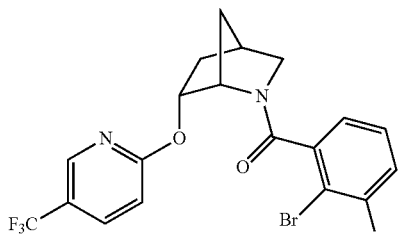

Prepared analogous to Example 25 substituting intermediate A-20 with intermediate A-32. MS (ESI) mass calcd. for $C_{19}H_{15}BrF_4N_2O_2$, 458.0. m/z found 461.1 [M+H]$^+$. $^1$H NMR (400 MHz, Chloroform-d, Compound present as a mixture of rotamers (0.82:0.18), major rotamer reported) δ 8.03 (s, 1H), 7.78 (dd, J=8.7, 2.5 Hz, 1H), 6.94 (td, J=8.3, 1.5 Hz, 1H), 6.87-6.81 (m, 1H), 6.73 (br. s, 1H), 6.63 (br. s, 1H), 5.15-5.06 (m, 1H), 4.23 (br. s, 1H), 3.73 (dt, J=11.1, 3.3 Hz, 1H), 3.45 (dd, J=11.0, 1.6 Hz, 1H), 2.80-2.71 (m, 1H), 2.37-2.25 (m, 1H), 1.99-1.89 (m, 1H), 1.84-1.71 (m, 1H), 1.46 (dt, J=13.6, 3.6 Hz, 1H).

Example 46

(2-fluoro-6-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone

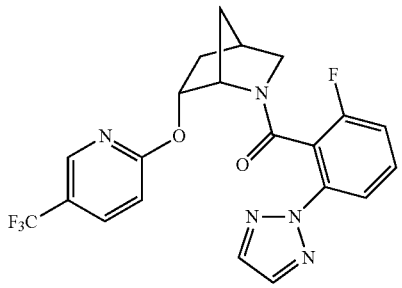 [SMILES: O=C(c1c(F)cccc1-n1nccn1)N1CC2CC(Oc3ccc(C(F)(F)F)cn3)C1C2]

Prepared analogous to Example 25 substituting intermediate A-20 with intermediate A-11. MS (ESI) mass calcd. for $C_{21}H_{17}F_4N_5O_2$, 447.2. m/z found 448.2 [M+H]$^+$. $^1$H NMR (400 MHz, Chloroform-d, Compound present as a mixture of rotamers (0.81:0.19), major rotamer reported) δ 8.05-8.00 (m, 1H), 7.83 (s, 2H), 7.80-7.77 (m, 1H), 7.77-7.72 (m, 1H), 7.32-7.27 (m, 1H), 6.89 (d, J=8.8 Hz, 1H), 6.60 (td, J=8.4, 1.0 Hz, 1H), 4.96 (dt, J=10.1, 3.4 Hz, 1H), 4.06-3.96 (m, 1H), 3.64 (dt, J=10.9, 3.2 Hz, 1H), 3.44 (dd, J=10.9, 1.5 Hz, 1H), 2.69-2.60 (m, 1H), 2.28-2.16 (m, 1H), 1.51-1.34 (m, 2H), 1.30-1.22 (m, 1H).

Example 47

((1S,4R,6R)-6-((5-bromopyridin-2-yl)oxy)-2-azabicyclo[2.2.1]heptan-2-yl)(2-fluoro-6-(pyrimidin-2-yl)phenyl)methanone

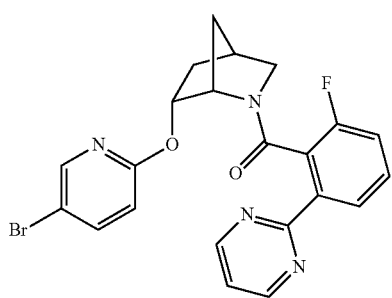 [SMILES: O=C(c1c(F)cccc1-c1ncccn1)N1CC2CC(Oc3ccc(Br)cn3)C1C2]

Step A: (1S,4R,6R)-tert-butyl 6-((5-bromopyridin-2-yl)oxy)-2-azabicyclo[2.2.1]heptane-2-carboxylate. To intermediate B-5 (101 mg, 0.474 mmol) dissolved in DMF (3 mL) was added NaH (38 mg, 0.95 mmol, 60% dispersion in mineral oil). After 5 minutes the sides of the flask were rinsed with additional DMF (1.0 mL) and 5-bromo-2-fluoropyridine (0.078 mL, 0.76 mmol) was then added and the mixture heated to 70° C. After heating at 70° C. for 3.25 h, the mixture was cooled to room temperature, quenched with saturated NH$_4$Cl solution, diluted with H$_2$O, and the aqueous layer extracted with EtOAc (3×). The combined organics were washed with H$_2$O, brine, dried with MgSO$_4$, filtered and concentrated. Purification via silica gel chromatography (0-25% EtOAc in hexanes) gave the title compound (149 mg, 0.40 mmol, 85%). MS (ESI) mass calcd. for $C_{16}H_{21}BrN_2O_3$, 368.1. m/z found 369.1 [M+H]$^+$. $^1$H NMR (400 MHz, Chloroform-d, compound is present a mixture of rotamers (0.75:0.25)) δ 8.20-8.11 (m, 1H), 7.63 (dd, J=8.8, 2.6 Hz, 0.75H), 7.58 (dd, J=8.8, 2.6 Hz, 0.25H), 6.63 (dd, J=8.8, 0.7 Hz, 0.75H), 6.57-6.52 (m, 0.25H), 5.29 (dt, J=9.8, 3.0 Hz, 0.25H), 5.22 (dt, J=10.1, 3.2 Hz, 0.75H), 4.57-4.49 (m, 1H), 3.43-3.31 (m, 1H), 3.19 (dd, J=9.5, 1.3 Hz, 0.75H), 3.15-3.09 (m, 0.25H), 2.59-2.50 (m, 1H), 2.26-2.13 (m, 1H), 1.77-1.66 (m, 1H), 1.65-1.56 (m, 1H), 1.43 (s, 2H), 1.41-1.23 (m, 1H), 1.16 (s, 7H).

Step B: (1S,4R,6R)-6-((5-bromopyridin-2-yl)oxy)-2-azabicyclo[2.2.1]heptane.xHCl. To the title compound of step A (149 mg, 0.0404 mmol) in EtOAc (1.5 mL) was added 4M HCl in dioxane (5 mL). After 3.25 h, the reaction was concentrated to give the title compound of step B (128 mg) which was used without further purification. MS (ESI) mass calcd. for $C_{11}H_{13}BrN_2O$, 268.0. m/z found 269.0 [M+H]$^+$.

Step C: ((1S,4R,6R)-6-((5-bromopyridin-2-yl)oxy)-2-azabicyclo[2.2.1]heptan-2-yl)(2-fluoro-6-(pyrimidin-2-yl)phenyl)methanone. To the title compound of step B (30 mg) and intermediate A-6 (24 mg, 0.11 mmol) in DMF (1.5 mL) was added DIPEA (0.25 mL, 1.45 mmol) and HATU (41 mg, 0.11 mmol). Upon completion the reaction was diluted with H$_2$O and the aqueous layer extracted with EtOAc (3×). The combined organics were washed with H$_2$O, brine, dried with MgSO$_4$, filtered, and concentrated. Purification of the concentrate was performed using Agilent Prep Method X to give the title compound (20 mg). MS (ESI) mass calcd. $C_{22}H_{18}BrFN_4O_2$, 468.1. m/z found 469.1 [M+H]$^+$. $^1$H NMR (400 MHz, Chloroform-d, Compound present as a mixture of rotamers (0.79:0.21), major rotamer reported) δ 8.80 (d, J=4.8 Hz, 2H), 8.08 (d, J=8.0 Hz, 1H), 7.77 (d, J=2.5 Hz, 1H), 7.64 (dd, J=8.8, 2.5 Hz, 1H), 7.39-7.30 (m, 1H), 7.23 (t, J=4.9 Hz, 1H), 6.81-6.72 (m, 2H), 4.86 (dt, J=10.1, 3.3 Hz, 1H), 4.11-4.02 (m, 1H), 3.65 (dt, J=10.9, 3.1 Hz, 1H), 3.44 (dd, J=10.8, 1.5 Hz, 1H), 2.66-2.59 (m, 1H), 2.25-2.15 (m, 1H), 1.42-1.34 (m, 2H), 1.22-1.13 (m, 1H).

Example 48

((1S,4R,6R)-6-((5-bromopyridin-2-yl)oxy)-2-azabicyclo[2.2.1]heptan-2-yl)(3-fluoro-2-(pyrimidin-2-yl)phenyl)methanone

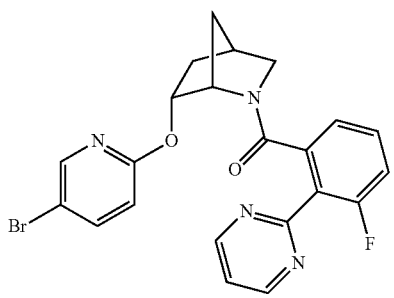 [SMILES: O=C(c1cccc(F)c1-c1ncccn1)N1CC2CC(Oc3ccc(Br)cn3)C1C2]

Prepared analogous to Example 47 substituting intermediate A-6 with intermediate A-2. MS (ESI) mass calcd. $C_{22}H_{18}BrFN_4O_2$, 468.1. m/z found 469.1 [M+H]$^+$. $^1$H NMR (400 MHz, Chloroform-d, Compound present as a mixture of rotamers (0.88:0.12), major rotamer reported) $^1$H NMR (400 MHz, Chloroform-d) δ 8.85 (d, J=4.9 Hz, 2H), 7.90-7.83 (m, 1H), 7.66 (dd, J=8.8, 2.5 Hz, 1H), 7.29-7.26 (m, 1H), 7.16-7.07 (m, 1H), 7.05-6.96 (m, 1H), 6.91 (dd, J=7.5, 1.3 Hz, 1H), 6.67 (d, J=8.7 Hz, 1H), 4.96 (dt, J=10.1, 3.3 Hz, 1H), 4.27-4.16 (m, 1H), 3.34-3.24 (m, 2H), 2.52 (s, 1H), 2.23-2.11 (m, 1H), 1.40 (d, J=10.8 Hz, 1H), 1.31 (dt, J=13.5, 3.6 Hz, 1H), 0.98-0.87 (m, 1H).

Example 49

(2-(2H-1,2,3-triazol-2-yl)phenyl)((1S,4R,6R)-6-((5-bromopyridin-2-yl)oxy)-2-azabicyclo[2.2.1]heptan-2-yl)methanone

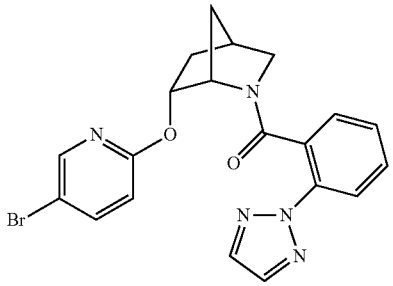 [SMILES: O=C(c1ccccc1-n1nccn1)N1CC2CC(Oc3ccc(Br)cn3)C1C2]

Prepared analogous to Example 47 substituting intermediate A-6 with intermediate A-1. MS (ESI) mass calcd. C₂₀H₁₈BrN₅O₂, 439.1. m/z found 440.1 [M+H]⁺. ¹H NMR (400 MHz, Chloroform-d, Compound present as a mixture of rotamers (0.89:0.11), major rotamer reported) δ 7.85 (dd, J=8.2, 1.1 Hz, 1H), 7.81 (s, 2H), 7.75 (dd, J=2.5, 0.7 Hz, 1H), 7.64 (dd, J=8.7, 2.6 Hz, 1H), 7.41-7.35 (m, 1H), 7.05 (dd, J=7.7, 1.5 Hz, 1H), 6.91 (td, J=7.6, 1.2 Hz, 1H), 6.65 (d, J=8.7 Hz, 1H), 4.89 (dt, J=10.2, 3.3 Hz, 1H), 4.05-3.97 (m, 1H), 3.59 (dt, J=10.9, 3.2 Hz, 1H), 3.38 (dd, J=10.9, 1.4 Hz, 1H), 2.63-2.56 (m, 1H), 2.23-2.12 (m, 1H), 1.41-1.33 (m, 2H), 1.29-1.23 (m, 1H).

Example 50

((1S,4R,6R)-6-((5-bromopyridin-2-yl)oxy)-2-azabicyclo[2.2.1]heptan-2-yl)(6-methyl-3-(2H-1,2,3-triazol-2-yl)pyridin-2-yl)methanone

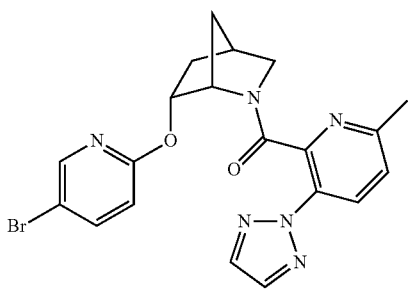 [SMILES: Cc1ccc(-n2nccn2)c(C(=O)N2CC3CC(Oc4ccc(Br)cn4)C2C3)n1]

Prepared analogous to Example 47 substituting intermediate A-6 with intermediate A-20. MS (ESI) mass calcd. C₂₀H₁₉BrN₆O₂, 454.1. m/z found 455.1 [M+H]⁺. ¹H NMR (400 MHz, Chloroform-d, Compound present as a mixture of rotamers (0.85:0.15), major rotamer reported) δ 8.03 (d, J=8.4 Hz, 1H), 7.82 (s, 2H), 7.70 (dd, J=2.6, 0.7 Hz, 1H), 7.56 (dd, J=8.8, 2.6 Hz, 1H), 7.14 (d, J=8.4 Hz, 1H), 6.66 (dd, J=8.6, 0.7 Hz, 1H), 4.82 (dt, J=10.2, 3.3 Hz, 1H), 4.23-4.16 (m, 1H), 3.65 (dt, J=11.0, 3.2 Hz, 1H), 3.43 (dd, J=10.9, 1.5 Hz, 1H), 2.63-2.58 (m, 1H), 2.30 (s, 3H), 2.23-2.11 (m, 1H), 1.48-1.33 (m, 3H).

Example 51

55415685# (2-(2H-1,2,3-triazol-2-yl)phenyl)((1S,4R,6R)-6-((3-(trifluoromethyl)pyridin-2-yl)oxy)-2-azabicyclo[2.2.1]heptan-2-yl)methanone

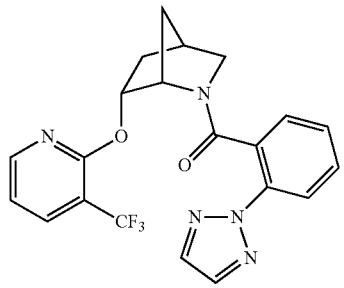 [SMILES: O=C(c1ccccc1-n1nccn1)N1CC2CC(Oc3ncccc3C(F)(F)F)C1C2]

Step A: (1S,4R,6R)-tert-butyl 6-((3-(trifluoromethyl)pyridin-2-yl)oxy)-2-azabicyclo[2.2.1]heptane-2-carboxylate. To intermediate B-5 (101 mg, 0.474 mmol) dissolved in DMF (3 mL) was added NaH (38 mg, 0.95 mmol, 60% dispersion in mineral oil). After 5 minutes the sides of the flask were rinsed with additional DMF (1.0 mL) and 2-fluoro-3-(trifluoromethyl)pyridine (0.091 mL, 0.76 mmol) was then added and the mixture heated to 70° C. After heating at 70° C. for 3 h, the mixture was cooled to room temperature, quenched with saturated NH₄Cl solution, diluted with EtOAc and H₂O. The aqueous layer was extracted with EtOAc (3×). The combined organics were washed with H₂O, 5% aqueous LiCl, brine, dried with Na₂SO₄, filtered, and concentrated. Purification via silica gel chromatography (0-35% EtOAc in hexanes) gave the title compound (87 mg, 0.24 mmol, 51%) as a white solid. MS (ESI) mass calcd. for C₁₇H₂₁F₃N₂O₃, 358.2. m/z found 303.1 [M+2H-tBu]⁺. ¹H NMR (400 MHz, Chloroform-d, Compound present as a mixture of rotamers, (0.68:0.32), major rotamer reported) δ 8.35-8.25 (m, 1H), 7.90-7.82 (m, 1H), 6.96 (dd, J=7.5, 5.0 Hz, 1H), 5.32 (dt, J=10.1, 3.1 Hz, 1H), 4.64-4.58 (m, 1H), 3.42 (dt, J=9.5, 3.1 Hz, 1H), 3.15 (d, J=9.5 Hz, 1H), 2.61-2.56 (m, 1H), 2.27-2.15 (m, 1H), 1.76-1.66 (m, 1H), 1.63 (br. s, 1H), 1.48 (dt, J=13.5, 3.5 Hz, 1H), 1.08 (s, 9H).

Step B: (1S,4R,6R)-6-((3-(trifluoromethyl)pyridin-2-yl)oxy)-2-azabicyclo[2.2.1]heptane.xHCl. To the title compound of step A (86 mg, 0.24 mmol) in EtOAc (1 mL) was added 4M HCl in dioxane (3 mL). After 2 h, the reaction was concentrated to give the title compound of step B (76.5 mg) as a white solid and used without further purification. MS (ESI) mass calcd. for C₁₂H₁₃F₃N₂O, 258.1. m/z found 259.1 [M+H]⁺.

Step C: (2-(2H-1,2,3-triazol-2-yl)phenyl)((1S,4R,6R)-6-((3-(trifluoromethyl)pyridin-2-yl)oxy)-2-azabicyclo[2.2.1]heptan-2-yl)methanone. To the title compound of step B (25 mg) and intermediate A-1 (18 mg, 0.093 mmol) in DMF (0.8 mL) was added DIPEA (75 μL, 0.44 mmol) and HATU (36 mg, 0.093 mmol), and the reaction mixture was stirred at room temperature for 1 h. The reaction was quenched by the addition of H₂O and the aqueous layer was extracted with EtOAc (3×). The combined organics were washed with H₂O, 5% aqueous LiCl, brine, dried with Na₂SO₄, filtered, and concentrated. Purification via silica gel chromatography (0-60% EtOAc in hexanes) gave the title compound (29 mg). MS (ESI) mass calcd. $C_{21}H_{18}F_3N_5O_2$, 429.1. m/z found 430.1 [M+H]$^+$. $^1$H NMR (400 MHz, Chloroform-d, Compound present as a mixture of rotamers, (0.76:0.24), major rotamer reported) δ 7.93-7.82 (m, 4H), 7.81 (s, 2H), 7.07 (dd, J=7.7, 1.5 Hz, 1H), 6.93-6.86 (m, 1H), 6.75 (td, J=7.6, 1.2 Hz, 1H), 5.04 (dt, J=10.2, 3.4 Hz, 1H), 4.15-4.04 (m, 1H), 3.66 (dt, J=10.9, 3.3 Hz, 1H), 3.38 (dd, J=10.9, 1.4 Hz, 1H), 2.66-2.60 (m, 1H), 2.27-2.15 (m, 1H), 1.48 (dt, J=13.3, 3.6 Hz, 1H), 1.44-1.37 (m, 1H), 1.36-1.28 (m, 1H).

Example 52

(6-methyl-3-(2H-1,2,3-triazol-2-yl)pyridin-2-yl)((1S, 4R,6R)-6-((3-(trifluoromethyl)pyridin-2-yl)oxy)-2-azabicyclo[2.2.1]heptan-2-yl)methanone

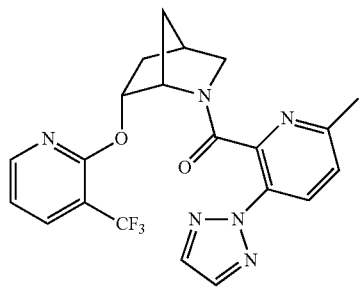 [SMILES: Cc1ccc(-n2nccn2)c(C(=O)N2CC3CC(Oc4ncccc4C(F)(F)F)C2C3)n1]

Prepared analogous to Example 51 substituting intermediate A-1 with intermediate A-20. MS (ESI) mass calcd. $C_{21}H_{19}F_3N_6O_2$, 444.2. m/z found 445.0 [M+H]$^+$. $^1$H NMR (400 MHz, Chloroform-d, Compound present as a mixture of rotamers, (0.72:0.28), major rotamer reported) δ 8.01 (d, J=8.5 Hz, 1H), 7.83-7.78 (m, 4H), 7.05 (d, J=8.4 Hz, 1H), 6.85-6.78 (m, 1H), 4.97 (dt, J=10.4, 3.3 Hz, 1H), 4.31 (br. s, 1H), 3.70 (dt, J=10.9, 3.3 Hz, 1H), 3.42 (d, J=10.9 Hz, 1H), 2.66-2.62 (m, 1H), 2.23-2.14 (m, 1H), 2.10 (s, 3H), 1.58-1.15 (m, 3H).

Example 53

(2-(2H-1,2,3-triazol-2-yl)phenyl)((1S,4S,6R)-6-((5-(trifluoromethyl)pyridin-2-yl)amino)-2-azabicyclo[2.2.1]heptan-2-yl)methanone

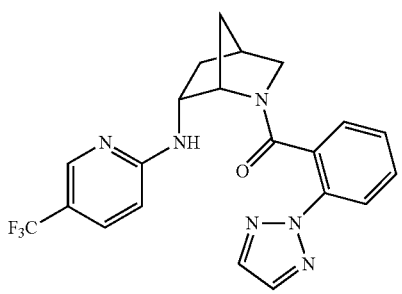 [SMILES: O=C(c1ccccc1-n1nccn1)N1CC2CC(Nc3ccc(C(F)(F)F)cn3)C1C2]

Step A: (1S,4S,6R)-tert-butyl 6-((5-(trifluoromethyl)pyridin-2-yl)amino)-2-azabicyclo[2.2.1]heptane-2-carboxylate. To a microwave vial containing degassed toluene (9 mL) was added Pd(OAc)$_2$ (24 mg, 0.035 mmol) and racemic BINAP (22 mg, 0.035 mmol) at room temperature and the reaction mixture was purged with N$_2$ for 5 min. Then, 2-chloro-5-(trifluoromethyl)pyridine (159 mg, 0.874 mmol), intermediate B-11 (204 mg), and sodium tert-butoxide (121 mg, 1.22 mmol) were added and the reaction mixture heated to 70° C. overnight. Upon completion of the reaction, the mixture was cooled to room temperature, filtered through Celite and washed with EtOAc. The filtrate was concentrated in vacuo and the crude residue subjected directly to silica gel chromatography (0-50% EtOAc in hexanes) to give the title compound of step A (198 mg, 0.554 mmol, 63%). MS (ESI) mass calcd. for $C_{17}H_{22}F_3N_3O_2$, 357.2. m/z found 358.2 [M+H]$^+$. $^1$H NMR (400 MHz, Chloroform-d, Compound present as a mixture of rotamers, major rotamer reported) δ 8.33 (s, 1H), 7.55 (d, J=8.8 Hz, 1H), 6.37 (d, J=8.8 Hz, 1H), 5.11-4.97 (m, 1H), 4.41 (s, 1H), 4.27-4.18 (m, 1H), 3.44-3.36 (m, 1H), 3.08 (d, J=9.7 Hz, 1H), 2.62-2.55 (m, 1H), 2.39-2.26 (m, 1H), 1.68-1.61 (m, 1H), 1.45-1.43 (m, 1H), 1.48 and 1.22 (two s, 9H).

Step B: Step B: (1S,4R,6R)—N-(5-(trifluoromethyl)pyridin-2-yl)-2-azabicyclo[2.2.1]heptan-6-amine.xHCl. To the title compound of step A (198 mg, 0.554 mmol) in EtOAc (3 mL) was added 4M HCl in dioxane (14 mL). After 1 h, the reaction was concentrated to give the title compound of step B (183 mg), which was used without further purification. MS (ESI) mass calcd. for $C_{12}H_{14}F_3N_3$, 257.1. m/z found 258.1 [M+H]$^+$.

Step C: (2-(2H-1,2,3-triazol-2-yl)phenyl)((1S,4S,6R)-6-((5-(trifluoromethyl)pyridin-2-yl)amino)-2-azabicyclo[2.2.1]heptan-2-yl)methanone. To the title compound of step B (30 mg) and intermediate A-1 (19 mg, 0.10 mmol) in DMF (1 mL) was added DIPEA (94 µL, 0.55 mmol) and HATU (38 mg, 0.10 mmol), and the reaction mixture was stirred at room temperature for 1 h. The reaction was quenched by the addition of H$_2$O and the aqueous layer was extracted with 4:1 EtOAc/hexanes (3×). The combined organics were washed with H$_2$O, 5% aqueous LiCl, brine, dried with Na$_2$SO$_4$, filtered, and concentrated. Purification via silica gel chromatography (25-100% EtOAc (with 10% MeOH) in hexanes) gave the title compound (20 mg). MS (ESI) mass calcd. $C_{21}H_{19}F_3N_6O$, 428.2. m/z found 429.1 [M+H]$^+$. $^1$H NMR (400 MHz, DMSO-d$_6$, Compound presents as a mixture of rotamers, major rotamer reported) δ 8.10 (s, 2H), 7.94-7.77 (m, 1H), 7.70 (d, J=8.1 Hz, 1H), 7.67-7.49 (m, 2H), 7.28 (td, J=7.7, 1.5 Hz, 1H), 6.96-6.82 (m, 1H), 6.77-6.56 (m, 2H), 3.96 (br. s, 1H), 3.64 (br. s, 1H), 3.33-3.25 (m, 1H), 3.23-3.14 (m, 1H), 2.15-2.00 (m, 1H), 1.44-1.33 (m, 1H), 1.23-1.03 (m, 2H), *1H buried under DMSO-d$_6$ peak.

Example 54

(6-methyl-3-(2H-1,2,3-triazol-2-yl)pyridin-2-yl)((1S, 4S,6R)-6-((5-(trifluoromethyl)pyridin-2-yl)amino)-2-azabicyclo[2.2.1]heptan-2-yl)methanone

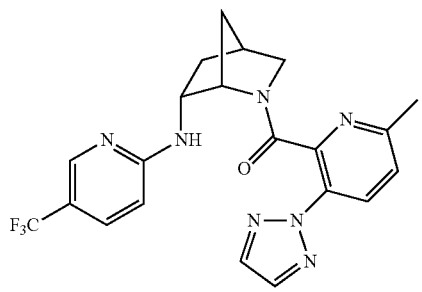

Prepared analogous to Example 53 substituting intermediate A-1 with intermediate A-20 and substituting purification by silica gel chromatography with Agilent Prep Method X. MS (ESI) mass calcd. $C_{21}H_{20}F_3N_7O$, 443.2. m/z found 444.2 [M+H]+. Analytical HPLC was obtained on a Agilent 1100 Series using a XBridge C18 column (5 um, 100×4.6 mm), mobile phase of 10-100% ACN in 20 mM $NH_4OH$ over 8 min and then hold at 100% ACN for 3 min, at a flow rate of 1 mL/min (Temperature=30° C.). $R_t$=5.92 min (major rotamer) at 254 nm.

Example 55

(3-methyl-2-(2H-1,2,3-triazol-2-yl)phenyl)((1S,4S, 6R)-6-((5-(trifluoromethyl)pyridin-2-yl)amino)-2-azabicyclo[2.2.1]heptan-2-yl)methanone

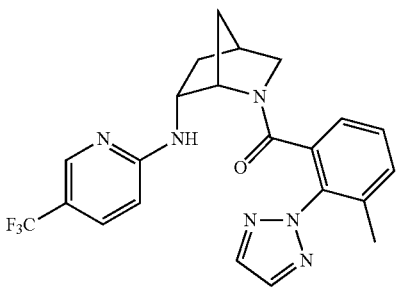

Prepared analogous to Example 53 substituting intermediate A-1 with intermediate A-22 and substituting purification by silica gel chromatography with Agilent Prep Method X. MS (ESI) mass calcd. $C_{22}H_{21}F_3N_6O$, 442.2. m/z found 443.2 [M+H]+. Analytical HPLC was obtained on a Agilent 1100 Series using a XBridge C18 column (5 um, 100×4.6 mm), mobile phase of 10-100% ACN in 20 mM $NH_4OH$ over 8 min and then hold at 100% ACN for 3 min, at a flow rate of 1 mL/min (Temperature=30° C.). $R_t$=6.85 min (major rotamer) at 254 nm.

Example 56

(7-ethoxyquinolin-8-yl)((1S,4S,6R)-6-((5-(trifluoromethyl)pyridin-2-yl)amino)-2-azabicyclo[2.2.1] heptan-2-yl)methanone

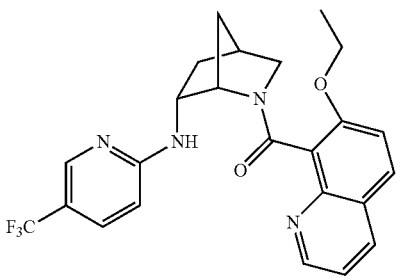 [SMILES: CCOc1ccc2cccnc2c1C(=O)N1CC2CC(Nc3ccc(C(F)(F)F)cn3)C1C2]

Prepared analogous to Example 53 substituting intermediate A-1 with intermediate A-25 and substituting purification by silica gel chromatography with Agilent Prep Method X. MS (ESI) mass calcd. $C_{24}H_{23}F_3N_4O_2$, 456.2. m/z found 457.2 [M+H]+. Analytical HPLC was obtained on a Agilent 1100 Series using a XBridge C18 column (5 um, 100×4.6 mm), mobile phase of 10-100% ACN in 20 mM $NH_4OH$ over 8 min and then hold at 100% ACN for 3 min, at a flow rate of 1 mL/min (Temperature=30° C.). $R_t$=6.45 min (major rotamer) at 254 nm.

Example 57

(5-fluoro-2-(2H-1,2,3-triazol-2-yl)phenyl)((1S,4S, 6R)-6-((5-(trifluoromethyl)pyridin-2-yl)amino)-2-azabicyclo[2.2.1]heptan-2-yl)methanone

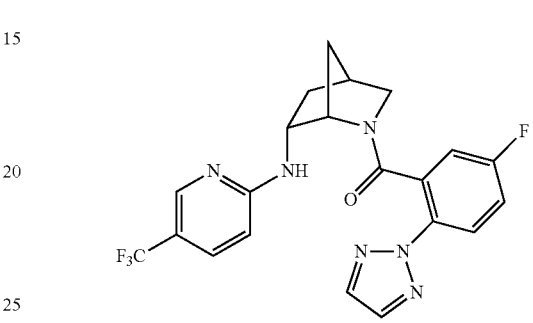

Prepared analogous to Example 53 substituting intermediate A-1 with intermediate A-10. MS (ESI) mass calcd. $C_{21}H_{18}F_4N_6O$, 446.1. m/z found 447.1 [M+H]+. 1H NMR (400 MHz, Methanol-$d_4$) δ 7.95 (s, 2H), 7.91-7.84 (m, 1H), 7.81 (dd, J=9.0, 4.7 Hz, 1H), 7.56 (d, J=8.1 Hz, 1H), 7.12-7.02 (m, 1H), 6.78-6.67 (m, 1H), 6.67-6.47 (m, 1H), 4.02-3.91 (m, 1H), 3.85 (br. s, 1H), 3.42 (dt, J=11.1, 3.2 Hz, 1H), 3.30-3.27 (m, 1H), 2.63-2.55 (m, 1H), 2.26-2.14 (m, 1H), 1.51-1.40 (m, 1H), 1.28-1.16 (m, 2H).

Example 58

(5-fluoro-2-(pyrimidin-2-yl)phenyl)((1S,4S,6R)-6-((5-(trifluoromethyl)pyridin-2-yl)amino)-2-azabicyclo[2.2.1]heptan-2-yl)methanone

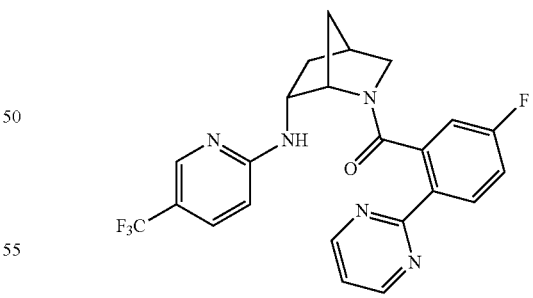

Prepared analogous to Example 53 substituting intermediate A-1 with intermediate A-7 and substituting purification by silica gel chromatography with Agilent Prep Method X. MS (ESI) mass calcd. $C_{23}H_{19}F_4N_5O$, 457.2. m/z found 458.1 [M+H]+. 1H NMR (400 MHz, DMSO-$d_6$, Compound presents as a mixture of rotamers (0.90:0.10), major rotamer reported) δ 8.87 (d, J=4.9 Hz, 2H), 8.03 (dd, J=8.8, 5.6 Hz, 1H), 7.88 (br. s, 1H), 7.64-7.49 (m, 2H), 7.45 (t, J=4.9 Hz, 1H), 7.04 (td, J=8.6, 2.8 Hz, 1H), 6.70-6.53 (m, 2H), 3.96

(br. s, 1H), 3.73 (br. s, 1H), 3.23-3.13 (m, 1H), 2.15-2.02 (m, 1H), 1.37 (d, J=9.7 Hz, 1H), 1.21-0.99 (m, 3H). *1H buried under DMSO-$d_6$ peak.

then hold at 100% ACN for 3 min, at a flow rate of 1 mL/min (Temperature=30° C.). $R_t$=6.27 min (major rotamer) at 254 nm.

Example 59

(2-(2H-1,2,3-triazol-2-yl)phenyl)((1S,4S,6R)-6-((5-(trifluoromethyl)pyrazin-2-yl)amino)-2-azabicyclo[2.2.1]heptan-2-yl)methanone Example 60

(2-(2H-1,2,3-triazol-2-yl)phenyl)((1S,4S,6R)-6-((5-(trifluoromethyl)pyrimidin-2-yl)amino)-2-azabicyclo[2.2.1]heptan-2-yl)methanone

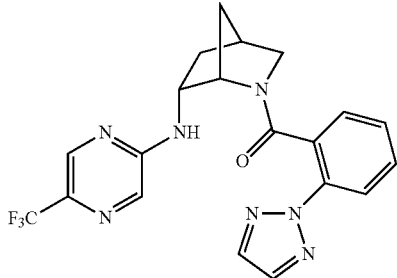

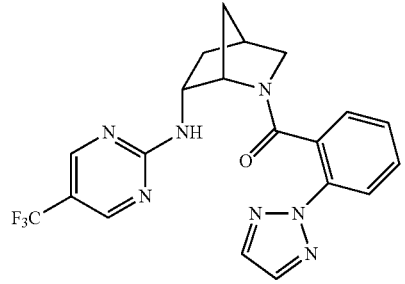

Step A: (1S,4S,6R)-tert-butyl 6-((5-(trifluoromethyl)pyrazin-2-yl)amino)-2-azabicyclo[2.2.1]heptane-2-carboxylate. To intermediate B-10 (44 mg) and 2-chloro-5-(trifluoromethyl)pyrazine (45 mg, 0.25 mmol) dissolved in DMF (2 mL) was added $K_2CO_3$ (43 mg, 0.31 mmol) and the mixture heated to 70° C. After heating at 70° C. for 3.5 h, the mixture was cooled to room temperature, diluted with $H_2O$, and the aqueous layer extracted with EtOAc (3×). The combined organics were washed with $H_2O$, brine, dried with $MgSO_4$, filtered and concentrated. Purification via silica gel chromatography (0-45% EtOAc in hexanes) gave the title compound (31 mg, 0.087 mmol, 42%). MS (ESI) mass calcd. for $C_{16}H_{21}F_2N_4O_2$, 358.2. m/z found 303.1 [M+2H-tBu]$^+$. $^1$H NMR (500 MHz, Chloroform-d) δ 8.38-8.25 (m, 1H), 7.93-7.76 (m, 1H), 6.25-6.12 and 5.57-5.44 (2m, 1H), 4.50-4.38 (m, 1H), 4.34-4.11 (m, 1H), 3.46-3.33 (m, 1H), 3.16-3.01 (m, 1H), 2.66-2.57 (m, 1H), 2.42-2.29 (m, 1H), 1.95-0.80 (m, 12H).

Step B: (1S,4R,6R)—N-(5-(trifluoromethyl)pyrazin-2-yl)-2-azabicyclo[2.2.1]heptan-6-amine.xHCl. To the title compound of step A (31 mg, 0.087 mmol) in EtOAc (0.5 mL) was added 4M HCl in dioxane (4 mL). After 1.5 h additional 4 M HCl in dioxane (2 mL) was added. After an additional 1.25 h, the reaction was concentrated to give the title compound of step B (31 mg) which was used without further purification. MS (ESI) mass calcd. for $C_{11}H_{13}F_3N_4$, 258.1. m/z found 259.1 [M+H]$^+$.

Step C: (2-(2H-1,2,3-triazol-2-yl)phenyl)((1S,4S,6R)-6-((5-(trifluoromethyl)pyrazin-2-yl)amino)-2-azabicyclo[2.2.1]heptan-2-yl)methanone. To the title compound of step B (29 mg) and intermediate A-1 (18 mg, 0.096 mmol) in DMF (2.0 mL) was added DIPEA (0.1 mL, 0.58 mmol) and HATU (37 mg, 0.096 mmol). Upon completion the reaction was diluted with $H_2O$ and the aqueous layer extracted with EtOAc (3×). The combined organics were washed with $H_2O$, brine, dried with $MgSO_4$, filtered, and concentrated. Purification of the concentrate was performed using Agilent Prep Method X to give the title compound (8 mg). MS (ESI) mass calcd. $C_{20}H_{18}F_3N_7O$, 429.2. m/z found 430.2 [M+H]$^+$. Analytical HPLC was obtained on a Agilent 1100 Series using a XBridge C18 column (5 um, 100×4.6 mm), mobile phase of 10-100% ACN in 20 mM $NH_4OH$ over 8 min and Example 61

(6-methyl-3-(2H-1,2,3-triazol-2-yl)pyridin-2-yl)((1S,4S,6R)-6-((5-(trifluoromethyl)pyrazin-2-yl)amino)-2-azabicyclo[2.2.1]heptan-2-yl)methanone

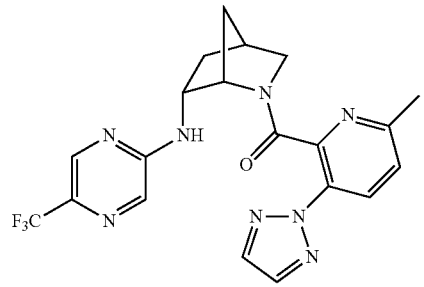

Example 62

(6-methyl-3-(2H-1,2,3-triazol-2-yl)pyridin-2-yl)((1S,4S,6R)-6-((5-(trifluoromethyl)pyrimidin-2-yl)amino)-2-azabicyclo[2.2.1]heptan-2-yl)methanone

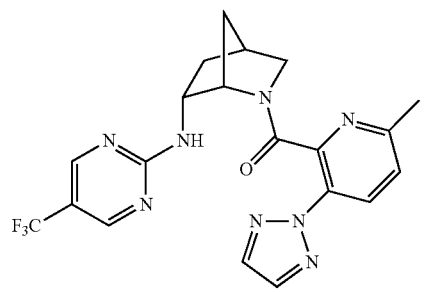

Example 63

(4-methyl-2-(2H-1,2,3-triazol-2-yl)phenyl)((1S,4S, 6R)-6-((5-(trifluoromethyl)pyridin-2-yl)amino)-2-azabicyclo[2.2.1]heptan-2-yl)methanone

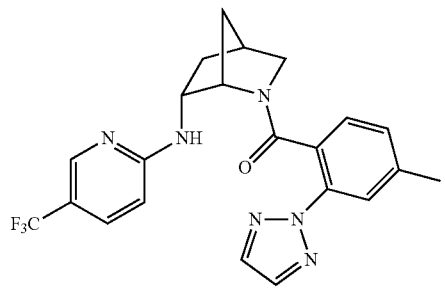 [SMILES: Cc1ccc(C(=O)N2CC3CC(Nc4ccc(C(F)(F)F)cn4)C2C3)c(-n2nccn2)c1]

Example 64

(4-methyl-2-(2H-1,2,3-triazol-2-yl)phenyl)((1S,4S, 6R)-6-((5-(trifluoromethyl)pyrazin-2-yl)amino)-2-azabicyclo[2.2.1]heptan-2-yl)methanone

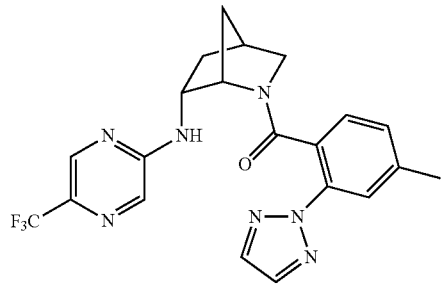 [SMILES: Cc1ccc(C(=O)N2CC3CC(Nc4cnc(C(F)(F)F)cn4)C2C3)c(-n2nccn2)c1]

Example 65

(4-methyl-2-(2H-1,2,3-triazol-2-yl)phenyl)((1S,4S, 6R)-6-((5-(trifluoromethyl)pyrimidin-2-yl)amino)-2-azabicyclo[2.2.1]heptan-2-yl)methanone

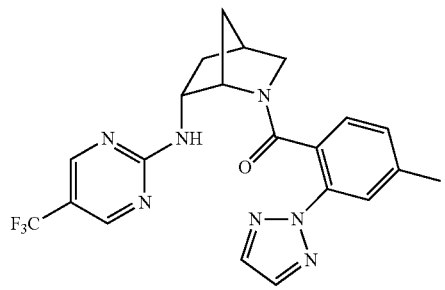 [SMILES: Cc1ccc(C(=O)N2CC3CC(Nc4ncc(C(F)(F)F)cn4)C2C3)c(-n2nccn2)c1]

Example 66

(3-fluoro-2-(pyrimidin-2-yl)phenyl)((1S,4S,6R)-6-((5-(trifluoromethyl)pyridin-2-yl)amino)-2-azabicyclo[2.2.1]heptan-2-yl)methanone

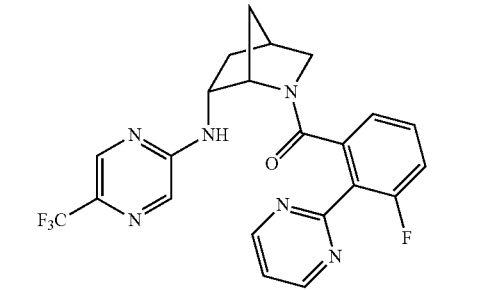

Example 67

(3-fluoro-2-(pyrimidin-2-yl)phenyl)((1S,4S,6R)-6-((5-(trifluoromethyl)pyrazin-2-yl)amino)-2-azabicyclo[2.2.1]heptan-2-yl)methanone Example 68

(3-fluoro-2-(pyrimidin-2-yl)phenyl)((1S,4S,6R)-6-((5-(trifluoromethyl)pyrimidin-2-yl)amino)-2-azabicyclo[2.2.1]heptan-2-yl)methanone

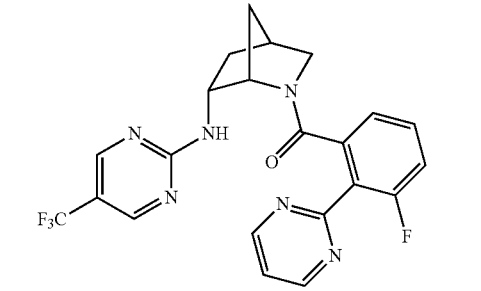

Example 69

(2-(3-methyl-1,2,4-oxadiazol-5-yl)phenyl)((1S,4S,6R)-6-((5-(trifluoromethyl)pyridin-2-yl)amino)-2-azabicyclo[2.2.1]heptan-2-yl)methanone

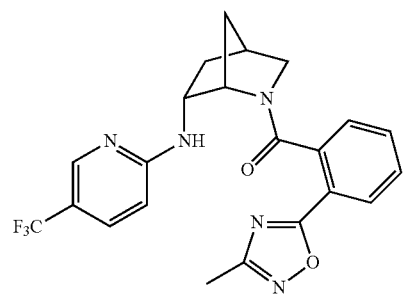 [SMILES: Cc1noc(-c2ccccc2C(=O)N2CC3CC(Nc4ccc(C(F)(F)F)cn4)C2C3)n1]

Example 70

(3-fluoro-2-(3-methyl-1,2,4-oxadiazol-5-yl)phenyl)((1S,4S,6R)-6-((5-(trifluoromethyl)pyridin-2-yl)amino)-2-azabicyclo[2.2.1]heptan-2-yl)methanone

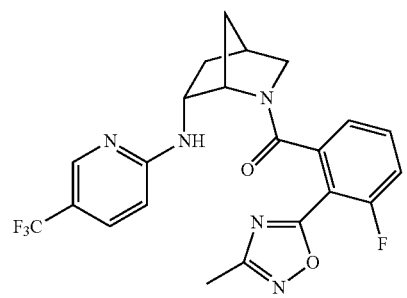

Example 71

(3-fluoro-2-(3-methyl-1,2,4-oxadiazol-5-yl)phenyl)((1S,4R,6R)-6-((5-(trifluoromethyl)pyridin-2-yl)oxy)-2-azabicyclo[2.2.1]heptan-2-yl)methanone

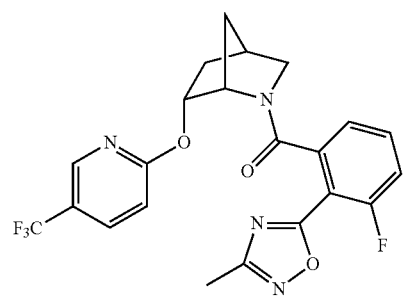 [SMILES: Cc1noc(-c2c(F)cccc2C(=O)N2CC3CC(Oc4ccc(C(F)(F)F)cn4)C2C3)n1]

Example 72

(3-fluoro-2-(3-methyl-1,2,4-oxadiazol-5-yl)phenyl)((1S,4R,6R)-6-((5-(trifluoromethyl)pyridin-2-yl)oxy)-2-azabicyclo[2.2.1]heptan-2-yl)methanone

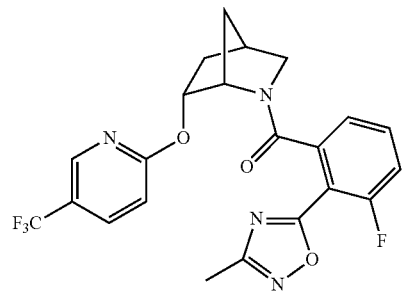 [SMILES: Cc1noc(-c2c(F)cccc2C(=O)N2CC3CC(Oc4ccc(C(F)(F)F)cn4)C2C3)n1]

Example 73

(3-fluoro-2-(pyrimidin-2-yl)phenyl)((1S,4R,6R)-6-((5-(trifluoromethyl)pyridin-2-yl)oxy)-2-azabicyclo[2.2.2]octan-2-yl)methanone

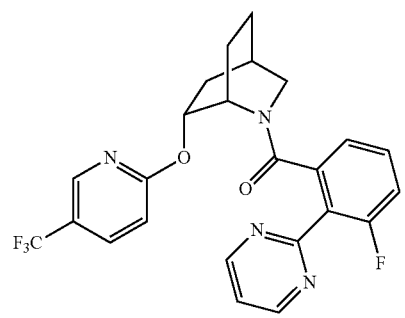 [SMILES: O=C(c1cccc(F)c1-c1ncccn1)N1CC2CCC1C(Oc1ccc(C(F)(F)F)cn1)C2]

Example 74

(3-fluoro-2-(pyrimidin-2-yl)phenyl)((1S,4R,6R)-6-((5-(trifluoromethyl)pyrazin-2-yl)oxy)-2-azabicyclo[2.2.2]octan-2-yl)methanone

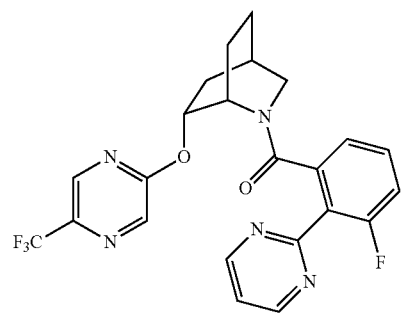 [SMILES: O=C(c1cccc(F)c1-c1ncccn1)N1CC2CCC1C(Oc1cnc(C(F)(F)F)cn1)C2]

Example 75

(3-fluoro-2-(pyrimidin-2-yl)phenyl)((1S,4R,6R)-6-((5-(trifluoromethyl)pyrimidin-2-yl)oxy)-2-azabicyclo[2.2.2]octan-2-yl)methanone

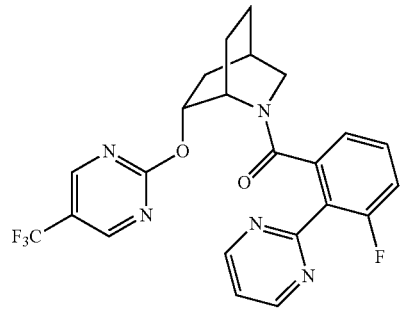 [SMILES: O=C(c1cccc(F)c1-c1ncccn1)N1CC2CCC1C(Oc1ncc(C(F)(F)F)cn1)C2]

Example 76

(6-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.2]octan-2-yl)methanone

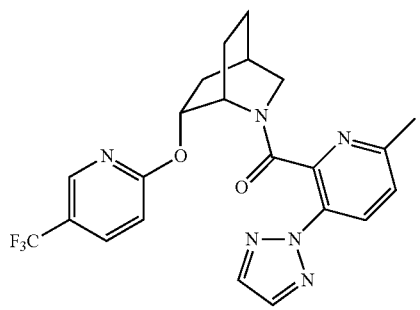 [SMILES: Cc1ccc(-n2nccn2)c(C(=O)N2CC3CCC2C(Oc2ccc(C(F)(F)F)cn2)C3)n1]

Example 77

(6-methyl-3-(2H-1,2,3-triazol-2-yl)pyridin-2-yl)((1S,4R,6R)-6-((5-(trifluoromethyl)pyrazin-2-yl)oxy)-2-azabicyclo[2.2.2]octan-2-yl)methanone

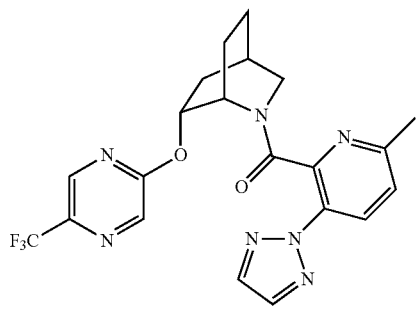 [SMILES: Cc1ccc(-n2nccn2)c(C(=O)N2CC3CCC2C(Oc2cnc(C(F)(F)F)cn2)C3)n1]

Example 78

(6-methyl-3-(2H-1,2,3-triazol-2-yl)pyridin-2-yl)((1S,4R,6R)-6-((5-(trifluoromethyl)pyrimidin-2-yl)oxy)-2-azabicyclo[2.2.2]octan-2-yl)methanone

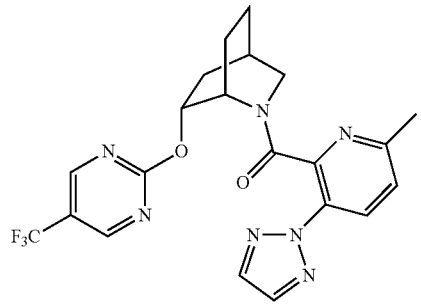 [SMILES: Cc1ccc(-n2nccn2)c(C(=O)N2CC3CCC2C(Oc2ncc(C(F)(F)F)cn2)C3)n1]

Example 79

(6-methyl-3-(2H-1,2,3-triazol-2-yl)pyridin-2-yl)((1S,4R,6R)-6-((5-(trifluoromethyl)pyrimidin-2-yl)amino)-2-azabicyclo[2.2.2]octan-2-yl)methanone

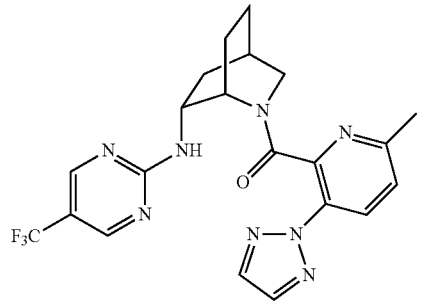 [SMILES: Cc1ccc(-n2nccn2)c(C(=O)N2CC3CCC2C(Nc2ncc(C(F)(F)F)cn2)C3)n1]

Example 80

(3-fluoro-2-(pyrimidin-2-yl)phenyl)((1S,4R,6R)-6-((5-(trifluoromethyl)pyrazin-2-yl)amino)-2-azabicyclo[2.2.2]octan-2-yl)methanone

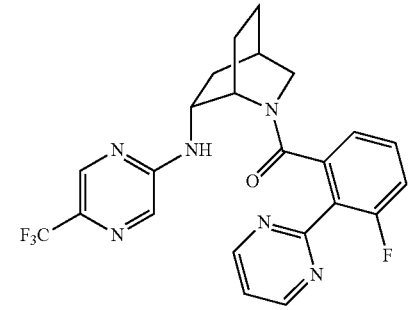 [SMILES: O=C(c1cccc(F)c1-c1ncccn1)N1CC2CCC1C(Nc1cnc(C(F)(F)F)cn1)C2]

Example 81

(3-fluoro-2-(pyrimidin-2-yl)phenyl)((1S,4R,6R)-6-((5-(trifluoromethyl)pyrimidin-2-yl)amino)-2-azabicyclo[2.2.2]octan-2-yl)methanone

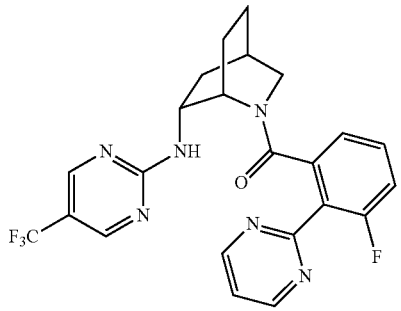 [SMILES: O=C(c1cccc(F)c1-c1ncccn1)N1CC2CCC1C(Nc1ncc(C(F)(F)F)cn1)C2]

Example 82

(6-methyl-3-(2H-1,2,3-triazol-2-yl)pyridin-2-yl)((1S,4R,6R)-6-((5-(trifluoromethyl)pyrimidin-2-yl)amino)-2-azabicyclo[2.2.2]octan-2-yl)methanone

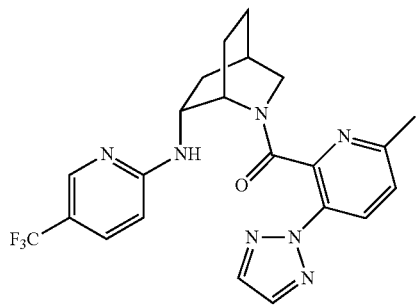 [SMILES: Cc1ccc(-n2nccn2)c(C(=O)N2CC3CCC2C(Nc2ccc(C(F)(F)F)cn2)C3)n1]

Example 83

(6-methyl-3-(2H-1,2,3-triazol-2-yl)pyridin-2-yl)((1S,4R,6R)-6-((5-(trifluoromethyl)pyrazin-2-yl)amino)-2-azabicyclo[2.2.2]octan-2-yl)methanone

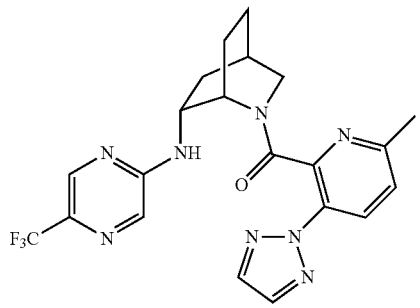 [SMILES: Cc1ccc(-n2nccn2)c(C(=O)N2CC3CCC2C(Nc2cnc(C(F)(F)F)cn2)C3)n1]

Example 84

(6-methyl-3-(2H-1,2,3-triazol-2-yl)pyridin-2-yl)((1S,4R,6R)-6-((5-(trifluoromethyl)pyrimidin-2-yl)amino)-2-azabicyclo[2.2.2]octan-2-yl)methanone

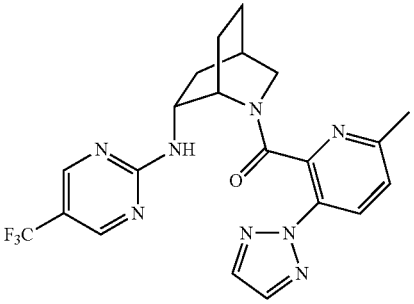 [SMILES: Cc1ccc(-n2nccn2)c(C(=O)N2CC3CCC2C(Nc2ncc(C(F)(F)F)cn2)C3)n1]

Assays:

The in vitro affinity of the compounds of the invention for the rat/human orexin 1 and human orexin 2 receptors was determined by competitive radioligand binding using (1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) (Langmead et al., 2004) and [$^3$H]EMPA (n-ethyl-2 [96-methoxy-pyridin-3-yl)-(toluene-2-sulfonyl)-amino]-N-pyridin-3-ylmethyl acetamide), respectively (Langmead et al., 2004, British Journal of Pharmacology 141:340-346; Malherbe et al., 2004, British Journal of Pharmacology 156:1326-41).

The in vitro functional antagonism of the compounds on the human orexin 1 and orexin 2 receptors was determined using fluorometric imaging plate reader (FLIPR) based calcium assays.

Rat and Human Orexin 1 Receptor Radioligand Binding Studies

Human Embryonic Kidney 293 cells (HEK293) stably expressing rat orexin 1 receptor (Genebank accession number NM_001525) or Chinese ovary cells (CHO) stably expressing human orexin 1 receptor (Genebank accession number NM_001526) were grown to confluency in DMEM (Hyclone, cat # SH30022), 10% FBS, 1× Pen/Strep, 1× sodium pyruvate, 10 mM HEPES, 600 µg/mL G418 and DMEM/F12 (Gibco, Cat #11039), 10% FBS, 1× Pen/Strep, 600 µg/mL G418 media, respectively on 150 cm$^2$ tissue culture plates, washed with 5 mM EDTA in PBS (HyClone Dulbecco's Phoshpate Buffered Saline 1× with Calcium and Magnesium, Cat # SH30264.01, hereafter referred to simply as PBS) and scraped into 50 ml tubes. After centrifugation (2K×G, 5 min. at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec prior to addition to the reactions. Competition binding experiments in 96 well polypropylene plates were performed using [$^3$H]-(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) (Moraveck Corporation, specific activity=35.3 Ci/mmol), diluted to a 10 nM concentration in PBS (4 nM final). Compounds were solubilized in 100% DMSO (Acros Organics, Cat. #61042-1000) and tested over a range of 7 concentrations (from 0.1 nM to 10 µM). The final concentration of DMSO in the reactions is equal to or less than 0.1%. Total and nonspecific binding was determined in the absence and presence of 10 µM almorexant. The total volume of each reaction is 200 µL (20 µL of diluted compounds, 80 µL of [$^3$H]-(1-(5-(2-fluoro-phenyl)-2- methyl-thiazol-4-yl)-1-((S)-2-(5-phenyl-(1,3,4)oxadiazol-2-ylmethyl)-pyrrolidin-1-yl)-methanone) diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

$IC_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as $K_i=IC_{50}/(1+C/K_d)$, where C is concentration of radioligand and $K_d=4$ nM for rat orexin 1 receptor and 6 nM for human orexin 1 receptor.

Human Orexin 2 Receptor Radioligand Binding Studies

HEK293 stably expressing human orexin 2 receptor (Genebank accession number NM_001526) were grown to confluency in DMEM (Hyclone, cat # SH30022), 10% FBS, 1× Pen/Strep, 1× NaPyruvate, 10 mM HEPES, 600 ug/ml G418 media on 150 cm² tissue culture plates, washed with 5 mM EDTA in PBS (HyClone Dulbecco's Phosphate Buffered Saline 1× with Calcium and Magnesium, Cat # SH30264.01, hereafter referred to simply as PBS) and scraped into 50 ml tubes. After centrifugation (2K×G, 5 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec just prior to addition to the reactions. Competition binding experiments in 96 well polypropylene plates were performed using [³H]-EMPA (Moraveck Corporation, specific activity=29.6 Ci/mmol), diluted to a 5 nM concentration in PBS (2 nM final concentration). Compounds were solubilized in 100% DMSO (Acros Organics, Cat. #61042-1000) and tested over a range of 7 concentration (from 0.1 nM to 10 μM). The final concentration of DMSO in the reactions is equal to or less than 0.1%. Total and nonspecific binding was determined in the absence and presence of 10 μM almorexant. The total volume of each reaction is 200 μL (20 μL of diluted compounds, 80 μL of [³H]-EMPA diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

$IC_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as $K_i=IC_{50}/(1+C/K_d)$, where C is concentration of radioligand and $K_d=2$ nM.

Human Orexin 1 Receptor $Ca^{2+}$ Mobilization Assay

CHO cells stably transfected with the human orexin 1 receptor (Genebank accession number NM_001526) were grown to confluency in DMEM/F12, 10% FBS, 1× pen-strep, 400 μg/ml G418. Cells were seeded on to 384-well Packard viewplates at a density of 10,000 cells/well and incubated overnight at 37° C., 5% CO2. The cells were dye-loaded with BD Calcium Assay kit (BD, cat #640178) in HBSS (Gibco, cat#14025-092) with 2.5 mM probenecid and incubated at 37° C., 5% $CO_2$ for 45 min. Cells were pre-incubated with compounds (diluted in DMEM/F-12) for 15-30 minutes before agonist (orexin A, 10 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent $pK_B$ values using a modified Cheng-Prusoff correction. Apparent $pK_B=-\log IC_{50}/1+[\text{conc agonist}/EC_{50}]$. Data are expressed as mean±S.E.M.

Human Orexin 2 Receptor $Ca^{2+}$ Mobilization Assay

PFSK-1 cells endogenously expressing the human orexin 2 receptor were grown to confluency in RPMI1640 (Hyclone, cat#30027.02), 10% FBS, 1× pen-strep. Cells were seeded on to 384-well Packard viewplates at a density of 5,000 cells/well and incubated overnight at 37° C., 5% CO2. The cells were dye-loaded with BD Calcium Assay kit (BD, cat #640178) in HBSS (Gibco, cat#14025-092) with 2.5 mM probenecid and incubated at 37° C., 5% $CO_2$ for 45 min. Cells were pre-incubated with compounds (diluted in DMEM/F-12) for 15-30 minutes before agonist (orexin B, 100 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent $pK_B$ values using a modified Cheng-Prusoff correction. Apparent $pK_B=-\log IC_{50}/1+[\text{conc agonist}/EC_{50}]$. Data are expressed as mean±S.E.M.

Preferred compounds of the invention are set forth in the table below. Orexin receptor activity of certain compounds of the invention is also set forth in the below table.

| Ex. No. | Compound | rOX1 $K_i$ (nM) | hOX1 $K_i$ (nM) | hOX2 $K_i$ (nM) | Compound Name |
|---|---|---|---|---|---|
| 1 | 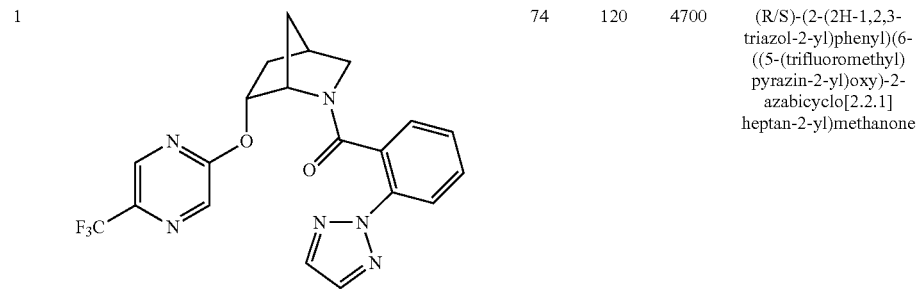 | 74 | 120 | 4700 | (R/S)-(2-(2H-1,2,3-triazol-2-yl)phenyl)(6-((5-(trifluoromethyl)pyrazin-2-yl)oxy)-2-azabicyclo[2.2.1]heptan-2-yl)methanone |

| Ex. No. | Compound | rOX1 K$_i$ (nM) | hOX1 K$_i$ (nM) | hOX2 K$_i$ (nM) | Compound Name |
|---|---|---|---|---|---|
| 2 | | 200 | 342 | 10000 | (R/S)-(6-methyl-3-(2H-1,2,3-triazol-2-yl)pyridin-2-yl)(6-((5-(trifluoromethyl)pyrazin-2-yl)oxy)-2-azabicyclo[2.2.1]heptan-2-yl)methanone |
| 3 | | 63 | 123 | 8900 | (R/S)-(3-ethoxyisoquinolin-4-yl)((5-(trifluoromethyl)pyrazin-2-yl)oxy)-2-azabicyclo[2.2.1]heptan-2-yl)methanone |
| 4 | | 837 | | >10000 | (R/S)-5-methyl-3-(2H-1,2,3-triazol-2-yl)pyridin-2-yl)(6-((5-(trifluoromethyl)pyrazin-2-yl)oxy)-2-azabicyclo[2.2.1]heptan-2-yl)methanone |
| 7 | | 21 | 12 | 800 | (R/S)-(2-(2H-1,2,3-triazol-2-yl)phenyl)(6-((5-(trifluoromethyl)pyridin-2-yl)oxy)-2-azabicyclo[2.2.1]heptan-2-yl)methanone |
| 8 | | 16 | 15 | 1450 | (R/S)-(3-ethoxyisoquinolin-4-yl)(6-((5-(trifluoromethyl)pyridin-2-yl)oxy)-2-azabicyclo[2.2.1]heptan-2-yl)methanone |

-continued

| Ex. No. | Compound | rOX1 $K_i$ (nM) | hOX1 $K_i$ (nM) | hOX2 $K_i$ (nM) | Compound Name |
|---|---|---|---|---|---|
| 9 | 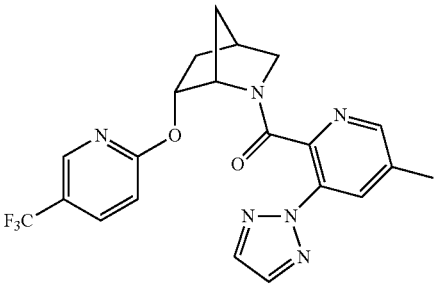 | 56 | 101 | 2554 | (R/S)-(5-methyl-3-(2H-1,2,3-triazol-2-yl)pyridin-2-yl)(6-((5-(trifluoromethyl)pyridin-2-yl)oxy)-2-azabicyclo[2.2.1]heptan-2-yl)methanone |
| 10 | 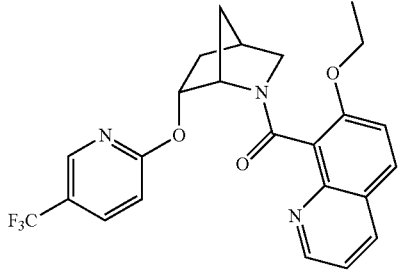 | 18 | 27 | 526 | (R/S)-(7-ethoxyquinolin-8-yl)(6-((5-(trifluoromethyl)pyridin-2-yl)oxy)-2-azabicyclo[2.2.1]heptan-2-yl)methanone |
| 11 | 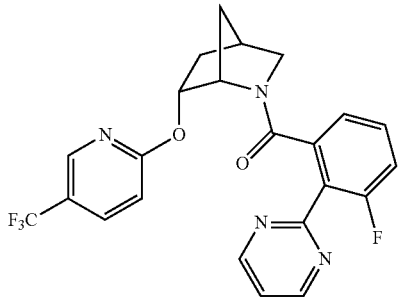 | 11 | 8 | 1475 | (R/S)-(3-fluoro-2-(pyrimidin-2-yl)phenyl)(6-((5-(trifluoromethyl)pyridin-2-yl)oxy)-2-azabicyclo[2.2.1]heptan-2-yl)methanone |
| 12 | 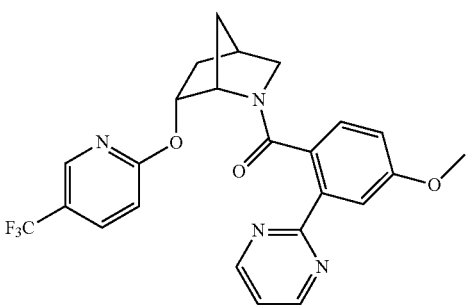 | 44 | 59 | >10000 | (R/S)-(4-methoxy-2-(pyrimidin-2-yl)phenyl)(6-((5-(trifluoromethyl)pyridin-2-yl)oxy)-2-azabicyclo[2.2.1]heptan-2-yl)methanone |
| 13 | 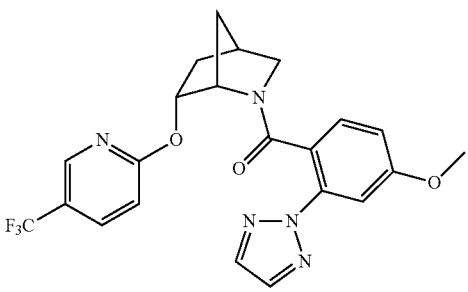 | 52 | 109 | >10000 | (R/S)-4-methoxy-2-(2H-1,2,3-triazol-2-yl)phenyl)(6-((5-(trifluoromethyl)pyridin-2-yl)oxy)-2-azabicyclo[2.2.1]heptan-2-yl)methanone |

| Ex. No. | Compound | rOX1 K$_i$ (nM) | hOX1 K$_i$ (nM) | hOX2 K$_i$ (nM) | Compound Name |
|---|---|---|---|---|---|
| 14 | | 16 | 21 | 855 | (R/S)-(5-fluoro-2-(2H-1,2,3-triazol-2-yl)phenyl)(6-((5-(trifluoromethyl)pyridin-2-yl)oxy)-2-azabicyclo[2.2.1]heptan-2-yl)methanone |
| 15 | | 17 | 40 | 229 | (R/S)-2-methoxy-6-(2H-1,2,3-triazol-2-yl)phenyl)(6-((5-(trifluoromethyl)pyridin-2-yl)oxy)-2-azabicyclo [2.2.1 Jheptan-2-yl)tnethanone |
| 16 | | 8 | 7 | 1000 | (R/S)-(3-fluoro-2-(2H-1,2,3-triazol-2-yl)phenyl)(6-((5-(trifluoromethyl)pyridin-2-yl)oxy)-2-azabicyclo[2.2.1]heptan-2-yl)methanone |
| 17 | | 8 | 3 | 34 | (R/S)-(3-methyl-2-(2H-1,2,3-triazol-2-yl)phenyl)(6-((5-(trifluoromethyl)pyridin-2-yl)oxy)-2-azabicyclo[2.2.1]heptan-2-yl)methanone |
| 18 | | 25 | 23 | 1800 | (R/S)-(2-fluoro-6-(2H-1,2,3-triazol-2-yl)phenyl)(6-((5-(trifluoromethyl)pyridin-2-yl)oxy)-2-azabicyclo[2.2.1]heptan-2-yl)methanone |

-continued

| Ex. No. | Compound | rOX1 $K_i$ (nM) | hOX1 $K_i$ (nM) | hOX2 $K_i$ (nM) | Compound Name |
|---|---|---|---|---|---|
| 19 | 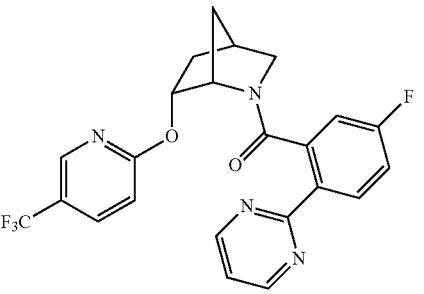 | | 18 | 9 | 945 | (R/S)-(5-fluoro-2-(pyrimidin-2-yl)phenyl)(6-((5-(trifluoromethyl)pyridin-2-yl)oxy)-2-azabicyclo[2.2.1]heptan-2-yl)methanone |
| 20 | 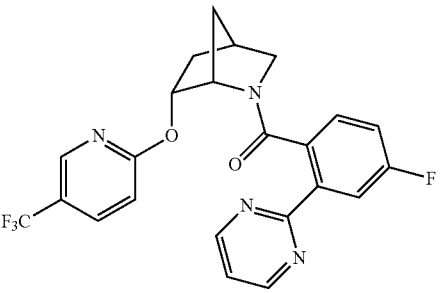 | | 15 | 15 | 2700 | (R/S)-(4-fluoro-2-(pyrimidin-2-yl)phenyl)(-6-((5-(trifluoromethyl)pyridin-2-yl)oxy)-2-azabicyclo[2.2.1]heptan-2-yl)methanone |
| 21 | 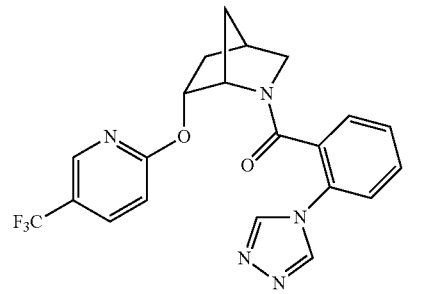 | >10000 | | >1000 | (R/S)-(2-(4H-1,2,4-triazol-4-yl)phenyl)(6-((5-(trifluoromethyl)pyridin-2-yl)oxy)-2-azabicyclo[2.2.1]heptan-2-yl)methanone |
| 22 | 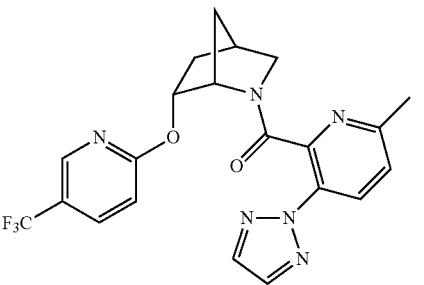 | 25 | 23 | 1000 | (R/S)-(6-methyl-3-(2H-1,2,3-triazol-2-yl)pyridin-2-yl)(6-((5-(trifluoromethyl)pyridin-2-yl)oxy)-2-azabicyclo[2.2.1]heptan-2-yl)methanone |
| 23 | 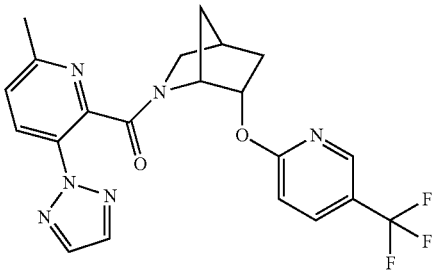 | >10000 | | >10000 | (6-methyl-3-(2H-1,2,3-triazol-2-yl)pyridin-2-yl)((1R,4S,6S)-6-((5-(trifluoromethyl)pyridin-2-yl)oxy)-2-azabicyclo[2.2.1]heptan-2-yl)methanone |

| Ex. No. | Compound | rOX1 K$_i$ (nM) | hOX1 K$_i$ (nM) | hOX2 K$_i$ (nM) | Compound Name |
|---|---|---|---|---|---|
| 24 | 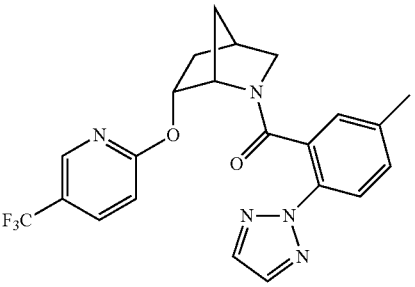 | 20 | 16 | 692 | (6-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone |
| 25 | 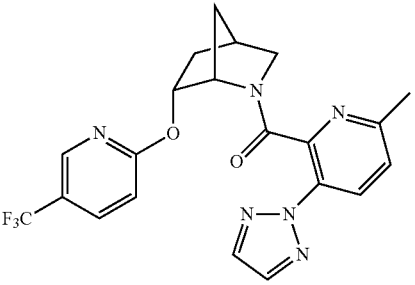 | 17 | 15 | 466 | (6-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone |
| 26 | 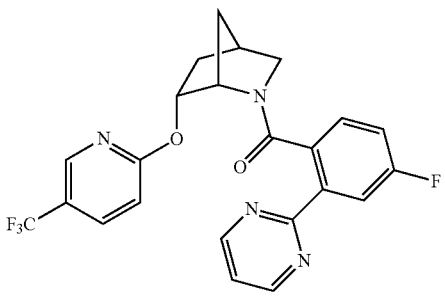 | 12 | 15 | 2100 | (4-fluoro-2-(pyrimidin-2-yl)phenyl)((1S,4R,6R)-6-((5-(trifluoromethyl)pyridin-2-yl)oxy)-2-azabicyclo[2.2.1]heptan-2-yl)methanone |
| 27 | 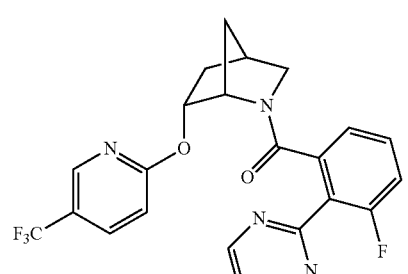 | 4 | 4 | 767 | (3-fluoro-2-(pyrimidin-2-yl)phenyl)((1S,4R,6R)-6-((5-(trifluoromethyl)pyridin-2-yl)oxy)-2-azabicyclo[2.2.1]heptan-2-yl)methanone |
| 28 | 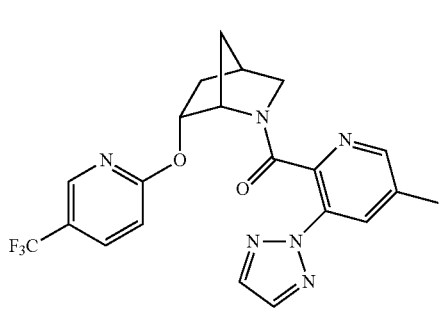 | 32 | 21 | 1600 | (5-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone |

| Ex. No. | Compound | rOX1 K_i (nM) | hOX1 K_i (nM) | hOX2 K_i (nM) | Compound Name |
|---|---|---|---|---|---|
| 29 | | 55 | 47 | >10000 | (6-methyl-2-(2H-1,2,3-triazol-2-yl)pyridin-3-yl)((1S,4R,6R)-6-((5-(trifluoromethyl)pyridin-2-yl)oxy)-2-azabicyclo[2.2.1]heptan-2-yl)methanone |
| 30 | | 19 | 22 | 1700 | (3-(2H-1,2,3-triazol-2-yl)pyridin-2-yl)((1S,4R,6R)-6-((5-(trifluoromethyl)pyridin-2-yl)oxy)-2-azabicyclo[2.2.1]heptan-2-yl)methanone |
| 31 | | 707 | | >10000 | (3-fluoro-2-methoxyphenyl)((1S,4R,6R)-6-((5-(trifluoromethyl)pyridin-2-yl)oxy)-2-azabicyclo[2.2.1]heptan-2-yl)methanone |
| 32 | | 3 | 4 | 143 | (3-methyl-2-(oxazol-2-yl)phenyl)((1S,4R,6R)-6-((5-(trifluoromethyl)pyridin-2-yl)oxy)-2-azabicyclo[2.2.1]heptan-2-yl)methanone |
| 33 | | 74 | 86 | 3500 | (3-fluoro-2-(1H-1,2,3-triazol-1-yl)phenyl)((1S,4R,6R)-6-((5-(trifluoromethyl)pyridin-2-yl)oxy)-2-azabicyclo[2.2.1]heptan-2-yl)methanone |

| Ex. No. | Compound | rOX1 K$_i$ (nM) | hOX1 K$_i$ (nM) | hOX2 K$_i$ (nM) | Compound Name |
| --- | --- | --- | --- | --- | --- |
| 34 | 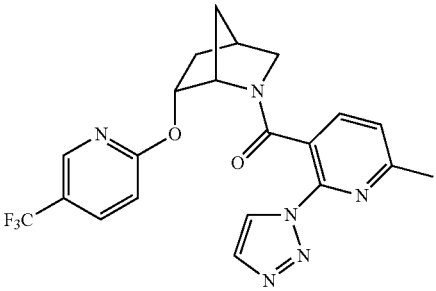 | 117 | 462 | 1100 | (6-methyl-2-(1H-1,2,3-triazol-1-yl)pyridin-3-yl)((1S,4R,6R)-6-((5-(trifluoromethyl)pyridin-2-yl)oxy)-2-azabicyclo[2.2.1]heptan-2-yl)methanone |
| 35 | 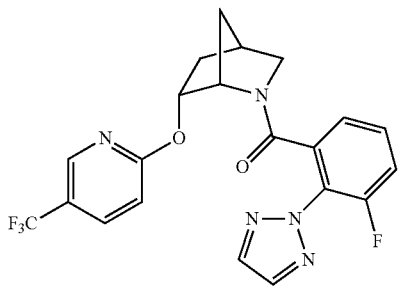 | 8 | 3 | 542 | (3-fluoro-2-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone |
| 36 | 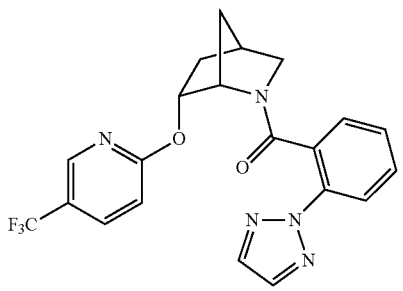 | 5 | 11 | 322 | (2-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone |
| 37 | 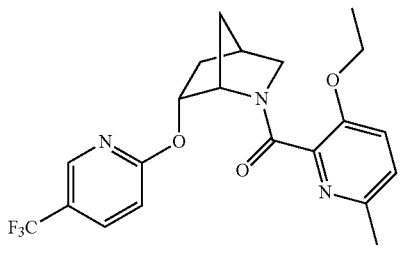 | 170 | 265 | 1800 | (3-ethoxy-6-methylpyridin-2-yl)((1S,4R,6R)-6-((5-(trifluoromethyl)pyridin-2-yl)oxy)-2-azabicyclo[2.2.1]heptan-2-yl)methanone |
| 38 | 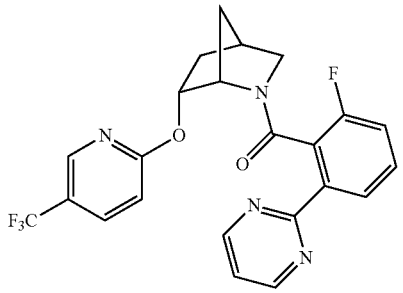 | 8 | 8 | 690 | (2-fluoro-6-(pyrimidin-2-yl)phenyl)((1S,4R,6R)-6-((5-(trifluoromethyl)pyridin-2-yl)oxy)-2-azabicyclo[2.2.1]heptan-2-yl)methanone |

-continued

| Ex. No. | Compound | rOX1 K$_i$ (nM) | hOX1 K$_i$ (nM) | hOX2 K$_i$ (nM) | Compound Name |
|---|---|---|---|---|---|
| 39 | | 132 | 17 | 108 | (2-methoxy-6-(1H-pyrazol-5-yl)phenyl)((1S,4R,6R)-6-((5-(trifluoromethyl)pyridin-2-yl)oxy)-2-azabicyclo[2.2.1]heptan-2-yl)methanone |
| 40 | | 16 | 9 | 340 | (2-methoxy-6-(pyrimidin-2-yl)phenyl)((1S,4R,6R)-6-((5-(trifluoromethyl)pyridin-2-yl)oxy)-2-azabicyclo[2.2.1]heptan-2-yl)methanone |
| 41 | | 4399 | >10000 | | (2-(1,4-dimethyl-1H-pyrazol-5-yl)phenyl)((1S,4R,6R)-6-((5-(trifluorometliyl)pyridin-2-yl)oxy)-2-azabicyclo[2.2.1]heptan-2-yl)methanone |
| 42 | | 184 | 175 | 5800 | (1H-indol-7-yl)((1S,4R,6R)-6-((5-(trifluoromethyl)pyridin-2-yl)oxy)-2-azabicyclo[2.2.1]heptan-2-yl)methanone |
| 43 | | 16 | 8 | 557 | (5-fluoro-2-(2H-1,2,3-triazol-2-yl)phenyl)((1S,4R,6R)-6-((5-(trifluorometliyl)pyridin-2-yl)oxy)-2-azabicyclo[2.2.1]heptan-2-yl)methanone |

-continued

| Ex. No. | Compound | rOX1 K_i (nM) | hOX1 K_i (nM) | hOX2 K_i (nM) | Compound Name |
|---|---|---|---|---|---|
| 44 | 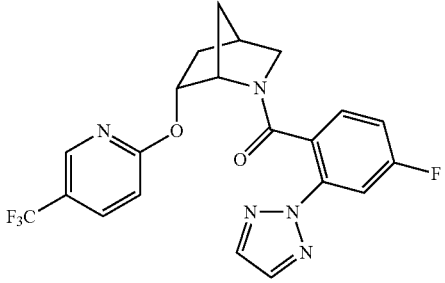 | 22 | 42 | 2198 | (4-fluoro-2-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone |
| 45 | 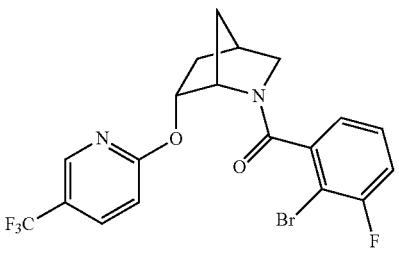 | 60 | 55 | 1500 | (2-bromo-3-fluorophenyl)((1S,4R,6R)-6-((5-(trifluoromethyl)pyridin-2-yl)oxy)-2-azabicyclo[2.2.1]heptan-2-yl)methanone |
| 46 | 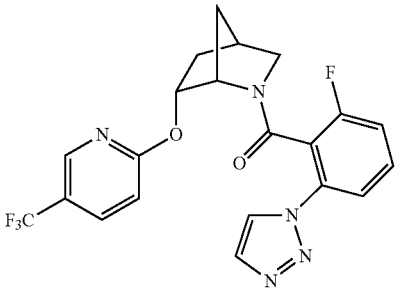 | 10 | 12 | 650 | (2-fluoro-6-(2H-1,2,3-triazol-2-yl)phenyl)((1S,4R,6R)-6-((5-(trifluoromethyl)pyridin-2-yl)oxy)-2-azabicyclo[2.2.1]heptan-2-yl)methanone |
| 47 | 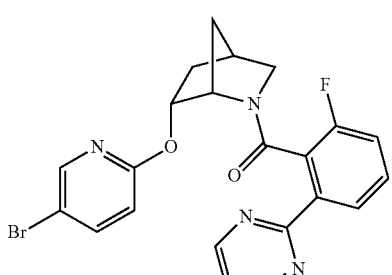 | 7 | 11 | 503 | ((1S,4R,6R)-6-((5-bromopyridin-2-yl)oxy)-2-azabicyclo[2.2.1]heptan-2-yl)(2-fluoro-6-(pyrimidin-2-yl)phenyl)methanone |
| 48 | 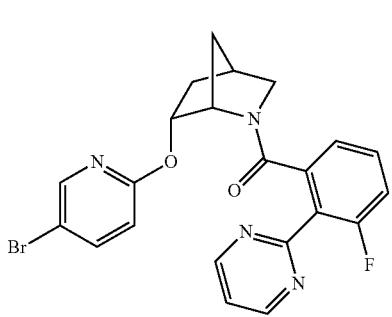 | 3 | 6 | 972 | ((1S,4R,6R)-6-((5-bromopyridin-2-yl)oxy)-2-azabicyclo[2.2.1]heptan-2-yl)(3-fluoro-2-(pyrimidin-2-yl)phenyl)methanone |

| Ex. No. | Compound | rOX1 K$_i$ (nM) | hOX1 K$_i$ (nM) | hOX2 K$_i$ (nM) | Compound Name |
|---|---|---|---|---|---|
| 49 | | 6 | 6 | 507 | (2-(2H-1,2,3-triazol-2-yl)phenyl)((1S,4R,6R)-6-((5-bromopyridin-2-yl)oxy)-2-azabicyclo[2.2.1]heptan-2-yl)methanone |
| 50 | | 7 | 9 | 670 | ((1S,4R,6R)-6-((5-bromopyridin-2-yl)oxy)-2-azabicyclo[2.2.1]heptan-2-yl)(6-methyl-3-(2H-1,2,3-triazol-2-yl)pyridin-2-yl)methanone |
| 51 | | 294 | | 676 | (2-(2H-1,2,3-triazol-2-yl)phenyl)((1S,4R,6R)-6-((3-(trifluoromethyl)pyridin-2-yl)oxy)-2-azabicyclo[2.2.1]heptan-2-yl)methanone |
| 52 | | 550 | | 4000 | (6-methyl-3-(2H-1,2,3-triazol-2-yl)pyridin-2-yl)((1S,4R,6R)-6-((3-(trifluoromethyl)pyridin-2-yl)oxy)-2-azabicyclo[2.2.1]heptan-2-yl)methanone |
| 53 | | 3 | 3 | 165 | (2-(2H-1,2,3-triazol-2-yl)phenyl)((1S,4S,6R)-6-((5-(trifluoromethyl)pyridin-2-yl)amino)-2-azabicyclo[2.2.1]heptan-2-yl)methanone |

| Ex. No. | Compound | rOX1 $K_i$ (nM) | hOX1 $K_i$ (nM) | hOX2 $K_i$ (nM) | Compound Name |
|---|---|---|---|---|---|
| 54 | 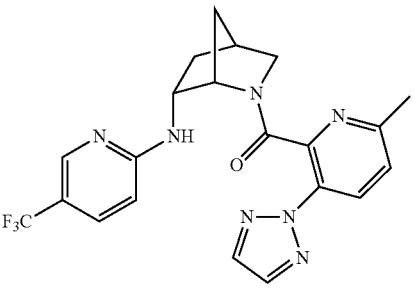 | 5 | 6 | 132 | (6-methyl-3-(2H-1,2,3-triazol-2-yl)pyridin-2-yl)((1S,4S,6R)-6-((5-(trifluoromethyl)pyridin-2-yl)amino)-2-azabicyclo[2.2.1]heptan-2-yl)methanone |
| 55 | 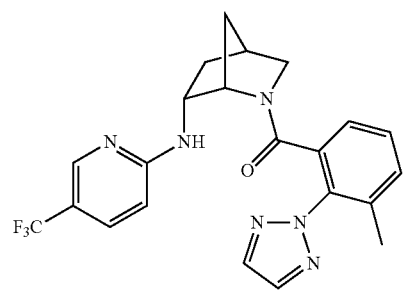 | 3 | 3 | 46 | (3-methyl-2-(2H-1,2,3-triazol-2-yl)phenyl)((1S,4S,6R)-6-((5-(trifluoromethyl)pyridin-2-yl)amino)-2-azabicyclo[2.2.1]heptan-2-yl)methanone |
| 56 | 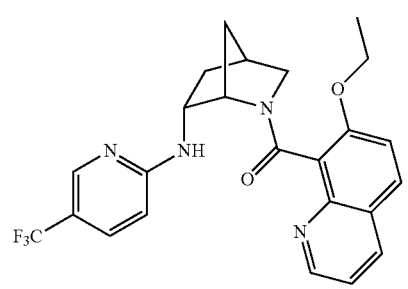 | 8 | 10 | 192 | (7-ethoxyquinolin-8-yl)((1S,4S,6R)-6-((5-(trifluoromethyl)pyridin-2-yl)amino)-2-azabicyclo[2.2.1]heptan-2-yl)methanone |
| 57 | 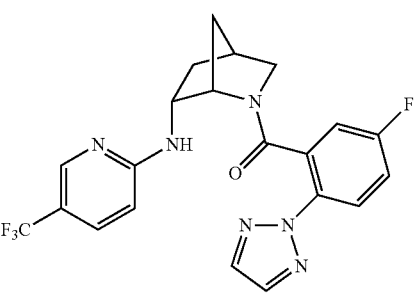 | 6 | 5 | 252 | (5-fluoro-2-(2H-1,2,3-triazol-2-yl)phenyl)((1S,4S,6R)-6-((5-(trifluoromethyl)pyridin-2-yl)amino)-2-azabicyclo[2.2.1]heptan-2-yl)methanone |
| 58 | 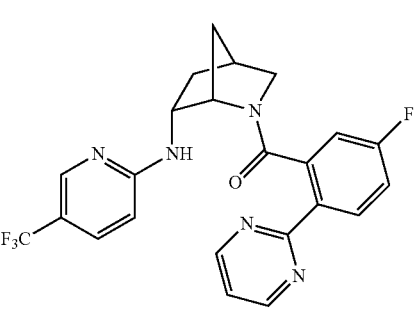 | 4 | 2 | 181 | (5-fluoro-2-(pyrimidin-2-yl)phenyl)((1S,4S,6R)-6-((5-(trifluoromethyl)pyridin-2-yl)amino)-2-azabicyclo[2.2.1]heptan-2-yl)methanone |

| Ex. No. | Compound | rOX1 K$_i$ (nM) | hOX1 K$_i$ (nM) | hOX2 K$_i$ (nM) | Compound Name |
| --- | --- | --- | --- | --- | --- |
| 59 | | 6 | 9 | 213 | (2-(2H-1,2,3-triazol-2-yl)phenyl)((1S,4S,6R)-6-((5-(trifluoromethyl)pyrazin-2-yl)amino)-2-azabicyclo[2.2.1]heptan-2-yl)methanone |
| 60 | | | | | (2-(2H-1,2,3-triazol-2-yl)phenyl)((1S,4S,6R)-6-((5-(trifluoromethyl)pyrimidin-2-yl)amino)-2-azabicyclo[2.2.1]heptan-2-yl)methanone |
| 61 | | | | | (6-methyl-3-(2H-1,2,3-triazol-2-yl)pyridin-2-yl)((1S,4S,6R)-6-((5-(trifluoromethyl)pyrazin-2-yl)amino)-2-azabicyclo[2.2.1]heptan-2-yl)methanone |
| 62 | | | | | (6-methyl-3-(2H-1,2,3-triazol-2-yl)pyridin-2-yl)((1S,4S,6R)-6-((5-(trifluoromethyl)pyrimidin-2-yl)amino)-2-azabicyclo[2.2.1]heptan-2-yl)methanone |
| 63 | | | | | (4-methyl-2-(2H-1,2,3-triazol-2-yl)phenyl)((1S,4S,6R)-6-((5-(trifluoromethyl)pyridin-2-yl)amino)-2-azabicyclo[2.2.1]heptan-2-yl)methanone |

| Ex. No. | Compound | rOX1 $K_i$ (nM) | hOX1 $K_i$ (nM) | hOX2 $K_i$ (nM) | Compound Name |
|---|---|---|---|---|---|
| 64 | | | | | (4-methyl-2-(2H-1,2,3-triazol-2-yl)phenyl)((1S,4S,6R)-6-((5-(trifluoromethyl)pyrazin-2-yl)amino)-2-azabicyclo[2.2.1]heptan-2-yl)methanone |
| 65 | | | | | (4-methyl-2-(2H-1,2,3-triazol-2-yl)phenyl)((1S,4S,6R)-6-((5-(trifluoromethyl)pyrimidin-2-yl)amino)-2-azabicyclo[2.2.1]heptan-2-)methanone |
| 66 | | | | | (3-fluoro-2-(pyrimidin-2-yl)phenyl)((1S,4S,6R)-6-((5-(trifluoromethyl)pyridin-2-yl)amino)-2-azabicyclo[2.2.1]heptan-2-yl)methanone |
| 67 | | | | | (3-fluoro-2-(pyrimidin-2-yl)phenyl)((1S,4S,6R)-6-((5-(trifluoromethyl)pyrazin-2-yl)amino)-2-azabicyclo[2.2.1]heptan-2-yl)methanone |
| 68 | | | | | (3-fluoro-2-(pyrimidin-2-yl)phenyl)((1S,4S,6R)-6-((5-(trifluoromethyl)pyrimidin-2-yl)amino)-2-azabicyclo[2.2.1]heptan-2-yl)methanone |

| Ex. No. | Compound | rOX1 K$_i$ (nM) | hOX1 K$_i$ (nM) | hOX2 K$_i$ (nM) | Compound Name |
|---|---|---|---|---|---|
| 69 | | | | | (2-(3-methyl-1,2,4-oxadiazol-5-yl)phenyl)((1S,4S,6R)-6-((5-(trifluoromethyl)pyridin-2-yl)amino)-2-azabicyclo[2.2.1]heptan-2-yl)methanone |
| 70 | | | | | (3-fluoro-2-(3-methyl-1,2,4-oxadiazol-5-yl)phenyl)((1S,4S,6R)-6-((5-(trifluoromethyl)pyridin-2-yl)amino)-2-azabicyclo[2.2.1]heptan-2-yl)methanone |
| 71 | | | | | (3-fluoro-2-(3-methyl-1,2,4-oxadiazol-5-yl)phenyl)((1S,4R,6R)-6-((5-(trifluoromethyl)pyridin-2-yl)oxy)-2-azabicyclo[2.2.1]heptan-2-yl)methanone |
| 72 | | | | | (3-fluoro-2-(3-methyl-1,2,4-oxadiazol-5-yl)phenyl)((1S,4R,6R)-6-((5-(trifluoromethyl)pyridin-2-yl)oxy)-2-azabicyclo[2.2.1]heptan-2-yl)methanone |
| 73 | | | | | (3-fluoro-2-(pyrimidin-2-yl)phenyl)((1S,4R,6R)-6-((5-(trifluoromethyl)pyridin-2-yl)oxy)-2-azabicyclo[2.2.2]octan-2-yl)methanone |

| Ex. No. | Compound | rOX1 $K_i$ (nM) | hOX1 $K_i$ (nM) | hOX2 $K_i$ (nM) | Compound Name |
|---|---|---|---|---|---|
| 74 | | | | | (3-fluoro-2-(pyrimidin-2-yl)phenyl)((1S,4R,6R)-6-((5-(trifluoromethyl)pyrazin-2-yl)oxy)-2-azabicyclo[2.2.2]octan-2-yl)methanone |
| 75 | | | | | (3-fluoro-2-(pyrimidin-2-yl)phenyl)((1S,4R,6R)-6-((5-(trifluoromethyl)pyrimidin-2-yl)oxy)-2-azabicyclo[2.2.2]octan-2-yl)methanone |
| 76 | | | | | (6-methyl-3-(2H-1,2,3-triazol-2-yl)pyridin-2-yl)((1S,4R,6R)-6-((5-(trifluoromethyl)pyridin-2-yl)oxy)-2-azabicyclo[2.2.2]octan-2-yl)methanone |
| 77 | | | | | (6-methyl-3-(2H-1,2,3-triazol-2-yl)pyridin-2-yl)((1S,4R,6R)-6-((5-(trifluoromethyl)pyrazin-2-yl)oxy)-2-azabicyclo[2.2.2]octan-2-yl)methanone |
| 78 | | | | | (6-methyl-3-(2H-1,2,3-triazol-2-yl)pyridin-2-yl)((1S,4R,6R)-6-((5-(trifluoromethyl)pyrimidin-2-yl)oxy)-2-azabicyclo[2.2.2]octan-2-yl)methanone |

| Ex. No. | Compound | rOX1 K<sub>i</sub> (nM) | hOX1 K<sub>i</sub> (nM) | hOX2 K<sub>i</sub> (nM) | Compound Name |
|---|---|---|---|---|---|
| 79 | | | | | (6-methyl-3-(2H-1,2,3-triazol-2-yl)pyridin-2-yl)((1S,4R,6R)-6-((5-(trifluoromethyl)pyrimidin-2-yl)amino)-2-azabicyclo[2.2.2]octan-2-yl)methanone |
| 80 | | | | | (3-fluoro-2-(pyrimidin-2-yl)phenyl)((1S,4R,6R)-6-((5-(trifluoromethyl)pyrazin-2-yl)amino)-2-azabicyclo[2.2.2]octan-2-yl)methanone |
| 81 | | | | | (3-fluoro-2-(pyrimidin-2-yl)phenyl)((1S,4R,6R)-6-((5-(trifluoromethyl)pyrimidin-2-yl)amino)-2-azabicyclo[2.2.2]octan-2-yl)methanone |
| 82 | | | | | (6-methyl-3-(2H-1,2,3-triazol-2-yl)pyridin-2-yl)((1S,4R,6R)-6-((5-(trifluoromethyl)pyridin-2-yl)amino)-2-azabicyclo[2.2.2]octan-2-yl)methanone |
| 83 | | | | | (6-methyl-3-(2H-1,2,3-triazol-2-yl)pyridin-2-yl)((1S,4R,6R)-6-((5-(trifluoromethyl)pyrazin-2-yl)amino)-2-azabicyclo[2.2.2]octan-2-yl)methanone |

| Ex. No. | Compound | rOX1 $K_i$ (nM) | hOX1 $K_i$ (nM) | hOX2 $K_i$ (nM) | Compound Name |
|---|---|---|---|---|---|
| 84 | 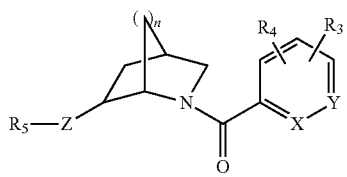 | | | | (6-methyl-3-(2H-1,2,3-triazol-2-yl)pyridin-2-yl)((1S,4R,6R)-6-((5-(trifluoromethyl)pyrimidin-2-yl)amino)-2-azabicyclo[2.2.2]octan-2-yl)methanone |

What is claimed:

1. A method of treating a subject suffering from or diagnosed with depression, manic depression, anxiety, stress, post-traumatic stress disorder, panic disorders, or addiction, said method comprising administering to the subject an effective amount of a compound of formula I:

or an enantiomer or diastereomer thereof;
or a pharmaceutically acceptable salt thereof;
wherein
X is N or $CR_1$;
Y is N or $CR_2$;
$R_1$ is H, alkoxy, halo, triazolyl, pyrimidinyl, oxazolyl, isoxazolyl, oxadiazolyl, or pyrazolyl;
$R_2$ is H, alkyl, alkoxy, or halo;
Z is NH or O;
$R_3$ is H, alkyl, alkoxy, halo, or triazolyl;
$R_4$ is H or alkyl;
or $R_3$ and $R_4$, together with the atoms to which they are attached, form a 6-membered aryl ring or a 5- or 6-membered heteroaryl ring;
$R_5$ is pyridyl, pyrazinyl, or pyrimidinyl, wherein the pyridyl, pyrazinyl, or pyrimidinyl is optionally substituted with halo or alkyl; and
n is 1 or 2.

2. The method of claim 1, wherein the subject is suffering from or diagnosed with post-traumatic stress disorder or panic disorders.

3. The method of claim 1, wherein Z is O.

4. The method of claim 1, wherein X is $CR_1$ and Y is $CR_2$.

5. The method of claim 1, wherein $R_1$ is alkoxy, halo, triazolyl, pyrimidinyl, oxazolyl, isoxazolyl, oxadiazolyl, or pyrazolyl.

6. The method of claim 5, wherein $R_1$ is alkoxy, halo, triazolyl, or pyrimidinyl.

7. The method of claim 1, wherein $R_2$ is H, alkyl, or halo.

8. The method of claim 1, wherein $R_2$ is H.

9. The method of claim 1, wherein $R_3$ is H.

10. The method of claim 1, wherein $R_4$ is H.

11. The method of claim 1, wherein $R_5$ is pyridyl, optionally substituted with halo or alkyl.

12. The method of claim 11, wherein alkyl is trihaloalkyl.

13. The method of claim 1, wherein n is 1.

14. The method of claim 1, wherein n is 2.

15. A method of treating a subject suffering from or diagnosed with depression, manic depression, anxiety, stress, post-traumatic stress disorder, panic disorders, or addiction, said method comprising administering to the subject an effective amount of a compound selected from the group consisting of

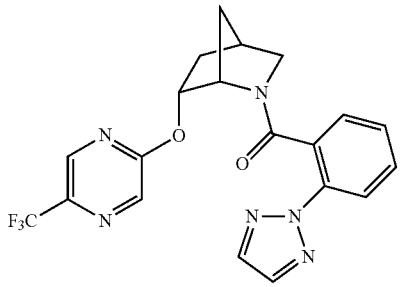 [SMILES: O=C(c1ccccc1-n1nccn1)N1CC2CC(Oc3cnc(C(F)(F)F)cn3)C1C2]

(R/S)-(2-(2H-1,2,3-triazol-2-yl)phenyl)(6-((5-(trifluoromethyl)pyrazin-2-yl)oxy)-2-azabicyclo[2.2.1]heptan-2-yl)methanone

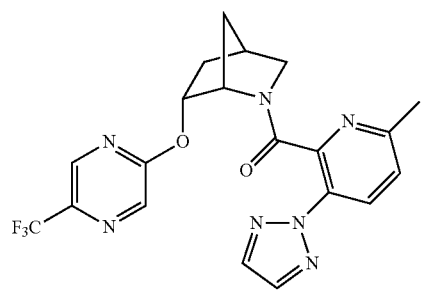 [SMILES: Cc1ccc(-n2nccn2)c(C(=O)N2CC3CC(Oc4cnc(C(F)(F)F)cn4)C2C3)n1]

(R/S)-((6-methyl-3-(2H-1,2,3-triazol-2-yl)pyridin-2-yl)(6-((5-(trifluoromethyl)pyrazin-2-yl)oxy)-2-azabicyclo[2.2.1]heptan-2-yl)methanone

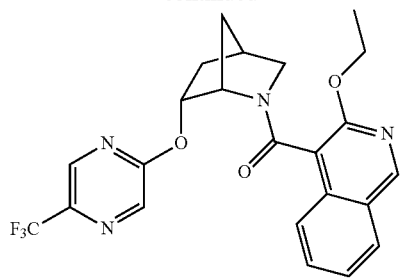

(R/S)-(3-ethoxyisoquinolin-4-yl)
((5-(trifluoromethyl)pyrazin-2-yl)oxy)-2-
azabicyclo[2.2.1]heptan-2-yl)methanone

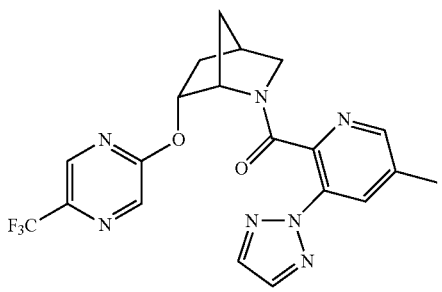 [SMILES: Cc1cnc(C(=O)N2CC3CC(Oc4cnc(C(F)(F)F)cn4)C2C3)c(-n2nccn2)c1]

(R/S)-5-methyl-3-(2H-1,2,3-triazol-2-yl)
pyridin-2-yl)(6-((5-(trifluoromethyl)pyrazin-2-yl)oxy)-2-
azabicyclo[2.2.1]heptan-2-yl)methanone

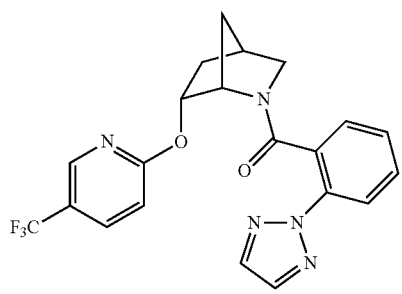

(R/S)-(2-(2H-1,2,3-triazol-2-yl)phenyl)
(6-((5-(trifluoromethyl)pyrazin-2-yl)oxy)-2-
azabicyclo[2.2.1]heptan-2-yl)methanone

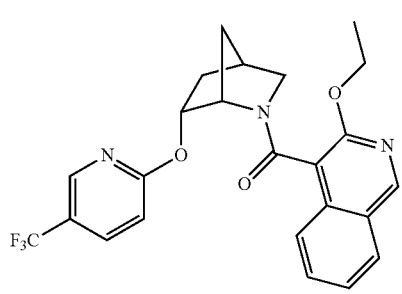 [SMILES: CCOc1ncc2ccccc2c1C(=O)N1CC2CC(Oc3ccc(C(F)(F)F)cn3)C1C2]

(R/S)-(3-ethoxyisoquinolin-4-yl)
(6-((5-(trifluoromethyl)pyridin-2-yl)oxy)-2-
azabicyclo[2.2.1]heptan-2-yl)methanone

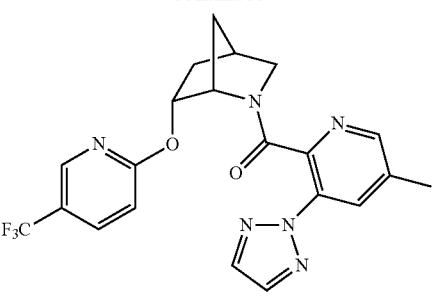 [SMILES: Cc1cnc(C(=O)N2CC3CC(Oc4ccc(C(F)(F)F)cn4)C2C3)c(-n2nccn2)c1]

(R/S)-(5-methyl-3-(2H-1,2,3-triazol-2-yl)
pyridin-2-yl)6-((5-(trifluoromethyl)pyridin-2-yl)oxy)-2-
azabicyclo[2.2.1]heptan-2-yl)methanone

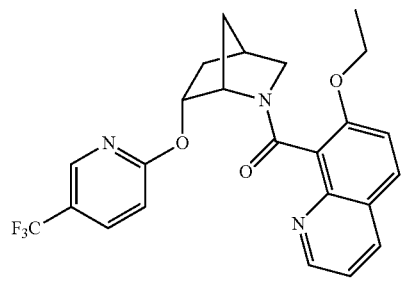 [SMILES: CCOc1ccc2cccnc2c1C(=O)N1CC2CC(Oc3ccc(C(F)(F)F)cn3)C1C2]

(R/S)-(7-ethoxyisoquinolin-8-yl)
(6-((5-(trifluoromethyl)pyridin-2-yl)oxy)-2-
azabicyclo[2.2.1]heptan-2-yl)methanone

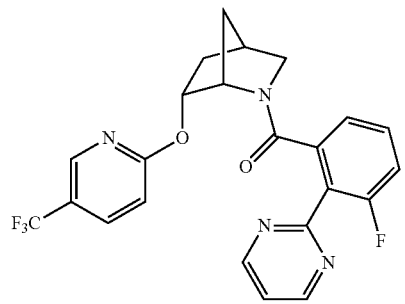 [SMILES: O=C(c1cccc(F)c1-c1ncccn1)N1CC2CC(Oc3ccc(C(F)(F)F)cn3)C1C2]

(R/S)-(3-fluoro-2-(pyrimidin-2-yl)
phenyl)(6-((5-(trifluoromethyl)pyridin-2-yl)oxy)-2-
azabicyclo[2.2.1]heptan-2-yl)methanone

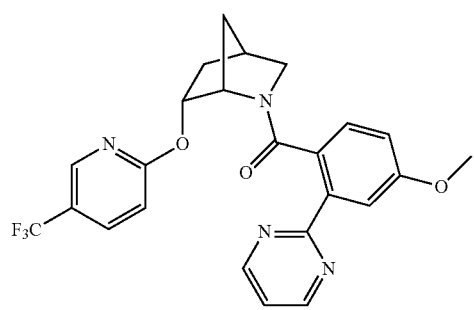 [SMILES: COc1ccc(C(=O)N2CC3CC(Oc4ccc(C(F)(F)F)cn4)C2C3)c(-c2ncccn2)c1]

(R/S)-(4-methoxy-2-(pyrimidin-2-yl)
phenyl)(6-((5-(trifluoromethyl)pyridin-2-yl)oxy)-2-
azabicyclo[2.2.1]heptan-2-yl)methanone -continued

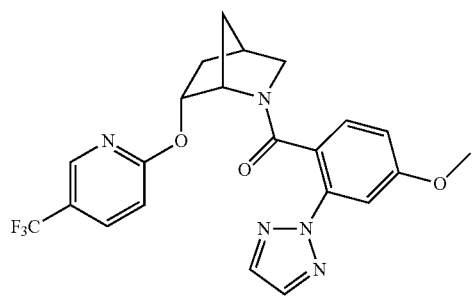

(R/S)-4-methoxy-2-(2H-1,2,3-triazol-2-yl)
phenyl)(6-((5-(trifluoromethyl)pyridin-2-yl)oxy)-2-
azabicyclo[2.2.1]heptan-2-yl)methanone

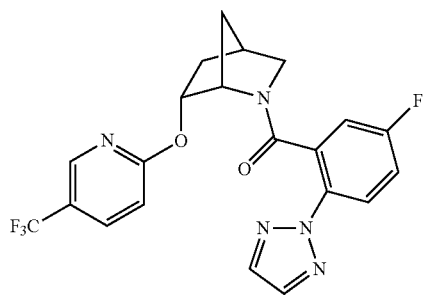

(R/S)-(5-fluoro-2-(2H-1,2,3-triazol-2-yl)
phenyl)(6-((5-(trifluoromethyl)pyridin-2-yl)oxy)-2-
azabicyclo[2.2.1]heptan-2-yl)methanone

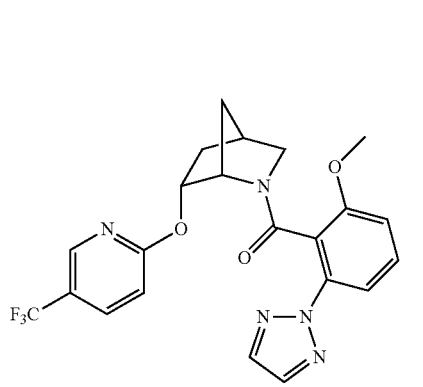

(R/S)-2-methoxy-6-(2H-1,2,3-triazol-2-yl)
phenyl)(6-((5-(trifluoromethyl)pyridin-2-yl)oxy)-2-
azabicyclo[2.2.1]heptan-2-yl)methanone

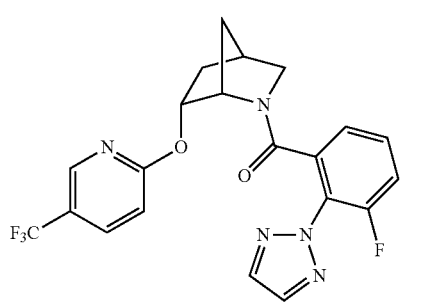

(R/S)-(3-fluoro-2-(2H-1,2,3-triazol-2-yl)
phenyl)(6-((5-(trifluoromethyl)pyridin-2-yl)oxy)-2-
azabicyclo[2.2.1]heptan-2-yl)methanone -continued

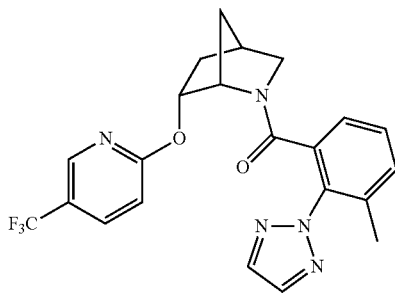

(R/S)-(3-methyl-2-(2H-1,2,3-triazol-2-yl)
phenyl)(6-((5-(trifluoromethyl)pyridin-2-yl)oxy)-2-
azabicyclo[2.2.1]heptan-2-yl)methanone

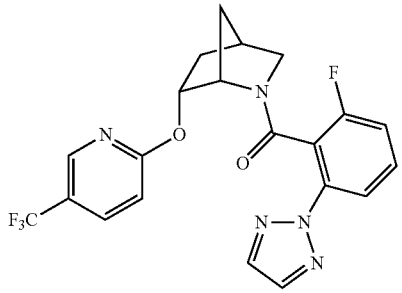

(R/S)-(2-fluoro-6-(2H-1,2,3-triazol-2-yl)
phenyl)(6-((5-(trifluoromethyl)pyridin-2-yl)oxy)-2-
azabicyclo[2.2.1]heptan-2-yl)methanone

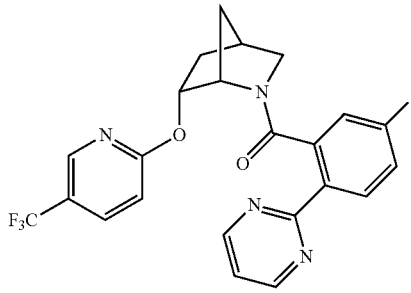

(R/S)-(5-fluoro-2-(pyrimidin-2-yl)
phenyl)(6-((5-(trifluoromethyl)pyridin-2-yl)oxy)-2-
azabicyclo[2.2.1]heptan-2-yl)methanone

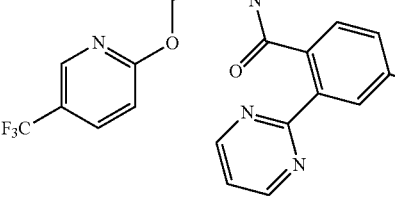

(R/S)-(4-fluoro-2-(pyrimidin-2-yl)
phenyl)(6-((5-(trifluoromethyl)pyridin-2-yl)oxy)-2-
azabicyclo[2.2.1]heptan-2-yl)methanone 123
-continued

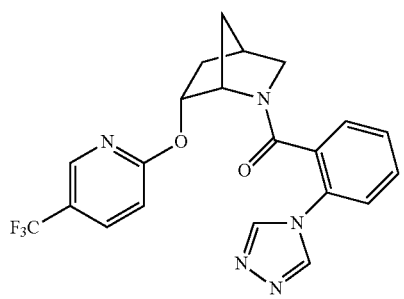 [SMILES: O=C(c1ccccc1-n1cnnc1)N1CC2CC(Oc3ccc(C(F)(F)F)cn3)C1C2]

(R/S)-(2-(4H-1,2,4-triazol-4-yl)
phenyl)(6-((5-(trifluoromethyl)pyridin-2-yl)oxy)-2-
azabicyclo[2.2.1]heptan-2-yl)methanone

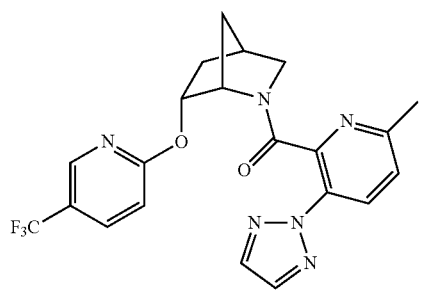 [SMILES: Cc1ccc(-n2nccn2)c(C(=O)N2CC3CC(Oc4ccc(C(F)(F)F)cn4)C2C3)n1]

(R/S)-(6-methyl-3-(2H,1,2,3-triazol-2-yl)
pyridin-2-yl)(6-((5-(trifluoromethyl)pyridin-2-yl)oxy)-2-
azabicyclo[2.2.1]heptan-2-yl)methanone

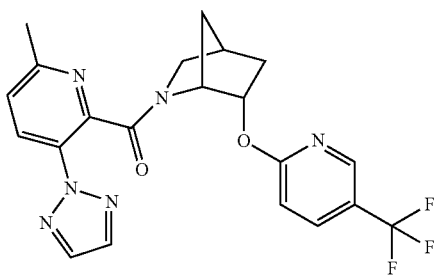 [SMILES: Cc1ccc(-n2nccn2)c(C(=O)N2CC3CC(Oc4ccc(C(F)(F)F)cn4)C2C3)n1]

(6-methyl-3-(2H,1,2,3-triazol-2-yl)
pyridin-2-yl)((1R,4S,6S)-6-((5-(trifluoromethyl)pyridin-
2-yl)oxy)-2-azabicyclo[2.2.1]heptan-2-yl)methanone

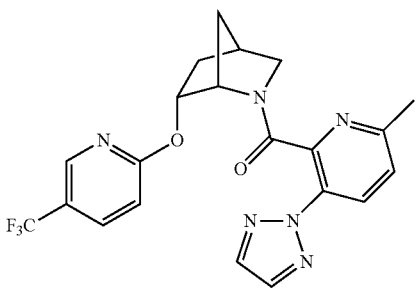 [SMILES: Cc1ccc(-n2nccn2)c(C(=O)N2CC3CC(Oc4ccc(C(F)(F)F)cn4)C2C3)n1]

(6-methyl-3-(2H,1,2,3-triazol-2-yl)
pyridin-2-yl)((1S,4R,6R)-6-((5-(trifluoromethyl)pyridin-
2-yl)oxy)-2-azabicyclo[2.2.1]heptan-2-yl)methanone 124
-continued

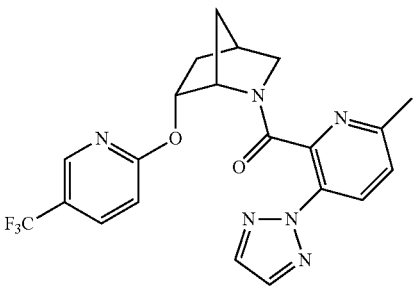

(6-methyl-3-(2H,1,2,3-triazol-2-yl)
pyridin-2-yl)((1S,4R,6R)-6-((5-(trifluoromethyl)pyridin-
2-yl)oxy)-2-azabicyclo[2.2.1]heptan-2-yl)methanone

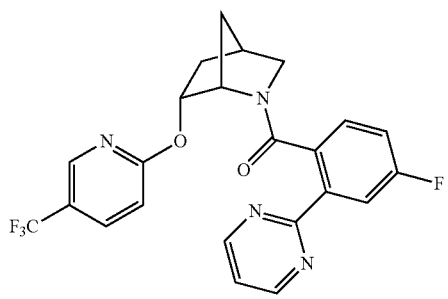 [SMILES: O=C(c1ccc(F)cc1-c1ncccn1)N1CC2CC(Oc3ccc(C(F)(F)F)cn3)C1C2]

(4-fluoro-2-(pyrimidin-2-yl)
phenyl)((1S,4R,6R)-6-((5-(trifluoromethyl)pyridin-
2-yl)oxy)-2-azabicyclo[2.2.1]heptan-2-yl)methanone

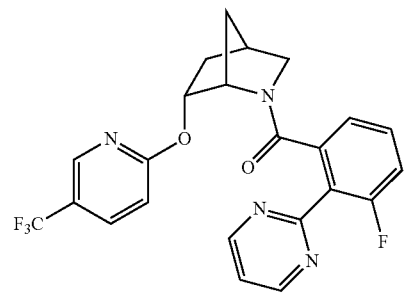

(3-fluoro-2-(pyrimidin-2-yl)
phenyl)((1S,4R,6R)-6-((5-(trifluoromethyl)pyridin-
2-yl)oxy)-2-azabicyclo[2.2.1]heptan-2-yl)methanone

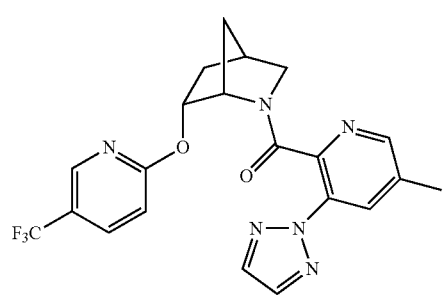 [SMILES: Cc1cnc(C(=O)N2CC3CC(Oc4ccc(C(F)(F)F)cn4)C2C3)c(-n2nccn2)c1]

(5-methyl-3-(2H-1,2,3-triazol-2-yl)
pyridin-2-yl)((1S,4R,6R)-6-((5-(trifluoromethyl)pyridin-
2-yl)oxy)-2-azabicyclo[2.2.1]heptan-2-yl)methanone -continued

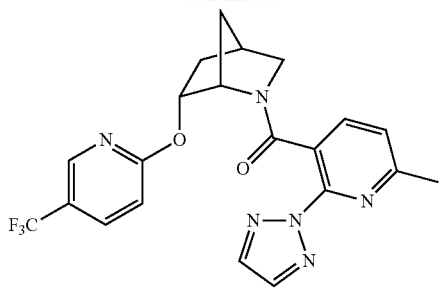 [SMILES: Cc1ccc(C(=O)N2CC3CC(Oc4ccc(C(F)(F)F)cn4)C2C3)c(-n2nccn2)n1]

(6-methyl-2-(2H-1,2,3-triazol-2-yl)
pyridin-3-yl)((1S,4R,6R)-6-((5-(trifluoromethyl)pyridin-
2-yl)oxy)-2-azabicyclo[2.2.1]heptan-2-yl)methanone

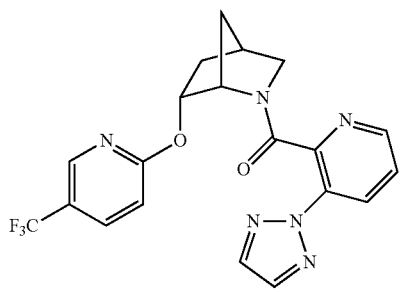 [SMILES: O=C(c1ncccc1-n1nccn1)N1CC2CC(Oc3ccc(C(F)(F)F)cn3)C1C2]

(3-(2H-1,2,3-triazol-2-yl)
pyridin-2-yl)((1S,4R,6R)-6-((5-(trifluoromethyl)pyridin-
2-yl)oxy)-2-azabicyclo[2.2.1]heptan-2-yl)methanone

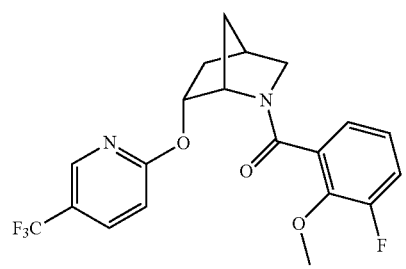

(3-fluoro-2-methoxyphenyl)
((1S,4R,6R)-6-((5-(trifluoromethyl)pyridin-
2-yl)oxy)-2-azabicyclo[2.2.1]heptan-2-yl)methanone

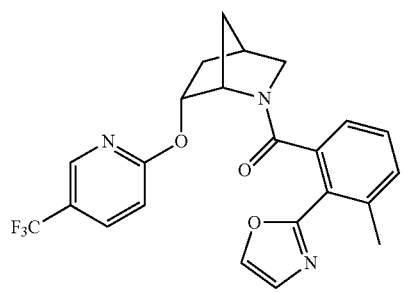 [SMILES: Cc1cccc(C(=O)N2CC3CC(Oc4ccc(C(F)(F)F)cn4)C2C3)c1-c1ncco1]

(3-methyl-2-(oxazol-2-yl)phenyl)
((1S,4R,6R)-6-((5-(trifluoromethyl)pyridin-
2-yl)oxy)-2-azabicyclo[2.2.1]heptan-2-yl)methanone -continued

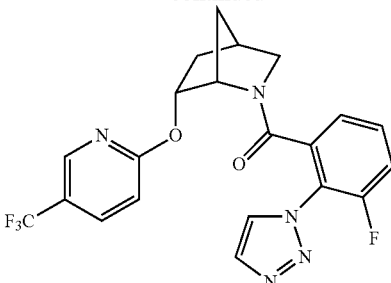

(3-fluoro-2-(1H-1,2,3-triazol-1-yl)phenyl)
((1S,4R,6R)-6-((5-(trifluoromethyl)pyridin-
2-yl)oxy)-2-azabicyclo[2.2.1]heptan-2-yl)methanone

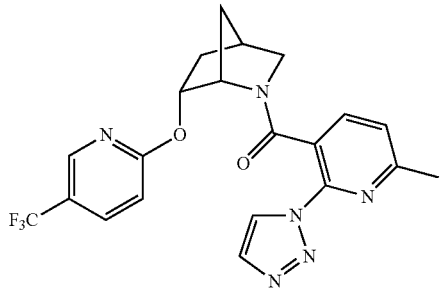 [SMILES: Cc1ccc(C(=O)N2CC3CC(Oc4ccc(C(F)(F)F)cn4)C2C3)c(-n2ccnn2)n1]

(6-methyl-2-(1H-1,2,3-triazol-1-yl)pyridin-3-yl)
((1S,4R,6R)-6-((5-(trifluoromethyl)pyridin-
2-yl)oxy)-2-azabicyclo[2.2.1]heptan-2-yl)methanone

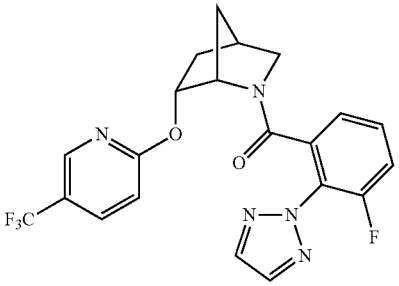

(3-fluoro-2-(2H-1,2,3-triazol-2-yl)phenyl)
((1S,4R,6R)-6-((5-(trifluoromethyl)pyridin-
2-yl)oxy)-2-azabicyclo[2.2.1]heptan-2-yl)methanone

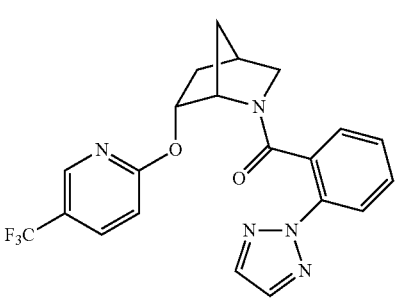

(2-(2H-1,2,3-triazol-2-yl)phenyl)
((1S,4R,6R)-6-((5-(trifluoromethyl)pyridin-
2-yl)oxy)-2-azabicyclo[2.2.1]heptan-2-yl)methanone 127
-continued

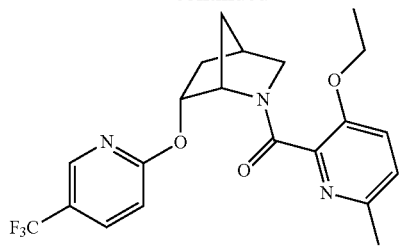 [SMILES: CCOc1ccc(C)nc1C(=O)N1CC2CC(Oc3ccc(C(F)(F)F)cn3)C1C2]

(3-ethoxy-6-methylpyridin-2-yl)
((1S,4R,6R)-6-((5-(trifluoromethyl)pyridin-
2-yl)oxy)-2-azabicyclo[2.2.1]heptan-2-yl)methanone

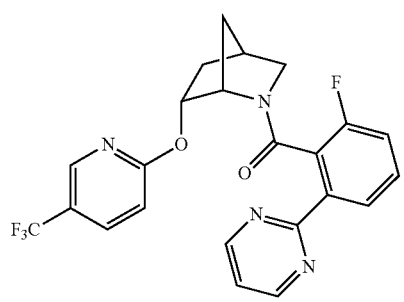 [SMILES: O=C(c1c(F)cccc1-c1ncccn1)N1CC2CC(Oc3ccc(C(F)(F)F)cn3)C1C2]

(2-fluoro-6-(pyrimidin-2-yl)phenyl)
((1S,4R,6R)-6-((5-(trifluoromethyl)pyridin-
2-yl)oxy)-2-azabicyclo[2.2.1]heptan-2-yl)methanone

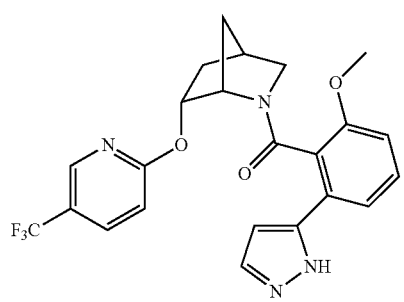 [SMILES: COc1cccc(-c2ccn[nH]2)c1C(=O)N1CC2CC(Oc3ccc(C(F)(F)F)cn3)C1C2]

(2-methoxy-6-(1H-pyrazol-5-yl)phenyl)
((1S,4R,6R)-6-((5-(trifluoromethyl)pyridin-
2-yl)oxy)-2-azabicyclo[2.2.1]heptan-2-yl)methanone

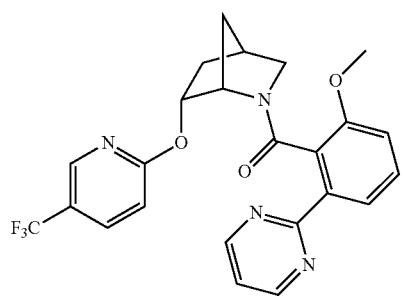 [SMILES: COc1cccc(-c2ncccn2)c1C(=O)N1CC2CC(Oc3ccc(C(F)(F)F)cn3)C1C2]

(2-methoxy-6-(pyrimidin-2-yl)phenyl)
((1S,4R,6R)-6-((5-(trifluoromethyl)pyridin-
2-yl)oxy)-2-azabicyclo[2.2.1]heptan-2-yl)methanone 128
-continued

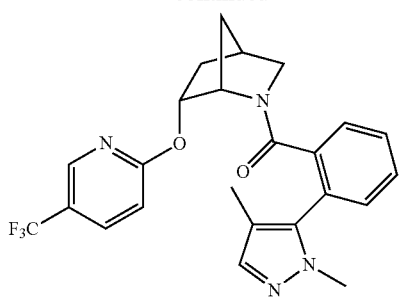 [SMILES: Cc1cnn(C)c1-c1ccccc1C(=O)N1CC2CC(Oc3ccc(C(F)(F)F)cn3)C1C2]

(2-(1,4-dimethyl-1H-pyrazol-5-yl)phenyl)
((1S,4R,6R)-6-((5-(trifluoromethyl)pyridin-
2-yl)oxy)-2-azabicyclo[2.2.1]heptan-2-yl)methanone

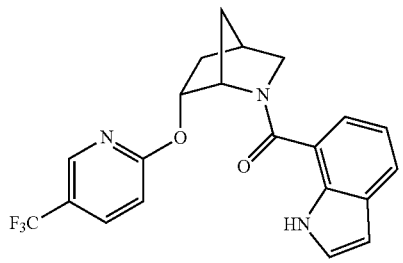 [SMILES: O=C(c1cccc2cc[nH]c12)N1CC2CC(Oc3ccc(C(F)(F)F)cn3)C1C2]

(1H-indol-7-yl)((1S,4R,6R)-6-((5-
(trifluoromethyl)pyridin-2-yl)oxy)-2-
azabicyclo[2.2.1]heptan-2-yl)methanone

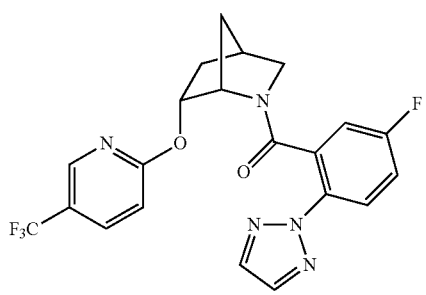 [SMILES: O=C(c1cc(F)ccc1-n1nccn1)N1CC2CC(Oc3ccc(C(F)(F)F)cn3)C1C2]

(5-fluoro-2-(2H-1,2,3-triazol-2-yl)phenyl)
((1S,4R,6R)-6-((5-(trifluoromethyl)pyridin-
2-yl)oxy)-2-azabicyclo[2.2.1]heptan-2-yl)methanone

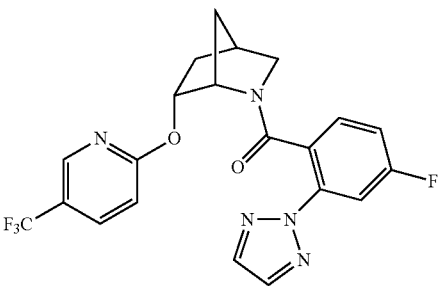 [SMILES: O=C(c1ccc(F)cc1-n1nccn1)N1CC2CC(Oc3ccc(C(F)(F)F)cn3)C1C2]

(4-fluoro-2-(2H-1,2,3-triazol-2-yl)phenyl)
((1S,4R,6R)-6-((5-(trifluoromethyl)pyridin-
2-yl)oxy)-2-azabicyclo[2.2.1]heptan-2-yl)methanone

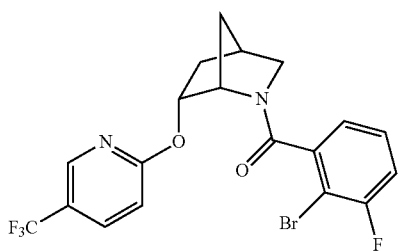 [SMILES: O=C(c1cccc(F)c1Br)N1CC2CC(Oc3ccc(C(F)(F)F)cn3)C1C2]

(2-bromo-3-fluorophenyl)
((1S,4R,6R)-6-((5-(trifluoromethyl)pyridin-
2-yl)oxy)-2-azabicyclo[2.2.1]heptan-2-yl)methanone

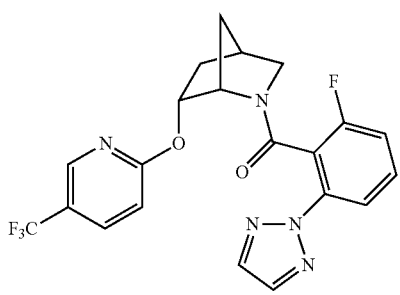

(2-fluoro-6-(2H-1,2,3-triazol-2-yl)phenyl)
((1S,4R,6R)-6-((5-(trifluoromethyl)pyridin-
2-yl)oxy)-2-azabicyclo[2.2.1]heptan-2-yl)methanone

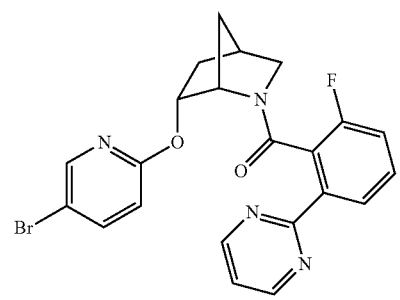 [SMILES: O=C(c1c(F)cccc1-c1ncccn1)N1CC2CC(Oc3ccc(Br)cn3)C1C2]

((1S,4R,6R)-6-((5-bromopyridin-2-yl)
oxy)-2-azabicyclo[2.2.1]heptan-2-yl)(2-fluoro-6-
(pyrimidin-2-yl)phenyl)methanone

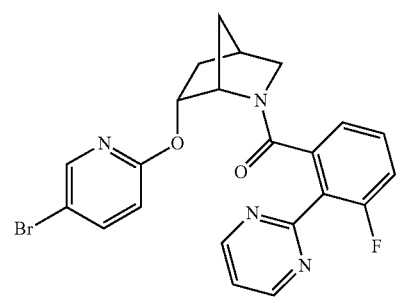 [SMILES: O=C(c1cccc(F)c1-c1ncccn1)N1CC2CC(Oc3ccc(Br)cn3)C1C2]

((1S,4R,6R)-6-((5-bromopyridin-2-yl)
oxy)-2-azabicyclo[2.2.1]heptan-2-yl)(3-fluoro-2-
(pyrimidin-2-yl)phenyl)methanone

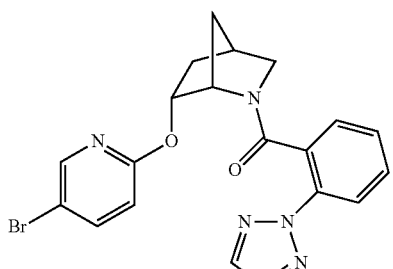

(2-(2H-1,2,3-traizol-2-yl)phenyl)
((1S,4R,6R)-6-((5-bromopyridin-2-yl)
oxy)-2-azabicyclo[2.2.1]heptan-2-yl)methanone

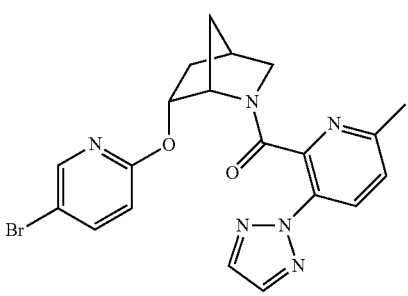 [SMILES: Cc1ccc(-n2nccn2)c(C(=O)N2CC3CC(Oc4ccc(Br)cn4)C2C3)n1]

((1S,4R,6R)-6-((5-bromopyridin-2-yl)
oxy)-2-azabicyclo[2.2.1]heptan-2-yl)(6-methyl-3-
(2H-1,2,3-triazol-2-yl)pyridin-2-yl)methanone

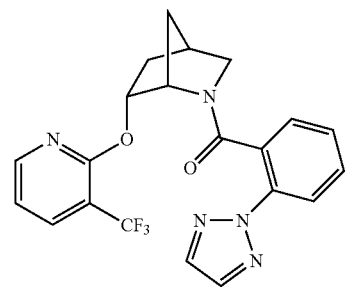 [SMILES: O=C(c1ccccc1-n1nccn1)N1CC2CC(Oc3ncccc3C(F)(F)F)C1C2]

(2-(2H-1,2,3-triazol-2-yl)phenyl)
((1S,4R,6R)-6-((3-(trifluoromethyl)pyridin-2-yl)
oxy)-2-azabicyclo[2.2.1]heptan-2-yl)methanone

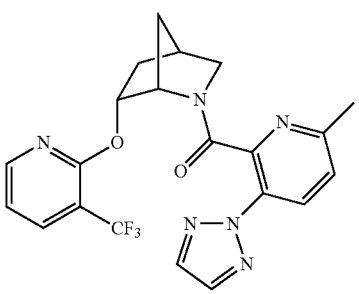 [SMILES: Cc1ccc(-n2nccn2)c(C(=O)N2CC3CC(Oc4ncccc4C(F)(F)F)C2C3)n1]

(6-methyl-3-(2H-1,2,3-triazol-2-yl)pyridin-2-yl)
((1S,4R,6R)-6-((3-(trifluoromethyl)pyridin-2-yl)
oxy)-2-azabicyclo[2.2.1]heptan-2-yl)methanone

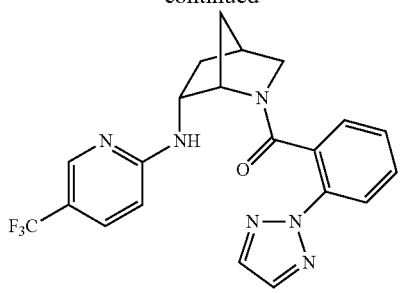

(2-(2H-1,2,3-triazol-2-yl)phenyl)
((1S,4R,6R)-6-((5-(trifluoromethyl)pyridin-2-yl)
amino)-2-azabicyclo[2.2.1]heptan-2-yl)methanone

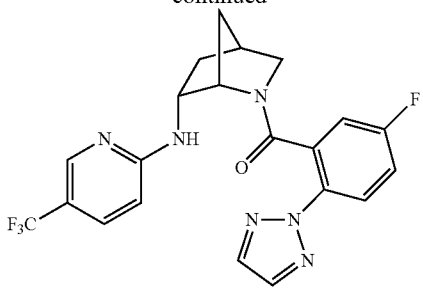

(5-fluoro-2-(2H-1,2,3-triazol-2-yl)phenyl)
((1S,4R,6R)-6-((5-(trifluoromethyl)pyridin-2-yl)
amino)-2-azabicyclo[2.2.1]heptan-2-yl)methanone

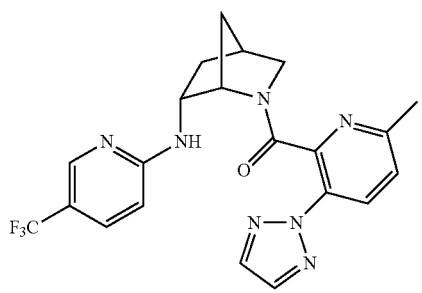 [SMILES: Cc1ccc(-n2nccn2)c(C(=O)N2CC3CC(Nc4ccc(C(F)(F)F)cn4)C2C3)n1]

(6-methyl-3-(2H-1,2,3-triazol-2-yl)pyridin-2-yl)
((1S,4R,6R)-6-((5-(trifluoromethyl)pyridin-2-yl)
amino)-2-azabicyclo[2.2.1]heptan-2-yl)methanone

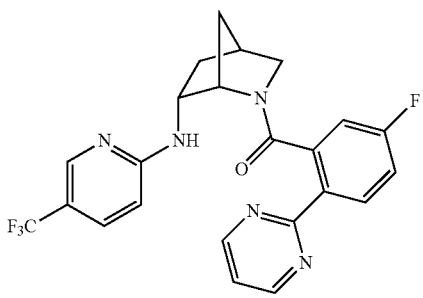

(5-fluoro-2-(pyrimidin-2-yl)phenyl)
((1S,4R,6R)-6-((5-(trifluoromethyl)pyridin-2-yl)
amino)-2-azabicyclo[2.2.1]heptan-2-yl)methanone

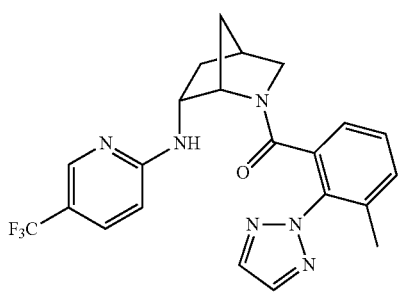 [SMILES: Cc1cccc(C(=O)N2CC3CC(Nc4ccc(C(F)(F)F)cn4)C2C3)c1-n1nccn1]

(3-methyl-2-(2H-1,2,3-triazol-2-yl)phenyl)
((1S,4R,6R)-6-((5-(trifluoromethyl)pyridin-2-yl)
amino)-2-azabicyclo[2.2.1]heptan-2-yl)methanone

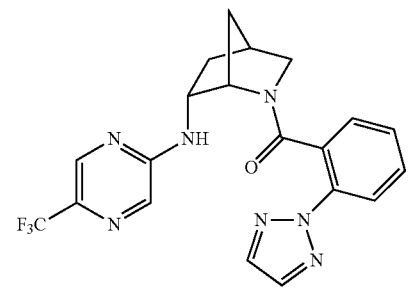

(2-(2H-1,2,3-triazol-2-yl)phenyl)
((1S,4R,6R)-6-((5-(trifluoromethyl)pyrazin-2-yl)
amino)-2-azabicyclo[2.2.1]heptan-2-yl)methanone

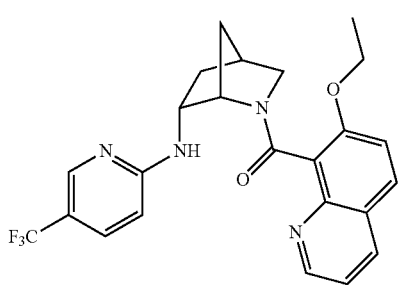 [SMILES: CCOc1ccc2cccnc2c1C(=O)N1CC2CC(Nc3ccc(C(F)(F)F)cn3)C1C2]

(7-ethoxyquinolin-8-yl)
((1S,4R,6R)-6-((5-(trifluoromethyl)pyridin-2-yl)
amino)-2-azabicyclo[2.2.1]heptan-2-yl)methanone

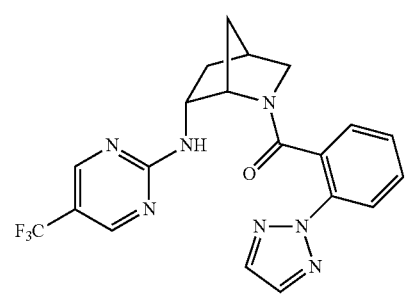 [SMILES: O=C(c1ccccc1-n1nccn1)N1CC2CC(Nc3ncc(C(F)(F)F)cn3)C1C2]

(2-(2H-1,2,3-triazol-2-yl)phenyl)
((1S,4R,6R)-6-((5-(trifluoromethyl)pyrimidin-2-yl)
amino)-2-azabicyclo[2.2.1]heptan-2-yl)methanone

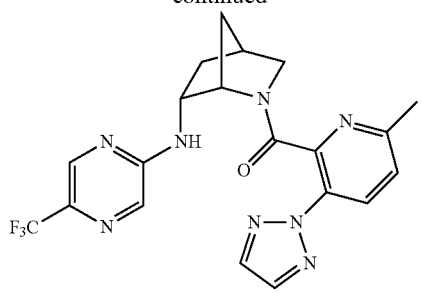

(6-methyl-3-(2H-1,2,3-triazol-2-yl)pyridin-2-yl)
((1S,4R,6R)-6-((5-(trifluoromethyl)pyrazin-2-yl)
amino)-2-azabicyclo[2.2.1]heptan-2-yl)methanone

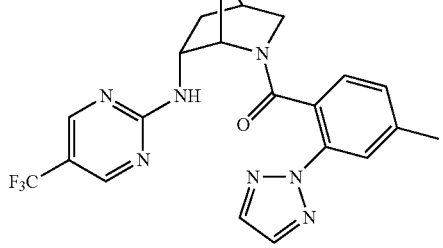

(4-methyl-2-(2H-1,2,3-triazol-2-yl)phenyl)
((1S,4R,6R)-6-((5-(trifluoromethyl)pyrimidin-2-yl)
amino)-2-azabicyclo[2.2.1]heptan-2-yl)methanone

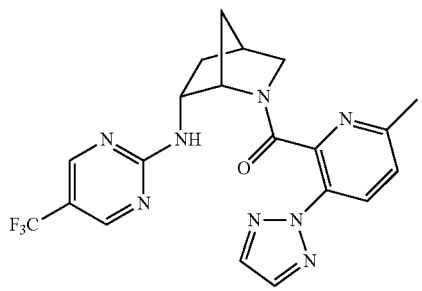 [SMILES: Cc1ccc(-n2nccn2)c(C(=O)N2CC3CC(Nc4ncc(C(F)(F)F)cn4)C2C3)n1]

(6-methyl-3-(2H-1,2,3-triazol-2-yl)pyridin-2-yl)
((1S,4R,6R)-6-((5-(trifluoromethyl)pyrimidin-2-yl)
amino)-2-azabicyclo[2.2.1]heptan-2-yl)methanone

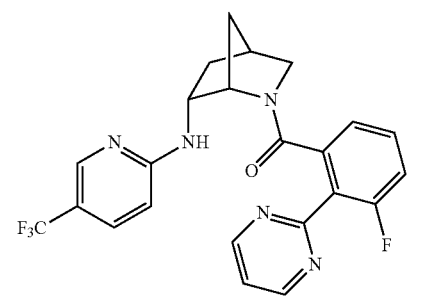

(3-fluoro-2-(pyrimidin-2-yl)phenyl)
((1S,4R,6R)-6-((5-(trifluoromethyl)pyridin-2-yl)
amino)-2-azabicyclo[2.2.1]heptan-2-yl)methanone

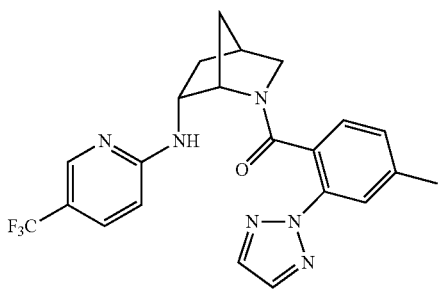

(4-methyl-2-(2H-1,2,3-triazol-2-yl)phenyl)
((1S,4R,6R)-6-((5-(trifluoromethyl)pyridin-2-yl)
amino)-2-azabicyclo[2.2.1]heptan-2-yl)methanone

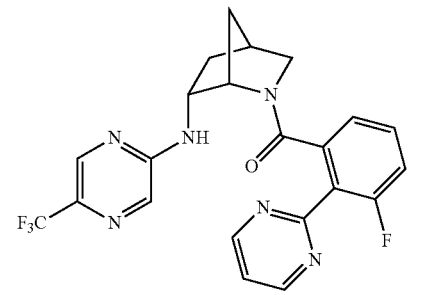

(3-fluoro-2-(pyrimidin-2-yl)phenyl)
((1S,4R,6R)-6-((5-(trifluoromethyl)pyrazin-2-yl)
amino)-2-azabicyclo[2.2.1]heptan-2-yl)methanone

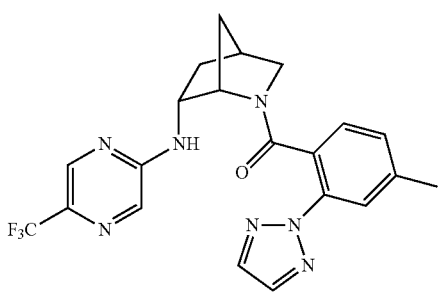 [SMILES: Cc1ccc(C(=O)N2CC3CC(Nc4cnc(C(F)(F)F)cn4)C2C3)c(-n2nccn2)c1]

(4-methyl-2-(2H-1,2,3-triazol-2-yl)phenyl)
((1S,4R,6R)-6-((5-(trifluoromethyl)pyrazin-2-yl)
amino)-2-azabicyclo[2.2.1]heptan-2-yl)methanone

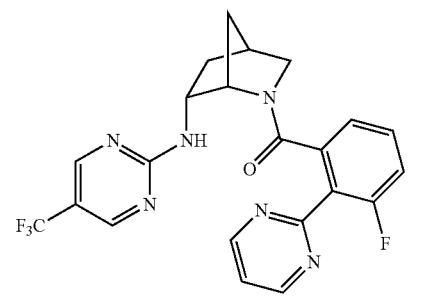 [SMILES: O=C(c1cccc(F)c1-c1ncccn1)N1CC2CC(Nc3ccc(C(F)(F)F)cn3)C1C2]

(3-fluoro-2-(pyrimidin-2-yl)phenyl)
((1S,4R,6R)-6-((5-(trifluoromethyl)pyrimidin-2-yl)
amino)-2-azabicyclo[2.2.1]heptan-2-yl)methanone

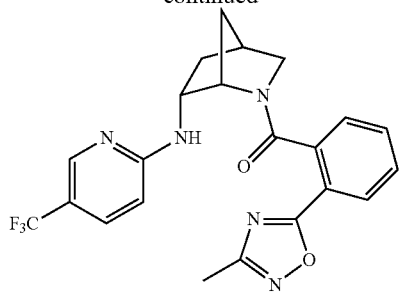

(2-(3-methyl-1,2,4-oxadiazol-5-yl)phenyl)
((1S,4R,6R)-6-((5-(trifluoromethyl)pyridin-2-yl)
amino)-2-azabicyclo[2.2.1]heptan-2-yl)methanone

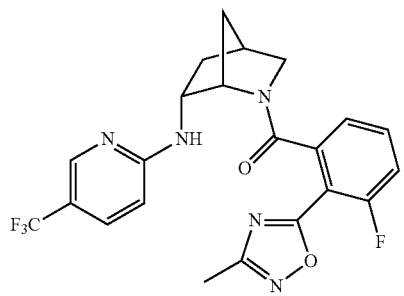 [SMILES: Cc1noc(-c2c(F)cccc2C(=O)N2CC3CC(Nc4ccc(C(F)(F)F)cn4)C2C3)n1]

(3-fluoro-2-(3-methyl-1,2,4-oxadiazol-5-yl)phenyl)
((1S,4R,6R)-6-((5-(trifluoromethyl)pyridin-2-yl)
amino)-2-azabicyclo[2.2.1]heptan-2-yl)methanone

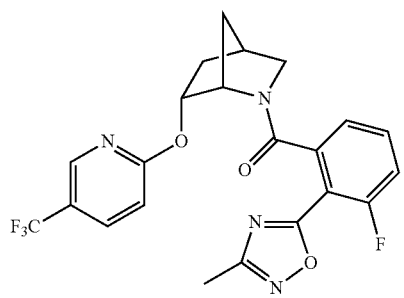 [SMILES: Cc1noc(-c2c(F)cccc2C(=O)N2CC3CC(Oc4ccc(C(F)(F)F)cn4)C2C3)n1]

(3-fluoro-2-(3-methyl-1,2,4-oxadiazol-5-yl)phenyl)
((1S,4R,6R)-6-((5-(trifluoromethyl)pyridin-2-yl)
oxy)-2-azabicyclo[2.2.1]heptan-2-yl)methanone

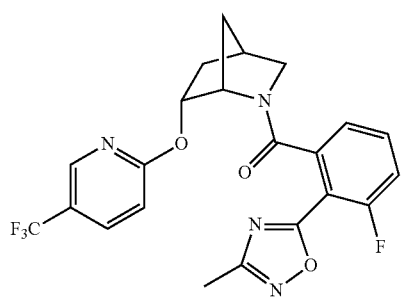 [SMILES: Cc1noc(-c2c(F)cccc2C(=O)N2CC3CC(Oc4ccc(C(F)(F)F)cn4)C2C3)n1]

(3-fluoro-2-(3-methyl-1,2,4-oxadiazol-5-yl)phenyl)
((1S,4R,6R)-6-((5-(trifluoromethyl)pyridin-2-yl)
oxy)-2-azabicyclo[2.2.1]heptan-2-yl)methanone

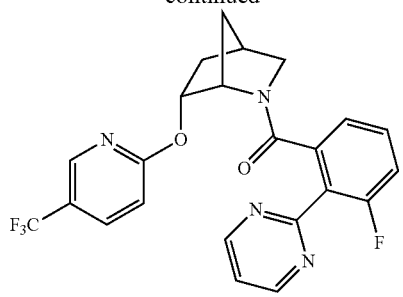

(3-fluoro-2-(pyrimidin-2-yl)phenyl)
((1S,4R,6R)-6-((5-(trifluoromethyl)pyridin-2-yl)
oxy)-2-azabicyclo[2.2.2]octan-2-yl)methanone

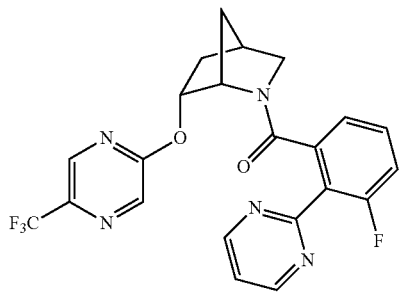 [SMILES: O=C(c1cccc(F)c1-c1ncccn1)N1CC2CC(Oc3cnc(C(F)(F)F)cn3)C1C2]

(3-fluoro-2-(pyrimidin-2-yl)phenyl)
((1S,4R,6R)-6-((5-(trifluoromethyl)pyrazin-2-yl)
oxy)-2-azabicyclo[2.2.2]octan-2-yl)methanone

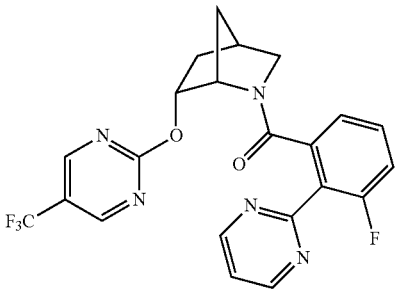

(3-fluoro-2-(pyrimidin-2-yl)phenyl)
((1S,4R,6R)-6-((5-(trifluoromethyl)pyrimidin-2-yl)
oxy)-2-azabicyclo[2.2.2]octan-2-yl)methanone

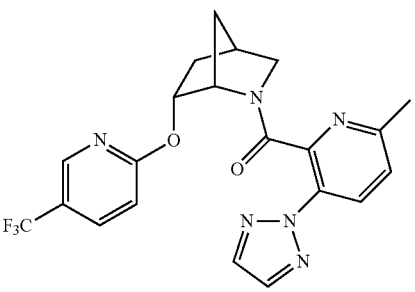 [SMILES: Cc1ccc(-n2nccn2)c(C(=O)N2CC3CC(Oc4ccc(C(F)(F)F)cn4)C2C3)n1]

(6-methyl-3-(2H-1,2,3-traizol-2-yl)pyridin-2-yl)
((1S,4R,6R)-6-((5-(trifluoromethyl)pyridin-2-yl)
oxy)-2-azabicyclo[2.2.2]octan-2-yl)methanone

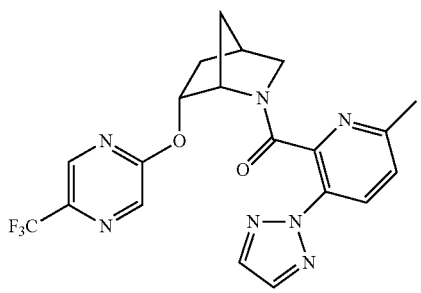 [SMILES: Cc1ccc(-n2nccn2)c(C(=O)N2CC3CC(Oc4cnc(C(F)(F)F)cn4)C2C3)n1]

(6-methyl-3-(2H-1,2,3-traizol-2-yl)pyridin-2-yl)
((1S,4R,6R)-6-((5-(trifluoromethyl)pyrazin-2-yl)
oxy)-2-azabicyclo[2.2.2]octan-2-yl)methanone

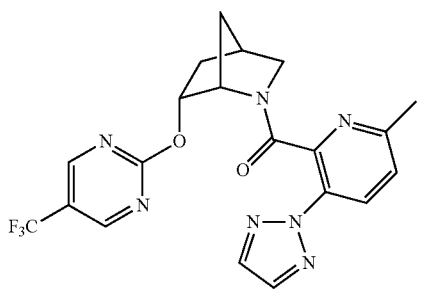 [SMILES: Cc1ccc(-n2nccn2)c(C(=O)N2CC3CC(Oc4ncc(C(F)(F)F)cn4)C2C3)n1]

(6-methyl-3-(2H-1,2,3-traizol-2-yl)pyridin-2-yl)
((1S,4R,6R)-6-((5-(trifluoromethyl)pyrimidin-2-yl)
oxy)-2-azabicyclo[2.2.2]octan-2-yl)methanone

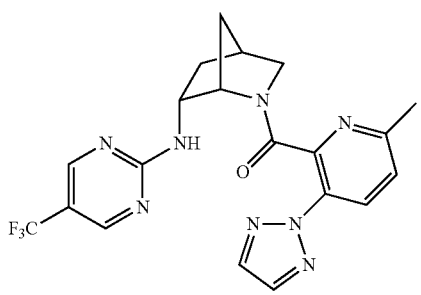 [SMILES: Cc1ccc(-n2nccn2)c(C(=O)N2CC3CC(Nc4ncc(C(F)(F)F)cn4)C2C3)n1]

(6-methyl-3-(2H-1,2,3-traizol-2-yl)pyridin-2-yl)
((1S,4R,6R)-6-((5-(trifluoromethyl)pyrimidin-2-yl)
amino)-2-azabicyclo[2.2.2]octan-2-yl)methanone

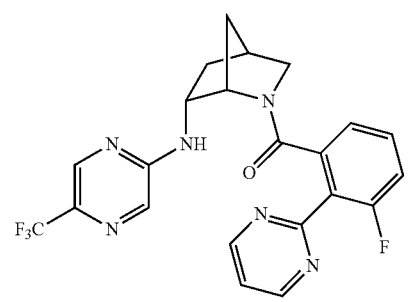 [SMILES: O=C(c1cccc(F)c1-c1ncccn1)N1CC2CC(Nc3cnc(C(F)(F)F)cn3)C1C2]

(3-fluoro-2-(pyrimidin-2-yl)phenyl)
((1S,4R,6R)-6-((5-(trifluoromethyl)pyrazin-2-yl)
amino)-2-azabicyclo[2.2.2]octan-2-yl)methanone

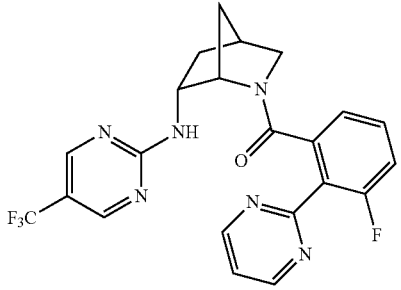 [SMILES: O=C(c1cccc(F)c1-c1ncccn1)N1CC2CC(Nc3ncc(C(F)(F)F)cn3)C1C2]

(3-fluoro-2-(pyrimidin-2-yl)phenyl)
((1S,4R,6R)-6-((5-(trifluoromethyl)pyrimidin-2-yl)
amino)-2-azabicyclo[2.2.2]octan-2-yl)methanone

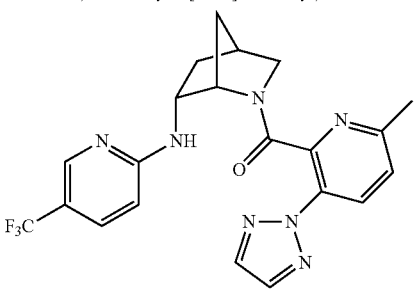

(6-methyl-3-(2H-1,2,3-triazol-2-yl)pyridin-2-yl)
((1S,4R,6R)-6-((5-(trifluoromethyl)pyridin-2-yl)
amino)-2-azabicyclo[2.2.2]octan-2-yl)methanone

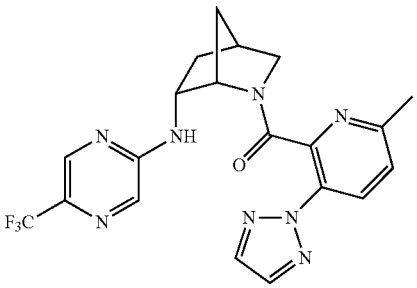 [SMILES: Cc1ccc(-n2nccn2)c(C(=O)N2CC3CC(Nc4cnc(C(F)(F)F)cn4)C2C3)n1]

(6-methyl-3-(2H-1,2,3-triazol-2-yl)pyridin-2-yl)
((1S,4R,6R)-6-((5-(trifluoromethyl)pyrazin-2-yl)
amino)-2-azabicyclo[2.2.2]octan-2-yl)methanone

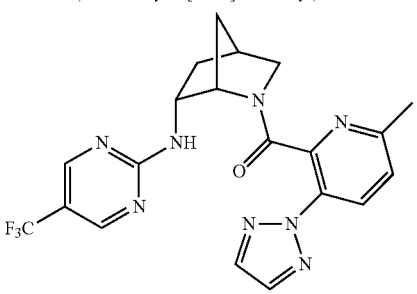

(6-methyl-3-(2H-1,2,3-triazol-2-yl)pyridin-2-yl)
((1S,4R,6R)-6-((5-(trifluoromethyl)pyimidin-2-yl)
amino)-2-azabicyclo[2.2.2]octan-2-yl)methanone and pharmaceutically acceptable salts thereof.

* * * * *